United States Patent
Chou et al.

(10) Patent No.: US 11,906,432 B2
(45) Date of Patent: *Feb. 20, 2024

(54) ENHANCED, RAPID, HOMOGENEOUS, CELL STAINING AND ASSAY

(71) Applicant: Essenlix Corporation, Monmouth Junction, NJ (US)

(72) Inventors: Stephen Y. Chou, Princeton, NJ (US); Wei Ding, Princeton, NJ (US); Ji Li, Princeton, NJ (US); Shengjian Cai, Bridgewater, NJ (US); Yufan Zhang, Monmouth Junction, NJ (US); Jia Peng, Monmouth Junction, NJ (US)

(73) Assignee: Essenlix Corporation, Monmouth Junction, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/268,799

(22) PCT Filed: Aug. 23, 2019

(86) PCT No.: PCT/US2019/048043
§ 371 (c)(1),
(2) Date: Feb. 16, 2021

(87) PCT Pub. No.: WO2020/041781
PCT Pub. Date: Feb. 27, 2020

(65) Prior Publication Data
US 2021/0247317 A1    Aug. 12, 2021

Related U.S. Application Data

(60) Provisional application No. 62/722,172, filed on Aug. 23, 2018.

(51) Int. Cl.
*G01N 21/64* (2006.01)
*G01N 1/30* (2006.01)
(Continued)

(52) U.S. Cl.
CPC .......... *G01N 21/6458* (2013.01); *G01N 1/30* (2013.01); *G01N 21/76* (2013.01); *G01N 33/54373* (2013.01)

(58) Field of Classification Search
CPC .......... G01N 21/6458; G01N 21/6486; G01N 2021/036; G01N 2021/0364; G01N 1/30;
(Continued)

(56) References Cited

U.S. PATENT DOCUMENTS 8,097,404 B2   1/2012   Ribault et al.
9,023,615 B2   5/2015   Weidner et al.
(Continued)

FOREIGN PATENT DOCUMENTS

WO   2018148461 A1   8/2018
WO   2018231877 A1   12/2018

OTHER PUBLICATIONS

International Preliminary Report on Patentability for PCT/US2019/048043 established by IPEA/US completed on Dec. 17, 2020.
(Continued)

*Primary Examiner* — Christopher L Chin

(57) ABSTRACT

The present invention provides, among other things, devices, kits, apparatus, and methods for rapid homogenous cell staining and imaging. Particularly, in some embodiments, the present invention can immunochemically stain a cell or a tissue in less than 60 seconds without washing. In some embodiments, the present invention stains and observers analyte (protein or nucleic acid) inside a cell in 60 seconds without wash.

85 Claims, 8 Drawing Sheets

(51) Int. Cl.
*G01N 21/76* (2006.01)
*G01N 33/543* (2006.01)

(58) Field of Classification Search
CPC ............ G01N 21/76; G01N 33/54373; G01N 2333/195; G01N 2333/70514; B01L 3/508; B01L 2300/043
USPC ........ 356/244, 246; 422/401, 408, 425, 436, 422/551; 435/288.3, 288.7; 436/805, 436/807
See application file for complete search history.

(56) References Cited

U.S. PATENT DOCUMENTS

| | | |
|---|---|---|
| 9,475,049 B2 | 10/2016 | Siciliano et al. |
| 2018/0202903 A1 | 7/2018 | Chou et al. |

OTHER PUBLICATIONS

Written Opinion of the International Searching authority for PCT/US2019/048043 established by ISA/US completed on Nov. 15, 2019.
Mason DJ, Shanmuganathan S, Mortimer FC, Gant VA. A fluorescent Gram stain for flow cytometry and epifluorescence microscopy. Appl Environ Microbiol. Jul. 1998;64(7):2681-5.

(a) Chlamydia Positive Cells (b) Chlamydia Negative Cells

ENHANCED, RAPID, HOMOGENEOUS, CELL STAINING AND ASSAY

CROSS-REFERENCE TO RELATED APPLICATIONS

This application is a National Stage entry (§ 371) application of International Application No. PCT/US2019/048043, filed on Aug. 23, 2019, which claims the benefit of priority of U.S. Provisional Patent Application No. 62/722,172, filed on Aug. 23, 2018, the contents of which is relied upon and incorporated herein by reference in its entirety. The entire disclosure of any publication or patent document mentioned herein is entirely incorporated by reference.

FIELD

Among other things, the present invention is related to devices and methods of performing rapid cell staining and imaging, such as but not limited to immunoassays and dye staining.

BACKGROUND

There are needs to have rapid cell staining and imaging, and/or need to use the cellphone to perform such.

SUMMARY OF INVENTION

Among other things, the present invention provides devices, kits, apparatus, and methods for rapid homogenous cell staining and imaging. Particularly, in some embodiments, the present invention immunochemically stain a cell or a tissue in less than 60 seconds without washing. In some embodiments, the present invention stains and observers analyte (protein or nucleic acid) inside a cell in 60 seconds without wash.

One aspect of the present invention is to use QMAX card with dry reagent on the sample contact area of one or both plates to stain a sample (e.g., cells or tissues)

Another aspect of the present invention is to use the QMAX card to configure the thickness of the sample into a thin layer to reduce background signal, so that the stained cells become observable without any washing and/or without opening the two plates of QMAX card. (The unbound labeled detection agents (i.e. those are not bound to the target cells) in a sample are a major source of the background optical signal), wherein the detection agent can be protein or nucleic acid.

Another aspect of the present invention is to use the QMAX card to configure the thickness of the sample into a thin layer, so that the stained cells do not substantially overlap in the direction normal to the sample thickness, which can allow a stained cell being viewed from top of the QMAX card without being substantially blocked by other stained cells.

Another aspect of the present invention is to increase an optical signal (i.e. light signal) from a stain cell by unselectively stain the cells in the sample by other dye that emit light in the same wavelength as that of the dye that selectively stained the cell. The addition (i.e. combination) of the optical signal can make the selectively stained cell observable (i.e. distinguishable from the other part of the sample), even without washing away unbonded days in the sample from the background of the sample.

Another aspect of the present invention is to use a second labeled antibody to stain the target cells, where the second labeled antibody selectively attaches to another epitope of the target binding site, and has an optical label emit light of wavelength overlap with that of the first labeled antibody.

Another aspect of the present invention to use a combination or multiple labeled antibody, labeled probe, dye to stain the target cells, where multiple labeled antibody, labeled probe, dye label emit light of wavelength overlap with that of the first labeled antibody.

Another aspect of the present invention is to provide the devices and methods to perform rapid RNA fluorescence in situ hybridization (RNA-FISH) staining.

Another aspect of the present invention is to do Gram positive and Gram negative staining.

Another aspect of the present invention is to do immune staining.

In some embodiments, the present invention provides a method of enhancing a homogenous detection of an analyte in a cell that is in a sample, comprising: (a) having a first plate and a second plate, each has a sample contact area on its surface, wherein the sample contact surfaces contact a sample comprising a cell that contains or is suspected to contain an analyte, (b) having a detection probe that specifically binds the analyte and is capable of emitting a light at a wavelength, wherein the detection probe diffuses in the sample; (c) having an optical enhancer that binds to the cell and is capable of emit lighting in a wavelength that overlaps with or within a 30 nm from the wavelength of the light emitted by the detection probe; (d) sandwiching the sample, the detection probe, and the optical enhancer between the two sample contact areas of the two plates to form a thin layer of a thickness of 200 microns (um) or less; and (e) imaging using an imager, after the step (d) and without using any washing step, the thin layer to detect the cell that has the analyte bound to the detection probe; wherein the thin layer sample thickness is configured so that for a given concentration of the cell in the sample, each individual cell does not substantially overlap other cells in the imaging; wherein the thickness of the thin layer, the concentration of the detection probe in the sample, or the concentration of the optical enhancer in the sample is configured to make, in the step (e) of imaging, in the thin layer, the location having the bound detection probe is distinguishable from the locations not having the bound detection probe, wherein the bound detection probe is the detection probe bound to the analyte in the cell.

In some embodiments, the present invention provides a method of enhancing a homogenous detection of an analyte in a cell that is in a sample, comprising: (a) having a first plate and a second plate, each has a sample contact area on its surface, wherein the sample contact surfaces contact a sample comprising a cell that contains or is suspected to contain an analyte, (b) depositing, on at least one of the sample contact areas, a detection probe that specifically binds the analyte and emits a light at a wavelength, wherein the detection probe diffuses in the sample; (c) having an optical enhancer that binds to the cell and emits light in a wavelength range that overlaps with or within a 30 nm from the wavelength of the light emitted by the detection probe; (d) sandwiching the sample, the detection probe, and the optical enhancer between the two sample contact areas of the two plates to form a thin layer, wherein the thin layer has a thickness of 150 microns (um) or less; and (e) imaging using an imager, after the step (d) and without using any washing step, the thin layer to detect the detection probe that has specifically bound to the analyte; wherein the thin layer sample thickness is configured so that for a given concentration of the cell in the sample, each individual cell does not substantially overlap other cells in the imaging; wherein the thickness of the thin layer, the concentration of the detection probe in the sample, or the concentration of the optical enhancer in the sample is configured to make, in the step (e) of imaging, in the thin layer, the location having the bound detection probe is distinguishable from the locations not having the bound detection probe, wherein the bound detection probe is the detection probe bound to the analyte in the cell.

In some embodiments, the present invention provides a method of enhancing a homogenous detection of an analyte in a cell that is in a sample, comprising: (a) having a first plate and a second plate, each has a sample contact area on its surface, wherein the sample contact surfaces contact a sample comprising a cell that contains or is suspected to contain an analyte, (b) depositing, on at least one of the sample contact areas, a detection probe that specifically binds the analyte and emits a light at a wavelength, wherein the detection probe diffuses in the sample; (c) depositing, on at least one of the sample contact areas, an optical enhancer that binds to the cell and emits light in a wavelength range that overlaps with or within a 30 nm from the wavelength of the light emitted by the detection probe, wherein the optical enhancer diffuses in the sample; (d) sandwiching the sample, the detection probe, and the optical enhancer between the two sample contact areas of the two plates to form a thin layer, wherein the thin layer has a thickness of 150 microns (um) or less; and (e) imaging using an imager, after the step (d) and without using any washing step, the thin layer to detect the detection probe that has specifically bound to the analyte; wherein the thin layer sample thickness is configured so that for a given concentration of the cell in the sample, each individual cell does not substantially overlap other cells in the imaging; wherein the thickness of the thin layer, the concentration of the detection probe in the sample, or the concentration of the optical enhancer in the sample is configured to make, in the step (e) of imaging, in the thin layer, the location having the bound detection probe is distinguishable from the locations not having the bound detection probe, wherein the bound detection probe is the detection probe bound to the analyte in the cell.

In some embodiments, the present invention provides a kit for enhancing a homogenous detection of an analyte in a cell that is in a sample, comprising: (a) a first plate and a second plate, each has a sample contact area on its surface, wherein the sample contact surfaces contact a sample comprising a cell that contains or is suspected to contain an analyte, (b) a detection probe that specifically binds the analyte and is capable of emitting a light at a wavelength, wherein the detection probe diffuses in the sample; (c) an optical enhancer that binds to the cell and emits lighting in a wavelength that overlaps with or within a 30 nm from the wavelength of the light emitted by the detection probe; wherein the first and second plates are configured to sandwich the sample, the detection probe, and the optical enhancer between the two sample contact areas to form a thin layer of a thickness of 200 microns (um) or less; and wherein the thin layer sample thickness is configured so that for a given concentration of the cell in the sample, each individual cell does not substantially overlap other cells in the imaging; wherein the thickness of the thin layer, the concentration of the detection probe in the sample, or the concentration of the optical enhancer in the sample is configured to make, in the step (e) of imaging, in the thin layer, the location having the bound detection probe is distinguishable from the locations not having the bound detection probe, wherein the bound detection probe is the detection probe bound to the analyte in the cell.

In some embodiments, the present invention provides a device of enhancing a homogenous detection of an analyte in a cell that is in a sample, comprising: (a) a first plate and a second plate, each has a sample contact area on its surface, wherein the sample contact surfaces contact a sample comprising a cell that contains or is suspected to contain an analyte, (b) a detection probe that specifically binds the analyte and emits a light at a wavelength, wherein the detection probe is coated on at least one of the sample contact areas and diffuses in the sample; (c) an optical enhancer that binds to the cell and emits light in a wavelength range that overlaps with or within a 30 nm from the wavelength of the light emitted by the detection probe; (d) the sample contact areas in the first and second plates faces each other and sandwich the sample, the detection probe, and the optical enhancer between the two sample contact areas of the two plates to form a thin layer, wherein the thin layer has a thickness of 150 microns (um) or less; and (e) an imager that images the thin layer to detect the detection probe that has specifically bound to the analyte; wherein the thin layer sample thickness is configured so that for a given concentration of the cell in the sample, each individual cell does not substantially overlap other cells in the imaging; wherein the thickness of the thin layer, the concentration of the detection probe in the sample, or the concentration of the optical enhancer in the sample is configured to make, in the step (e) of imaging, in the thin layer, the location having the bound detection probe is distinguishable from the locations not having the bound detection probe, wherein the bound detection probe is the detection probe bound to the analyte in the cell.

In some embodiments, the present invention provides a method of enhancing a homogenous detection of an analyte in a cell that is in a sample, comprising: (a) a first plate and a second plate, each has a sample contact area on its surface, wherein the sample contact surfaces contact a sample comprising a cell that contains or is suspected to contain an analyte, (b) a detection probe that specifically binds the analyte and emits a light at a wavelength, wherein the detection probe is coated on one or both of the sample contact areas and diffuses in the sample; (c) an optical enhancer that binds to the cell and emits light in a wavelength range that overlaps with or within a 30 nm from the wavelength of the light emitted by the detection probe, wherein the optical enhancer is coated on one or both of the sample contact areas and diffuses in the sample; (d) the sample contact areas in the first and second plates faces each other and sandwich the sample, the detection probe, and the optical enhancer between the two sample contact areas of the two plates to form a thin layer, wherein the thin layer has a thickness of 150 microns (um) or less; and (e) imaging using an imager, after the step (d) and without using any washing step, the thin layer to detect the detection probe that has specifically bound to the analyte; wherein the thin layer sample thickness is configured so that for a given concentration of the cell in the sample, each individual cell does not substantially overlap other cells in the imaging; wherein the thickness of the thin layer, the concentration of the detection probe in the sample, or the concentration of the optical enhancer in the sample is configured to make, in the step (e) of imaging, in the thin layer, the location having the bound detection probe is distinguishable from the locations not having the bound detection probe, wherein the bound detection probe is the detection probe bound to the analyte in the cell.

In some embodiments, the present invention provides a system of enhancing a homogenous detection of an analyte in a cell that is in a sample, comprising: (a) a device or a kit of any prior claims; and (b) a communication.

In some embodiments, the present invention provides a method of using a system of enhancing a homogenous detection of an analyte in a cell that is in a sample, comprising: (a) having a device or a kit of any prior claims; and (b) having a communication.

In some embodiments, the present invention provides a method for a rapid homogenous detection of an analyte inside a membrane of a cell in a sample, comprising: (a) having a first plate and a second plate, each has a sample contact area on its surface, wherein the sample contact surfaces contact a sample comprising a cell that contains or is suspected to contain an analyte inside of the cell membrane, (b) having a detection probe that specifically binds the analyte and is capable of emitting a light at a wavelength, wherein the detection probe diffuses in the sample; (c) having a permeabilization agent that makes a membrane of the cell permeable to the detection probe; (d) sandwiching the sample, the detection probe, and the permeabilization agent between the two sample contact areas of the two plates to form a thin layer of a thickness of 200 microns (um) or less; and (e) imaging, after the step (d) and without a washing step, the thin layer to detect the cell that has the analyte bound to the detection probe; wherein the thin layer sample thickness is configured so that for a given concentration of the cell in the sample, each individual cell does not substantially overlap other cells in the imaging; wherein the thickness of the thin layer and the concentration of the detection probe in the sample, are configured to make, in the thin layer, the location having the detection probe that bound to the analyte inside the cell membrane is distinguishable from the locations that do not have the cell; and wherein the washing step is a step of removing unbound detection probe, permeabilization reagent, or both from the sample contact areas.

In some embodiments, the present invention provides a method for a rapid homogenous detection of an analyte inside a membrane of a cell in a sample, comprising: (a) having a first plate and a second plate, each has a sample contact area on its surface, wherein the sample contact surfaces contact a sample comprising a cell that contains or is suspected to contain an analyte, (b) depositing, on at least one of the sample contact areas, a detection probe that specifically binds the analyte and emits a light at a wavelength, wherein the detection probe diffuses in the sample; (c) having a permeabilization agent that makes a membrane of the cell permeable to the detection probe; (d) sandwiching the sample, the detection probe, and the optical enhancer between the two sample contact areas of the two plates to form a thin layer, wherein the thin layer has a thickness of 150 microns (um) or less; and (e) imaging using an imager, after the step (d) and without using any washing step, the thin layer to detect the detection probe that has specifically bound to the analyte; wherein the thin layer sample thickness is configured so that for a given concentration of the cell in the sample, each individual cell does not substantially overlap other cells in the imaging; wherein the thickness of the thin layer, the concentration of the detection probe in the sample, or the concentration of the optical enhancer in the sample is configured to make, in the step (e) of imaging, in the thin layer, the location having the bound detection probe is distinguishable from the locations not having the bound detection probe, wherein the bound detection probe is the detection probe bound to the analyte in the cell; and wherein the washing step is a step of removing unbound detection probe, permeabilization reagent, or both from the sample contact areas.

In some embodiments, the present invention provides a method for a rapid homogenous detection of an analyte inside a membrane of a cell in a sample, comprising: (a) having a first plate and a second plate, each has a sample contact area on its surface, wherein the sample contact surfaces contact a sample comprising a cell that contains or is suspected to contain an analyte, (b) depositing, on at least one of the sample contact areas, a detection probe that specifically binds the analyte and emits a light at a wavelength, wherein the detection probe diffuses in the sample; (c) depositing, on at least one of the sample contact areas, an optical enhancer that binds to the cell and emits light in a wavelength range that overlaps with or within a 30 nm from the wavelength of the light emitted by the detection probe, wherein the optical enhancer diffuses in the sample; (d) sandwiching the sample, the detection probe, and the optical enhancer between the two sample contact areas of the two plates to form a thin layer, wherein the thin layer has a thickness of 150 microns (um) or less; and (e) imaging using an imager, after the step (d) and without using any washing step, the thin layer to detect the detection probe that has specifically bound to the analyte; wherein the thin layer sample thickness is configured so that for a given concentration of the cell in the sample, each individual cell does not substantially overlap other cells in the imaging; wherein the thickness of the thin layer, the concentration of the detection probe in the sample, or the concentration of the optical enhancer in the sample is configured to make, in the step (e) of imaging, in the thin layer, the location having the bound detection probe is distinguishable from the locations not having the bound detection probe, wherein the bound detection probe is the detection probe bound to the analyte in the cell; and wherein the washing step is a step of removing unbound detection probe, permeabilization reagent, or both from the sample contact areas.

In some embodiments, the present invention provides a method of a homogenous detection of a Gram positive cell or Gram negative cell in a sample, comprising: (a) having a first plate and a second plate, each has a sample contact area on its surface, wherein the sample contact surfaces contact a sample that contains or is suspected to contain a Gram positive cell or Gram negative cell, (b) depositing, on at least one of the sample contact areas, a Gram positive stain, a Gram negative stain, or both, wherein the Gram positive and Gram negative stains have two distinguishable colors; wherein the Gram positive stain stains only Gram positive cells while the Gram negative stain stains both Gram positive and negative cells; wherein, in a Gram positive cell that is stained by both Gram positive and negative stains, the Gram positive stain is designable from the Gram negative stain; (c) sandwiching the sample between the two sample contact areas of the two plates to make the sample forming a thin layer of a thickness of 150 microns (um) or less; and (d) imaging using an imager, after the step (c) and without using any washing step, the thin layer to detect cells that are stained by (i) Gram negative stain only, (ii) Gram positive stain; and (iii) both; wherein the thin layer sample thickness is configured so that for a given concentration of the cell in the sample, each individual cell does not substantially overlap other cells in the imaging; wherein a Gram positive cells displays Gram positive stain color, and a Gram negative cell displays Gram negative stain color only; wherein the thickness of the thin layer, the concentration of the detection probe in the sample, or the concentration of the optical enhancer in the sample is configured to make, in the step (e) of imaging, in the thin layer, the location having the bound detection probe is distinguishable from the locations not having the bound detection probe, wherein the bound detection probe is the detection probe bound to the analyte in the cell.

In some embodiments, the thickness of the thin layer is configured to make, in the step (e) of imaging, in the thin layer, the location having the bound detection probe is distinguishable from the locations not having the bound detection probe, wherein the bound detection probe is the detection probe bound to the analyte in the cell.

In some embodiments, the concentration of the detection probe in the sample is configured to make, in the step (e) of imaging, in the thin layer, the location having the bound detection probe is distinguishable from the locations not having the bound detection probe, wherein the bound detection probe is the detection probe bound to the analyte in the cell.

In some embodiments, the concentration of the optical enhancer in the sample is configured to make, in the step (e) of imaging, in the thin layer, the location having the bound detection probe is distinguishable from the locations not having the bound detection probe, wherein the bound detection probe is the detection probe that bound to the analyte in the cell.

In some embodiments, the first plate and the second plate are movable relative to each other into a different configuration, including an open configuration and a closed configuration, wherein: in the open configuration the first plate and the second plate are partially or entirely separated, and the sample is deposited in the sample contact area on one or both of the plates, and the separation sheet is removed from any contact with one or both of the plates; and in the closed configuration at least part of the deposited sample is compressed by the two plates into a thin layer.

In some embodiments, the present invention further comprises a plurality of spacers, wherein: (i) the first plate and the second plate are movable relative to each other into a different configuration, including an open configuration and a closed configuration, and (ii) one or both of the plates comprise spacers that are fixed with a respective plate, wherein in an open configuration, the two plates are either completely or partially separated apart, the spacing between the plates is not regulated by the spacers, and the sample is deposited on one or both of the plates; and wherein in the closed configuration, which is configured after the sample deposition in the open configuration, at least a part of the VC sample is between the two plates and in contact with the two plates, and has a highly uniform thickness that is regulated by the spacers and the two sample surfaces of the plates and is equal to or less than 150 um.

In some embodiments, the imaging comprises a step of machine learning.

In some embodiments, the imaging comprises a step of machine learning in detecting the analytes.

In some embodiments, the present invention further comprises a non-volatile storage medium that has an algorithms of machine learning.

In some embodiments, the imager further comprises a non-volatile storage medium that has an algorithms of machine learning in detecting the analytes.

In some embodiments, the analyte comprises a molecule (e.g., a protein, peptides, DNA, RNA, nucleic acid, or other molecules), cells, tissues, viruses, or nanoparticles with different shapes.

In some embodiments, the analyte comprises a molecule, a protein, peptides, DNA, RNA, ands nucleic acid.

In some embodiments, the analyte inside the cell membrane comprises a molecule, a protein, peptides, DNA, RNA, ands nucleic acid.

In some embodiments, the sample is a vapor from a biological sample, an environmental sample, a chemical sample, or a clinical sample.

In some embodiments, the detection of labeled stain reagent is fluorescence-based (refer to other Provisionals), chemiluminescence-based (refer to other Provisionals) or colorimetric-based (refer to other Provisionals) or plasmonic-based (refer to other Provisionals).

In some embodiments, the target cell is a prokaryote such as bacteria and archaea, or eukaryote such as animal cell and plant cell.

In some embodiments, the number of target cell in sample can be one or more than one.

In some embodiments, the reagents coating on the device including an agent making cell membrane or cell nucleus permeable, including but not limit to 2-[4-(2,4,4-trimethylpentan-2-yl)phenoxy]ethanol (TRITON X-100™), surfactant, Zwittergent, Dimethyl(3-myristoylaminopropyl)ammonio]propanesulfonate (ASB-14), 3-[N,N-Dimethyl(3-palmitoylaminopropyl) ammonio]-propanesulfonate (ASB-16), 3-[(3-Cholamidopropyl)dimethylammonio]-1-propanesulfonate (CHAPS), Cationic surfactant NN-[Tris (hydroxymethyl) methyl]-N-alkyl-N,N-dimethyl ammonium chloride (IIa), IIb, IIc, IId, cetyltrimethylammonium chloride (CTAC), polyoxyethylene sorbitan monolaurate (TWEEN® 20), polyoxyethylene sorbitan monopalmitate (TWEEN® 40), polyoxyethylene sorbitan monostearate (TWEEN® 60), polyoxyethylene sorbitan monooleate (TWEEN® 80), Sodium lauryl sulfate (SLS), ammonium lauryl sulfate, cetyltrimethylammonium bromide (CTAB), sodium lauryl ether sulfate (SLES), sodium myreth sulfate, docusate, perfluorooctanesulfonate, alkyl-aryl ether phosphates, alkyl ether phosphates, cetylpyridinium chloride (CPC), benzalkonium chloride (BAC), benzethonium chloride (BZT), dimethyldioctadecylammonium chloride, dioctadecyldimethlyammonium bromide (DODAB), cocamidopropyl hydroxysultaine, cocamidopropyl betaine, narrow-range ethoxylate, octaethylene glycol monododecyl ether, pentaethylene glycol monododecyl ether, nonxynols, polyethoxylated tallow amine, cocamide monoethanolamine, cocamide diethanolamine, poloxamers, glycerol monostearate, glycerol monolaurate, sorbitan monolaurate, sorbitan monostearate, sorbitan tristearate, decyl glucoside, lauryl glucoside, octyl glucoside, lauryldimethylamine oxide, dimethyl sulfoxide, phosphine oxide.

In some embodiments, the reagents coating on the device including an agent making cell membrane or cell nucleus permeable, by method of osmotic pressure difference between the cell membrane as dilution, or tuning salt concentration.

In some embodiments, the reagents coating on the device including an agent making protein cross link, including but not limit to formaldehyde, glutaraldehyde, osmium tetroxide, potassium dichromate and potassium permanganate.

In some embodiments, the dye to stain the WBC is coated onto the first plate, or the second plate or both.

In some embodiments, the dye to stain the WBC and PLT is coated onto the first plate, or the second plate or both.

In some embodiments, the dye to stain the PLT is coated onto the first plate, or the second plate or both.

In some embodiments, the reagent is coated by droplet printing into an array.

In some embodiments, the reagent is coated using the open guided flow properties of structures on plates.

In some embodiments, the reagent is coated by spray.

In some embodiments, the reagent is coated by contact printing.

In some embodiments, the reagent is coated by transfer printing.

In some embodiments, the dye to stain the RBC is coated onto the first plate, or the second plate or both.

In some embodiments, the surfactant to separate and round RBC is coated onto the first plate, or the second plate or both.

In some embodiments, the chemical to lyse RBC is coated onto the first plate, or the second plate or both.

In some embodiments, the acridine orange is coated onto the first plate, or the second plate or both.

In some embodiments, the Zwittergent is coated onto the first plate, or the second plate or both.

In some embodiments, the Methylene blue and Zwittergent is coated onto the first plate, or the second plate or both.

In some embodiments, the acridine orange and Zwittergent is coated onto the first plate, or the second plate or both.

In some embodiments, the $[1^2(2)Z,16(17^2)Z]$-13,7,7,11,11,17$^3$-Hexamethyl-1$^3$H,17$^3$H-7,11-diaza-3$^1\lambda^5$,15$^1\Delta^5$-3(4,1),15(1,4)-diquinolina-1,17(2)-bis([1,3]benzoxazola)hepta-decaphane-1$^2$(2),16(17$^2$)-diene-7,11-diium-3$^1$,15$^1$-bis (ylium) tetraiodide (YOYO dye) and Zwittergent is coated onto the first plate, or the second plate or both.

In some embodiments, the device further comprises, on one or both plates, multi reagent layers including anti-conglutination, cell lysing, cell staining, release time control material layers, and their combinations.

In some embodiments, each layer coated on the plates has a thickness of 10 nm, 100 nm, 200 nm, 500 nm, 1 um or a range between any two of the values.

In some embodiments, the anti-conglutination agent comprises ethylenediaminetetraacetic acid (EDTA), EDTA disodium, dipotassium ethylenediaminetetraacetic acid (K2EDTA), or tripotassium ethylenediaminetetraacetic acid (K3EDTA).

In some embodiments, cell stain agent comprise Wright's stain (Eosin, methylene blue), Giemsa stain (Eosin, methylene blue, and Azure B), May-Grünwald stain, Leishman's stain ("Polychromed" methylene blue (i.e. demethylated into various azures) and eosin), Erythrosine B stain (Erythrosin B), and other fluorescence stain including but not limit to Acridine orange dye, 3,3-dihexyloxacarbocyanine (DiOC6), Propidium Iodide (PI), Fluorescein Isothiocyanate (FITC) and Basic Orange 21 (B021) dye, Ethidium Bromide, Brilliant Sulfaflavine and a Stilbene Disulfonic Acid derivative, Erythrosine B or trypan blue, Hoechst 33342, Trihydrochloride, Trihydrate, and DAPI (4',6-Diamidino-2-Phenylindole, Dihydrochloride), YOYO.

In some embodiments, the cell stain agent comprise Wright's stain (Eosin, methylene blue), Giemsa stain (Eosin, methylene blue, and Azure B), May-Grünwald stain, Leishman's stain ("Polychromed" methylene blue (i.e. demethylated into various azures) and eosin), Erythrosine B stain (Erythrosin B), and other fluorescence stain including but not limit to Acridine orange dye, 3,3-dihexyloxacarbocyanine (DiOC6), Propidium Iodide (PI), Fluorescein Isothiocyanate (FITC) and Basic Orange 21 (B021) dye, Ethidium Bromide, Brilliant Sulfaflavine and a Stilbene Disulfonic Acid derivative, Erythrosine B or trypan blue, Hoechst 33342, Trihydrochloride, Trihydrate, and DAPI (4',6-Diamidino-2-Phenylindole, Dihydrochloride), YOYO dye, acid fuchsine, hematoxylin, Hoechst stains including Hoechst 33258 and Hoechst 33342, methyl green, methylene blue, Nile blue, Nile red, osmium tetraoxide, rhodamine, safranine, MeOSuc-AAPV-AMC, CFSE, BCECF/AM, silver nitrate, neutral red, pyronin Y, Calcein-AM, Dihydroethidium, Xylene Cyanol FF, Rhodamine 123, 4-Methylumbelliferyl palmitate, Fast Blue B Salt, Lucifer Yellow CH dipotassium salt, DAPI dilactate, Propidium Iodide.

In some embodiments, the cell lysing agent comprises ammonium chloride, sodium bicarbonate, ethylenediaminetetraacetic acid (EDTA), acetic acid, citric acid, or any other acid and base.

In some embodiments, release time control material comprise albumin, carbomers, carboxymethyl cellulose, carrageenan, chitosan, dextrin, polyethylene glycol, polyvinylpyrrolidone, or polyvinyl alcohol.

In some embodiments, chemicals with certain concentration is coated on the plate and dissolved into the blood to achieve a uniform distribution of red blood cell in device.

In some embodiments, a certain concentration is coated on the plate and dissolved into the blood to lyse the red blood cell in the device, wherein the coating can be on first plate, or second plate, or both.

In some embodiments, the chemicals coated in the device include Surfactant, Zwittergent, ASB-14, ASB-16, CHAPS, Cationic surfactant NN-[Tris(hydroxymethyl) methyl]-N-alkyl-N,N-dimethyl ammonium chloride (IIa), IIb, IIc, IId, CTAC, TWEEN® 20, TWEEN® 40, TWEEN® 60, TWEEN® 80, Sodium lauryl sulfate (SLS), ammonium lauryl sulfate, CTAB, sodium lauryl ether sulfate (SLES), sodium myreth sulfate, docusate, perfluorooctanesulfonate, alkyl-aryl ether phosphates, alkyl ether phosphates, CTAB, cetylpyridinium chloride (CPC), benzalkonium chloride (BAC), benzethonium chloride (BZT), dimethyldioctadecylammonium chloride, dioctadecyldimethlyammonium bromide (DODAB), cocamidopropyl hydroxysultaine, cocamidopropyl betaine, narrow-range ethoxylate, octaethylene glycol monododecyl ether, pentaethylene glycol monododecyl ether, nonxynols, TRITON X-100™, polyethoxylated tallow amine, cocamide monoethanolamine, cocamide diethanolamine, poloxamers, glycerol monostearate, glycerol monolaurate, sorbitan monolaurate, sorbitan monostearate, sorbitan tristearate, decyl glucoside, lauryl glucoside, octyl glucoside, lauryldimethylamine oxide, dimethyl sulfoxide, or phosphine oxide.

In some embodiments, the reagent causing red blood cell lysis coated in the device including but not limit to non-ionic copolymer surfactant Pluronic™ F-127, polyoxyl 35 castor oil (Cremophor EL), polyoxyethylene-polyoxypropylene block copolymer (Pluronic™ F-68), polyoxyethylene (40) stearate (Myrj 52), polyoxyethylene lauryl ether (Brij 35), sodium oleate, sodium dodecyl sulfate, TWEEN® 20, TWEEN® 40, TWEEN® 60, TWEEN® 80, SLS, CTAB, CTAC, Tamoxifen, saponin, hydrochloric acid, sulfuric acid, nitric acid, phosphoric acid, lactic acid, 3-[N,N-Dimethyl (3-myristoylaminopropyl)ammonio]propanesulfonate (ABS-14), 3-[N,N-Dimethyl(3-palmitoylaminopropyl)ammonio]-propanesulfonate (ABS-16), anti-malaria drugs (quinine compounds), arsenic, dapsone, metals (chromium/chromates, platinum salts, nickel compounds, copper, lead, cis-platinum), nitrites, nitrofurantoin, penicillin, phenazopyridine (pyridium), rho immune globulin, ribavirin, sulfonamides, sulfones.

In some embodiments, the anticoagulant coated in the device including but not limit to EDTA such as dipotassium ethylenediaminetetraacetic acid (K2EDTA), tripotassium ethylenediaminetetraacetic (K3EDTA), coumarins (vitamin K antagonists), warfarin (coumadin), acenocoumarol, phenprocoumon, atromentin, phenindione, heparin, fondaparinux and idraparinux, dabigatran, rivaroxaban, apixaban, edoxaban, betrixaban, NOACs, hirudin, lepirudin, bivalirudin, agratroban, dabigatran, batroxobin, hementin, Vitamin E, sodium citrate, acid citrate dextrose, oxalate such as fluoride oxalate, deltaparin, desirudin, enoxaparin.

In some embodiments, to achieve a uniform distribution of red blood cell in device, Zwittergent is coated on the plate with a preferred area concentration of 3 ng/mm$^2$, 5 ng/mm$^2$, 8 ng/mm$^2$, 12 ng/mm$^2$, 15 ng/mm$^2$, 25 ng/mm$^2$, 35 ng/mm$^2$, 50 ng/mm$^2$, 80 ng/mm$^2$, 100 ng/mm$^2$ or in a range between any of the two values.

In some embodiments, to lyse red blood cell in device, Zwittergent is coated on the plate with a preferred area concentration of 100 ng/mm$^2$, 120 ng/mm$^2$, 150 ng/mm$^2$, 180 ng/mm$^2$, 200 ng/mm$^2$, 300 ng/mm$^2$, 400 ng/mm$^2$, 500 ng/mm$^2$, 800 ng/mm$^2$, 1000 ng/mm$^2$ or in a range between any of the two values.

In some embodiments, to achieve a uniform distribution of red blood cell in device, Zwittergent is coated on the plate with a preferred final concentration in blood of 0.05 mg/mL, 0.1 mg/mL, 0.2 mg/mL, 0.3 mg/mL, 0.5 mg/mL, 0.6 mg/mL, 1.0 mg/mL, 2 mg/mL or in a range between any of the two values.

In some embodiments, to lyse red blood cell in device, Zwittergent is coated on the plate with a preferred final concentration in blood of 2 mg/mL, 3 mg/mL, 4 mg/mL, 5 mg/mL, 6 mg/mL, 7 mg/mL, 9 mg/mL, 10 mg/mL, 15 mg/mL, 25 mg/mL, 50 mg/mL, or in a range between any of the two values.

In some embodiments, to achieve a uniform distribution of red blood cell in device, Zwittergent is coated on the plate with a preferred area concentration of 3 ng/mm$^2$, 5 ng/mm$^2$, 8 ng/mm$^2$, 12 ng/mm$^2$, 15 ng/mm$^2$, 25 ng/mm$^2$, 35 ng/mm$^2$, 50 ng/mm$^2$, 80 ng/mm$^2$, 100 ng/mm$^2$ or in a range between any of the two values.

In some embodiments, to lyse red blood cell in device, Zwittergent is coated on the plate with a preferred area concentration of 100 ng/mm$^2$, 120 ng/mm$^2$, 150 ng/mm$^2$, 180 ng/mm$^2$, 200 ng/mm$^2$, 300 ng/mm$^2$, 400 ng/mm$^2$, 500 ng/mm$^2$, 800 ng/mm$^2$, 1000 ng/mm$^2$ or in a range between any of the two values.

In some embodiments, to achieve a uniform distribution of red blood cell in device, Zwittergent is coated on the plate with a preferred final concentration in blood of 0.05 mg/mL, 0.1 mg/mL, 0.2 mg/mL, 0.3 mg/mL, 0.5 mg/mL, 0.6 mg/mL, 1.0 mg/mL, 2 mg/mL or in a range between any of the two values.

In some embodiments, to lyse red blood cell in device, Zwittergent is coated on the plate with a preferred final concentration in blood of 2 mg/mL, 3 mg/mL, 4 mg/mL, 5 mg/mL, 6 mg/mL, 7 mg/mL, 9 mg/mL, 10 mg/mL, 15 mg/mL, 25 mg/mL, 50 mg/mL, or in a range between any of the two values.

In some embodiments, the acridine orange is coated on the plate with an area concentration of 0.5 ng/mm$^2$, 1 ng/mm$^2$, 2 ng/mm$^2$, 3 ng/mm$^2$, 5 ng/mm$^2$, 8 ng/mm$^2$, 10 ng/mm$^2$, 15 ng/mm$^2$, 20 ng/mm$^2$, 30 ng/mm$^2$ or in a range between any of the two values.

In some embodiments, the acridine orange is coated on the plate with an area concentration of 3 to 10 ng/mm$^2$ and Zwittergent is coated on the plate with an area concentration of 3 to 10 ng/mm$^2$.

In some embodiments, the acridine orange is coated on the plate with an area concentration of 5 to 20 ng/mm$^2$ and Zwittergent is coated on the plate with an area concentration of 10 to 30 ng/mm$^2$.

In some embodiments, the label is immunoassay antibody label, RNA label, staining dye) is coated on the plate with a preferred final concentration in sample of 0.1 nM/mL, 0.5 nM/mL, 1 nM/mL, 5 nM/mL, 10 nM/mL, 15 nM/mL, 20 nM/mL, 50 nM/mL, or in a range between any of the two values.

In some embodiments, the label is immunoassay antibody label, RNA label, staining dye) is coated on the plate with a preferred final concentration in sample of 1 nM/mL, 5 nM/mL, 10 nM/mL, 15 nM/mL, 20 nM/mL, or in a range between any of the two values.

In some embodiments, the label is immunoassay antibody label, RNA label, staining dye) is coated on the plate with a preferred final concentration in sample of 0.1 uM/mL, 0.5 uM/mL, 1 uM/mL, 5 uM/mL, 10 uM/mL, 15 uM/mL, 20 uM/mL, 50 uM/mL, or in a range between any of the two values.

In some embodiments, the label is immunoassay antibody label, RNA label, staining dye) is coated on the plate with a preferred final concentration in sample of 0.1 ng/mL, 0.5 ng/mL, 1.0 ng/mL, 1.5 ng/mL, 2.0 ng/mL, 5 ng/mL, 10 ng/mL, 50 ng/mL, or in a range between any of the two values.

In some embodiments, the label is immunoassay antibody label, RNA label, staining dye) is coated on the plate with a preferred final concentration in sample of 0.05 mg/mL, 0.15 mg/mL, 0.3 mg/mL, 0.5 mg/mL, 1.0 mg/mL, or in a range between any of the two values.

In some embodiments, the label is immunoassay antibody label, RNA label, staining dye) is coated on the plate with a preferred final concentration in sample of 0.1 mg/mL, 0.5 mg/mL, 1.0 mg/mL, 1.5 mg/mL, 2.0 mg/mL, 5 mg/mL, 10 mg/mL, 50 mg/mL, or in a range between any of the two values.

In some embodiments, the label is immunoassay antibody label, RNA label, staining dye) is coated on the plate with a preferred final concentration in sample of 100 mg/mL, 200 mg/mL, 300 mg/mL, or in a range between any of the two values.

In some embodiments, the thickness of the sample is 1 um, 2 um, 3 um, 5 um, 10 um, 20 um, 30 um, 50 um, 100 um, 150 um or in a range between any of the two values.

In some embodiments, the preferred thickness of the sample is 2 um, 3 um, 5 um, 10 um, 30 um, or in a range between any of the two values.

In some embodiments, the concentration of probe in the sample is 1 nM, 5 nM, 10 nM, 50 nM, 100 nM, 500 nM, 1 uM, 10 nM, 50 nM, 100 nM or in a range between any of the two values.

In some embodiments, the preferred concentration of probe in the sample is 10 nM, 50 nM, 100 nM, 500 nM, 1 uM, or in a range between any of the two values.

In some embodiments, the concentration of enhancer in the sample is 10 nM, 50 nM, 100 nM, 500 nM, 1 uM, 2 uM, 5 uM, 10 uM, 20 uM, 50 uM, 100 uM, 500 uM, or in a range between any of the two values.

In some embodiments, the preferred concentration of enhancer in the sample is 1 uM, 2 uM, 5 uM, 10 uM, 20 uM, 50 uM, or in a range between any of the two values.

In some embodiments, the optical enhancer's light wavelength and the probe's light wavelength is within 1 nm, 5 nm, 10 nm, 20 nm, 50 nm, 100 nm, 150 nm or in a range between any of the two values.

In some embodiments, the optical enhancer's light wavelength and the probe's light wavelength is preferred within 1 nm, 2 nm, 5 nm, 10 nm, 20 nm, 50 nm, or in a range between any of the two values.

In some embodiments, the spacers are fixed on a plate by directly embossing the plate or injection molding of the plate.

In some embodiments, the materials of the plate and the spacers are selected from polystyrene, PMMA, PC, COC, COP, and another plastic.

In some embodiments, the inter-spacer distance is in the range of 1 um to 200 um.

In some embodiments, the inter-spacer distance is in the range of 200 um to 1000 um.

In some embodiments, the spacers regulating the layer of uniform thickness have a filling factor of at least 1%, wherein the filling factor is the ratio of the spacer area in contact with the layer of uniform thickness to the total plate area in contact with the layer of uniform thickness.

In some embodiments, for spacers regulating the layer of uniform thickness, the Young's modulus of the spacers times the filling factor of the spacers is equal to or larger than 10 MPa, wherein the filling factor is the ratio of the spacer area in contact with the layer of uniform thickness to the total plate area in contact with the layer of uniform thickness.

In some embodiments, for a flexible plate, the thickness of the flexible plate times the Young's modulus of the flexible plate is in the range 60 to 750 GPa-um.

In some embodiments, for a flexible plate, the fourth power of the inter-spacer distance (ISD) divided by the thickness of the flexible plate (h) and the Young's modulus (E) of the flexible plate, $ISD^4/(hE)$, is equal to or less than $10^6$ um$^3$/GPa.

In some embodiments, one or both plates comprises a location marker, either on a surface of or inside the plate, that provides information of a location of the plate.

In some embodiments, one or both plates comprises a scale marker, either on a surface of or inside the plate, that provides information of a lateral dimension of a structure of the sample and/or the plate.

In some embodiments, one or both plates comprises an imaging marker, either on surface of or inside the plate, that assists imaging of the sample.

In some embodiments, the spacers function as a location marker, a scale marker, an imaging marker, or any combination thereof.

In some embodiments, the average thickness of the layer of uniform thickness is about equal to a minimum dimension of the analyte in the sample.

In some embodiments, the inter-spacer distance is in the range of 1 um to 50 um.

In some embodiments, the inter-spacer distance is in the range of 50 um to 120 um.

In some embodiments, the inter-spacer distance is in the range of 120 um to 200 um.

In some embodiments, the inter-spacer distance is substantially periodic.

In some embodiments, the spacers are pillars with a cross-sectional shape selected from round, polygonal, circular, square, rectangular, oval, elliptical, and any combination of the same.

In some embodiments, the spacers have a pillar shape and have a substantially flat top surface, wherein, for each spacer, the ratio of the lateral dimension of the spacer to its height is at least 1.

In some embodiments, for each spacer, the ratio of the lateral dimension of the spacer to its height is at least 1.

In some embodiments, wherein a minimum lateral dimension of the spacer is less than or substantially equal to the minimum dimension of the analyte in the sample.

In some embodiments, a minimum lateral dimension of the spacer is in the range of 0.5 um to 100 um.

In some embodiments, a minimum lateral dimension of the spacer is in the range of 0.5 um to 10 um.

In some embodiments, the spacers have a density of at least 100/mm$^2$.

In some embodiments, the spacers have a density of at least 1000/mm$^2$.

In some embodiments, at least one of the plates is transparent.

In some embodiments, at least one of the plates is made from a flexible polymer.

In some embodiments, for a pressure that compresses the plates, the spacers are not compressible and/or, independently, only one of the plates is flexible.

In some embodiments, the flexible plate has a thickness in the range of 10 um to 200 um.

In some embodiments, the variation is less than 30%.

In some embodiments, the variation is less than 10%.

In some embodiments, the variation is less than 5%.

In some embodiments, the collection and cover plates are connected and are configured to be changed from the open configuration to the closed configuration by folding the plates.

In some embodiments, the collection and cover plates are connected by a hinge and are configured to be changed from the open configuration to the closed configuration by folding the plates along the hinge.

In some embodiments, the collection and cover plates are connected by a hinge that is a separate material to the plates, and are configured to be changed from the open configuration to the closed configuration by folding the plates along the hinge.

In some embodiments, the collection and cover plates are made in a single piece of material and are configured to be changed from the open configuration to the closed configuration by folding the plates.

In some embodiments, the device is configured to analyze the sample in 60 seconds or less.

In some embodiments, at the closed configuration, the final sample thickness device is configured to analyze the sample in 60 seconds or less.

In some embodiments, the collection or cover plate further comprises, on its surface, a first predetermined assay site and a second predetermined assay site, wherein the distance between the edges of the assay site is substantially larger than the thickness of the uniform thickness layer when the plates are in the closed position, wherein at least a part of the uniform thickness layer is over the predetermined assay sites, and wherein the sample has one or a plurality of analytes that are capable of diffusing in the sample.

In some embodiments, the collection or cover plate has, on its surface, at least three analyte assay sites, and the distance between the edges of any two neighboring assay sites is substantially larger than the thickness of the uniform thickness layer when the plates are in the closed position, wherein at least a part of the uniform thickness layer is over the assay sites, and wherein the sample has one or a plurality of analytes that are capable of diffusing in the sample.

In some embodiments, the collection or cover plate has, on its surface, at least two neighboring analyte assay sites that are not separated by a distance that is substantially larger than the thickness of the uniform thickness layer when the plates are in the closed position, wherein at least a part of the uniform thickness layer is over the assay sites, and wherein the sample has one or a plurality of analytes that are capable of diffusing in the sample.

In some embodiments, the present invention provides a system for rapidly analyzing a vapor condensation sample using a mobile phone comprising: (a) a device of claim 1; and (b) a mobile communication device comprising: i. one or a plurality of cameras for the detecting signal and/or imaging the vapor condensate sample; and ii. electronics, signal processors, hardware and software for receiving and/or processing the detected signal and/or the image of the vapor condensate sample and for remote communication.

In some embodiments, the system further comprises a light source from either the mobile communication device or an external source.

In some embodiments, one of the plates has a binding site that binds the analyte, wherein at least part of the uniform sample thickness layer is over the binding site and is substantially less than the average lateral linear dimension of the binding site.

In some embodiments, the present invention further comprises: (d) a housing configured to hold the sample and to be mounted to the mobile communication device.

In some embodiments, the housing comprises optics for facilitating the imaging and/or signal processing of the sample by the mobile communication device, and a mount configured to hold the optics on the mobile communication device.

In some embodiments, an element of the optics in the housing is movable relative to the housing.

In some embodiments, the mobile communication device is configured to communicate test results to a medical professional, a medical facility or an insurance company.

In some embodiments, the mobile communication device is further configured to communicate information on the test and the subject with the medical professional, medical facility or insurance company.

In some embodiments, the mobile communication device is further configured to communicate information of the test to a cloud network, and the cloud network is configured to process the information to refine the test results.

In some embodiments, the mobile communication device is further configured to communicate information of the test and the subject to a cloud network, the cloud network is configured to process the information to refine the test results, and the refined test results will send back the subject.

In some embodiments, the mobile communication device is configured to receive a prescription, diagnosis or a recommendation from a medical professional.

In some embodiments, the spacers have a predetermined substantially uniform height and a predetermined constant inter-spacer distance and wherein at least one of the spacers is inside the sample contact area; In some embodiments, the optical signal from the optical enhancer is equal or less than the optical signal from the area of the sample layer that does not contain a target cell.

In some embodiments, before depositing the sample between the two plates, the detection agent and the optical enhancer are coated on the inner surface of the plates.

In some embodiments, before depositing the sample between the two plates, the detection agent and the optical enhancer are coated on the inner surface of the plates.

In some embodiments, the layer thickness of the at least a part of the sample is configured so that the time for the detection agent and the optical enhancer is 30 secs or less.

In some embodiments, the layer thickness of the at least a part of the sample is configured so that the time for the detection agent and the optical enhancer is 60 secs or less.

In some embodiments, the layer thickness of the at least a part of the sample is configured so that the time for the detection agent and the optical enhancer is 120 secs or less.

In some embodiments, the attachment of the optical enhancer to the target cell is specific.

In some embodiments, the attachment of the optical enhancer to the target cell is nonspecific.

In some embodiments, the attachment of the optical enhancer to the target cell is nonspecific, wherein the nonspecific attachment is binding of nucleic acids of the target cell.

In some embodiments, the thin layer thickness is configured so that for a given concentration of the cell in the sample, each individual cell does not substantially overlap with other cells in the imaging.

In some embodiments, further comprising an optical enhancer that binds to the cell and is capable of emit lighting in a wavelength that overlaps with or within a 30 nm from the wavelength of the light emitted by the detection probe.

BRIEF DESCRIPTION OF THE DRAWINGS

The skilled artisan will understand that the drawings, described below, are for illustration purposes only. The drawings are not intended to limit the scope of the present teachings in any way. In some Figures, the drawings are in scale. In the figures that present experimental data points, the lines that connect the data points are for guiding a viewing of the data only and have no other means.

DETAILED DESCRIPTION OF EXEMPLARY EMBODIMENTS

Figure 1:
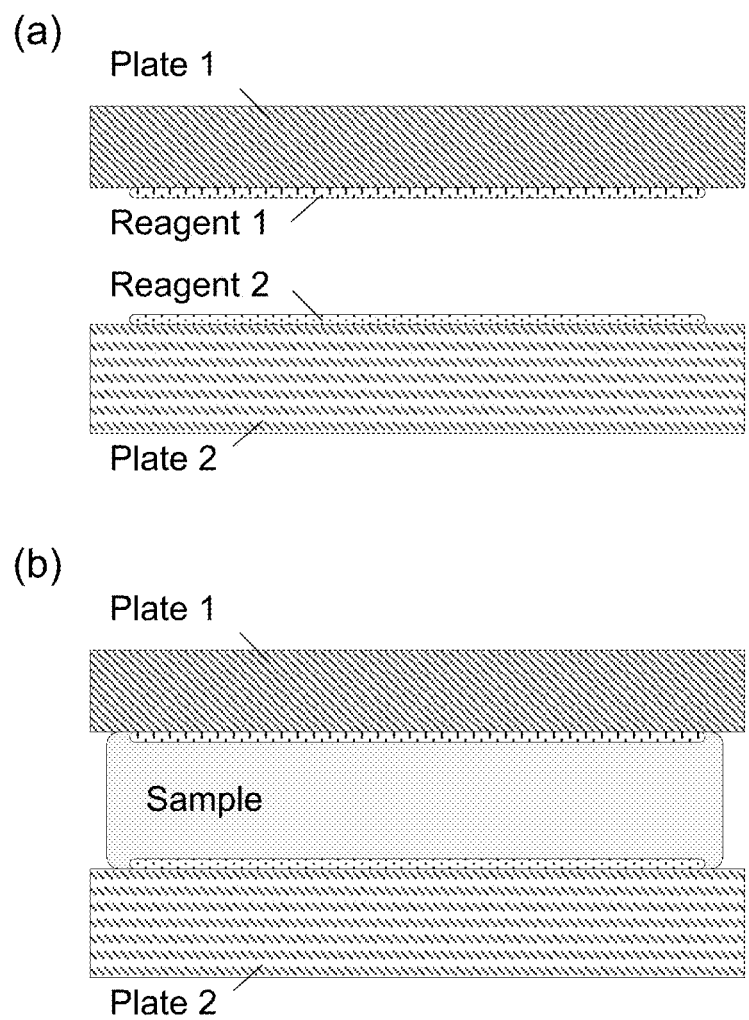
FIG. 1 shows an embodiment of a QMAX (Q: quantification; M: magnifying; A: adding reagents; X: acceleration; also known as compressed regulated open flow (CROF)) device, which comprises a first plate and a second plate. Panel (a) shows the sectional view of the device without samples, two plates are separated with a gap and two reagents (1 and 2) are coated on two plates; panel (b) shows the sectional view of the QMAX device with samples between the two plates.
Figure 2:
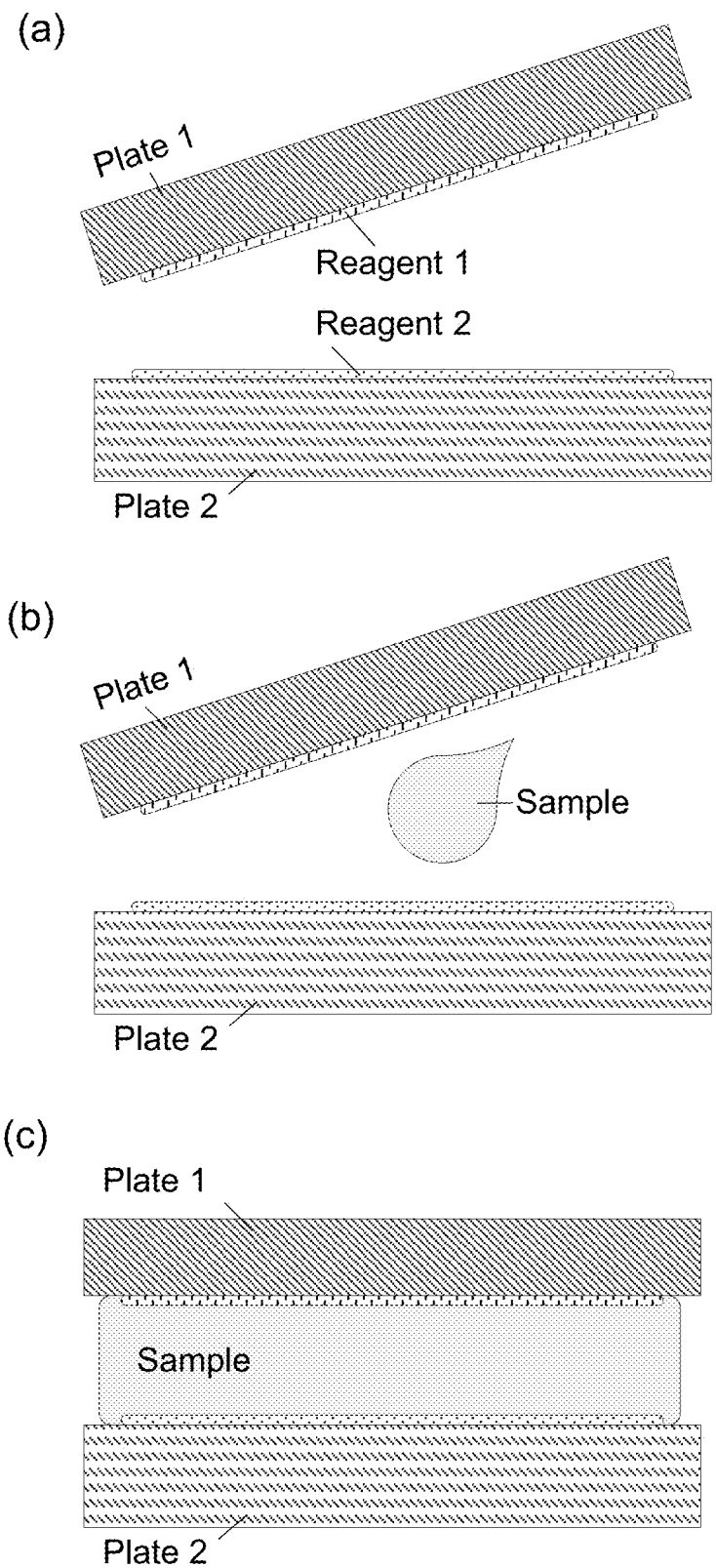
FIG. 2 shows an embodiment of a QMAX device, which comprises a first plate and a second plate. Panel (a) shows the sectional view of the plates in an open configuration when the plates are separated apart, two reagents (1 and 2) are coated on two plates; panel (b) shows the sectional view of depositing a sample on one of the plates at the open configuration; panel (c) shows the perspective view of the QMAX device in a closed configuration with samples between the two plates.

The following detailed description illustrates some embodiments of the invention by way of example and not by way of limitation. If any, the section headings and any subtitles used herein are for organizational purposes only and are not to be construed as limiting the subject matter described in any way. The contents under a section heading and/or subtitle are not limited to the section heading and/or subtitle, but apply to the entire description of the present invention.

The citation of any publication is for its disclosure prior to the filing date and should not be construed as an admission that the present claims are not entitled to antedate such publication by virtue of prior invention. Further, the dates of publication provided can be different from the actual publication dates which can need to be independently confirmed.

It should be noted that the Figures do not intend to show the elements in strict proportion. For clarity purposes, some elements are enlarged when illustrated in the Figures. The dimensions of the elements should be delineated from the descriptions herein provided and incorporated by reference.

The term "optical enhancer" and "enhancer" are interchangeable.

The term "cell' and "target cell" are interchangeable.

Conventionally, staining an analyte on a cell or inside cell membrane for imaging is multiple step process (~10 steps) often taking hours to do. One aspect of the present invention is to immunochemically stain a cell or a tissue in less than 60 seconds without washing. In some embodiments, the present invention stains and observers analyte (protein or nucleic acid) inside a cell in 60 seconds without wash.
Examples of Enhancing Detection of Specifically Stained Cell Using Optical Enhancers FIG. 1 to 4 illustrate several embodiments of the present invention in stain a cell or a tissue rapidly without washing.

In some embodiments, a method of enhancing a homogenous detection of an analyte in a cell that is in a sample, comprising:

(a) having a first plate and a second plate, each has a sample contact area on its surface, wherein the sample contact surfaces contact a sample comprising a cell that contains or is suspected of containing an analyte,
(b) having a detection probe that specifically binds the analyte and is capable of emitting a light at a wavelength, wherein the detection probe diffuses in the sample; (c) having an optical enhancer that binds to the cell and is capable of emit lighting in a wavelength that overlaps with or within a 30 nm from the wavelength of the light emitted by the detection probe;
(d) sandwiching the sample, the detection probe, and the optical enhancer between the two sample contact areas of the two plates to form a thin layer of a thickness of 200 microns (um) or less; and
(e) imaging using an imager, after the step (d) and without using any washing step, the thin layer to detect the cell that has the analyte bound to the detection probe; wherein the thin layer sample thickness is configured so that for a given concentration of the cell in the sample, each individual cell does not substantially overlap other cells in the imaging;
wherein the thickness of the thin layer, the concentration of the detection probe in the sample, or the concentration of the optical enhancer in the sample is configured to make, in the step (e) of imaging, in the thin layer, the location having the bound detection probe is distinguishable from the locations not having the bound detection probe, wherein the bound detection probe is the detection probe bound to the analyte in the cell.

In some embodiments, a method of enhancing a homogenous detection of an analyte in a cell that is in a sample, comprising:

(a) having a first plate and a second plate, each has a sample contact area on its surface, wherein the sample contact surfaces contact a sample comprising a cell that contains or is suspected of containing an analyte,
(b) depositing, on at least one of the sample contact areas, a detection probe that specifically binds the analyte and emits a light at a wavelength, wherein the detection probe diffuses in the sample;
(c) having an optical enhancer that binds to the cell and emits light in a wavelength range that overlaps with or within a 30 nm from the wavelength of the light emitted by the detection probe;
(d) sandwiching the sample, the detection probe, and the optical enhancer between the two sample contact areas of the two plates to form a thin layer, wherein the thin layer has a thickness of 150 microns (um) or less; and
(e) imaging using an imager, after the step (d) and without using any washing step, the thin layer to detect the detection probe that has specifically bound to the analyte; wherein the thin layer sample thickness is configured so that for a given concentration of the cell in the sample, each individual cell does not substantially overlap other cells in the imaging;
wherein the thickness of the thin layer, the concentration of the detection probe in the sample, or the concentration of the optical enhancer in the sample is configured to make, in the step (e) of imaging, in the thin layer, the location having the bound detection probe is distinguishable from the locations not having the bound detection probe, wherein the bound detection probe is the detection probe bound to the analyte in the cell.

In some embodiments, a method of enhancing a homogenous detection of an analyte in a cell that is in a sample, comprising:

(a) having a first plate and a second plate, each has a sample contact area on its surface, wherein the sample contact surfaces contact a sample comprising a cell that contains or is suspected of containing an analyte, (b) depositing, on at least one of the sample contact areas, a detection probe that specifically binds the analyte and emits a light at a wavelength, wherein the detection probe diffuses in the sample;

(c) depositing, on at least one of the sample contact areas, an optical enhancer that binds to the cell and emits light in a wavelength range that overlaps with or within a 30 nm from the wavelength of the light emitted by the detection probe, wherein the optical enhancer diffuses in the sample;

(d) sandwiching the sample, the detection probe, and the optical enhancer between the two sample contact areas of the two plates to form a thin layer, wherein the thin layer has a thickness of 150 microns (um) or less; and (e) imaging using an imager, after the step (d) and without using any washing step, the thin layer to detect the detection probe that has specifically bound to the analyte; wherein the thin layer sample thickness is configured so that for a given concentration of the cell in the sample, each individual cell does not substantially overlap other cells in the imaging;

wherein the thickness of the thin layer, the concentration of the detection probe in the sample, or the concentration of the optical enhancer in the sample is configured to make, in the step (e) of imaging, in the thin layer, the location having the bound detection probe is distinguishable from the locations not having the bound detection probe, wherein the bound detection probe is the detection probe bound to the analyte in the cell.

In some embodiments, a kit for enhancing a homogenous detection of an analyte in a cell that is in a sample, comprising:

(a) a first plate and a second plate, each has a sample contact area on its surface, wherein the sample contact surfaces contact a sample comprising a cell that contains or is suspected of containing an analyte, (b) a detection probe that specifically binds the analyte and is capable of emitting a light at a wavelength, wherein the detection probe diffuses in the sample;

(c) an optical enhancer that binds to the cell and emits lighting in a wavelength that overlaps with or within 30 nm from the wavelength of the light emitted by the detection probe;

wherein the first and second plates are configured to sandwich the sample, the detection probe, and the optical enhancer between the two sample contact areas to form a thin layer of a thickness of 200 microns (um) or less; and wherein the thin layer sample thickness is configured so that for a given concentration of the cell in the sample, each individual cell does not substantially overlap other cells in the imaging;

wherein the thickness of the thin layer, the concentration of the detection probe in the sample, or the concentration of the optical enhancer in the sample is configured to make, in the step (e) of imaging, in the thin layer, the location having the bound detection probe is distinguishable from the locations not having the bound detection probe, wherein the bound detection probe is the detection probe bound to the analyte in the cell.

In some embodiments, a device of enhancing a homogenous detection of an analyte in a cell that is in a sample, comprising:

(a) a first plate and a second plate, each has a sample contact area on its surface, wherein the sample contact surfaces contact a sample comprising a cell that contains or is suspected of containing an analyte, (b) a detection probe that specifically binds the analyte and emits a light at a wavelength, wherein the detection probe is coated on at least one of the sample contact areas and diffuses in the sample;

(c) an optical enhancer that binds to the cell and emits light in a wavelength range that overlaps with or within a 30 nm from the wavelength of the light emitted by the detection probe;

(d) the sample contact areas in the first and second plates faces each other and sandwich the sample, the detection probe, and the optical enhancer between the two sample contact areas of the two plates to form a thin layer, wherein the thin layer has a thickness of 150 microns (um) or less; and (e) an imager that images the thin layer to detect the detection probe that has specifically bound to the analyte;

wherein the thin layer sample thickness is configured so that for a given concentration of the cell in the sample, each individual cell does not substantially overlap other cells in the imaging;

wherein the thickness of the thin layer, the concentration of the detection probe in the sample, or the concentration of the optical enhancer in the sample is configured to make, in the step (e) of imaging, in the thin layer, the location having the bound detection probe is distinguishable from the locations not having the bound detection probe, wherein the bound detection probe is the detection probe bound to the analyte in the cell.

In some embodiments, a method of enhancing a homogenous detection of an analyte in a cell that is in a sample, comprising:

(a) a first plate and a second plate, each has a sample contact area on its surface, wherein the sample contact surfaces contact a sample comprising a cell that contains or is suspected of containing an analyte, (b) a detection probe that specifically binds the analyte and emits a light at a wavelength, wherein the detection probe is coated on one or both of the sample contact areas and diffuses in the sample;

(c) an optical enhancer that binds to the cell and emits light in a wavelength range that overlaps with or within a 30 nm from the wavelength of the light emitted by the detection probe, wherein the optical enhancer is coated on one or both of the sample contact areas and diffuses in the sample;

(d) the sample contact areas in the first and second plates faces each other and sandwich the sample, the detection probe, and the optical enhancer between the two sample contact areas of the two plates to form a thin layer, wherein the thin layer has a thickness of 150 microns (um) or less; and (e) imaging using an imager, after the step (d) and without using any washing step, the thin layer to detect the detection probe that has specifically bound to the analyte; wherein the thin layer sample thickness is configured so that for a given concentration of the cell in the sample, each individual cell does not substantially overlap other cells in the imaging;

wherein the thickness of the thin layer, the concentration of the detection probe in the sample, or the concentration of the optical enhancer in the sample is configured to make, in the step (e) of imaging, in the thin layer, the location having the bound detection probe is distinguishable from the locations not having the bound detection probe, wherein the bound detection probe is the detection probe bound to the analyte in the cell.

In some embodiments, a system of enhancing a homogenous detection of an analyte in a cell that is in a sample, comprising:
(a) a device or a kit of any prior claims; and
(b) a communication device, In some embodiments, a method for a rapid homogenous detection of an analyte inside a membrane of a cell in a sample, comprising:
(a) having a first plate and a second plate, each has a sample contact area on its surface, wherein the sample contact surfaces contact a sample comprising a cell that contains or is suspected of containing an analyte inside of the cell membrane,
(b) having a detection probe that specifically binds the analyte and is capable of emitting a light at a wavelength, wherein the detection probe diffuses in the sample;
(c) having a permeabilization agent that makes a membrane of the cell permeable to the detection probe;
(d) sandwiching the sample, the detection probe, and the permeabilization agent between the two sample contact areas of the two plates to form a thin layer of a thickness of 200 microns (um) or less; and
(e) imaging, after the step (d) and without a washing step, the thin layer to detect the cell that has the analyte bound to the detection probe;
wherein the thin layer sample thickness is configured so that for a given concentration of the cell in the sample, each individual cell does not substantially overlap other cells in the imaging;
wherein the thickness of the thin layer and the concentration of the detection probe in the sample, are configured to make, in the thin layer, the location having the detection probe that bound to the analyte inside the cell membrane is distinguishable from the locations that do not have the cell; and
wherein the washing step is a step of removing unbound detection probe, permeabilization reagent, or both from the sample contact areas.

In some embodiments, a method for a rapid homogenous detection of an analyte inside a membrane of a cell in a sample, comprising:
(a) having a first plate and a second plate, each has a sample contact area on its surface, wherein the sample contact surfaces contact a sample comprising a cell that contains or is suspected of containing an analyte,
(b) depositing, on at least one of the sample contact areas, a detection probe that specifically binds the analyte and emits a light at a wavelength, wherein the detection probe diffuses in the sample;
(c) having a permeabilization agent that makes a membrane of the cell permeable to the detection probe;
(d) sandwiching the sample, the detection probe, and the optical enhancer between the two sample contact areas of the two plates to form a thin layer, wherein the thin layer has a thickness of 150 microns (um) or less; and
(e) imaging using an imager, after the step (d) and without using any washing step, the thin layer to detect the detection probe that has specifically bound to the analyte;
wherein the thin layer sample thickness is configured so that for a given concentration of the cell in the sample, each individual cell does not substantially overlap other cells in the imaging;
wherein the thickness of the thin layer, the concentration of the detection probe in the sample, or the concentration of the optical enhancer in the sample is configured to make, in the step (e) of imaging, in the thin layer, the location having the bound detection probe is distinguishable from the locations not having the bound detection probe, wherein the bound detection probe is the detection probe bound to the analyte in the cell; and
wherein the washing step is a step of removing unbound detection probe, permeabilization reagent, or both from the sample contact areas.

The method and device of any prior claim, wherein the optical signal from the optical enhancer is equal or less than the optical signal from the area of the sample layer that does not contain a target cell.

The method and device of any prior claim, wherein, before depositing the sample between the two plates, the detection agent and the optical enhancer are coated on the inner surface of the plates.

The method and device of any prior claim, wherein, before depositing the sample between the two plates, the detection agent and the optical enhancer are coated on the inner surface of the plates.

The method and device of any prior claim, wherein the layer thickness of the at least a part of the sample is configured so that the time for the detection agent and the optical enhancer is 30 secs or less.

The method and device of any prior claim, wherein the layer thickness of the at least a part of the sample is configured so that the time for the detection agent and the optical enhancer is 60 secs or less.

The method and device of any prior claim, wherein the layer thickness of the at least a part of the sample is configured so that the time for the detection agent and the optical enhancer is 120 secs or less.

The method and device of any prior claim, wherein the attachment of the optical enhancer to the target cell is specific.

The method and device of any prior claim, wherein the attachment of the optical enhancer to the target cell is nonspecific.

In some embodiments, the reagent is coated with a slow release layer that release the reagent (i.e. stain) at least 3 seconds after a sample in contact the reagent, and in some embodiments, at least 10 seconds, or at least 60 seconds.

Immunostaining

In some embodiments, immunostaining can be used to detect a cell or non-cell analyte within a sample. In some embodiments, immunostaining can be used to detect a cell or non-cell analyte by enhancing signal from the cell or non-cell analyte relative to a background signal. Immunostaining can generally refer to any method that uses one or more antibodies to detect a cell or non-cell analyte within a sample. A naturally occurring antibody can be a protein comprising at least two heavy (H) chains and two light (L) chains inter-connected by disulfide bonds. Each heavy chain can be comprised of a heavy chain variable region ($V_H$) and a heavy chain constant region. The heavy chain constant region can be comprised of three domains, $C_{H1}$, $C_{H2}$ and $C_{H3}$. Each light chain can be comprised of a light chain variable region ($V_L$) and a light chain constant region. The light chain constant region can be comprised of one domain, $C_L$. The $V_H$ and $V_L$ regions can be further subdivided into regions of hypervariability, termed complementary determining regions (CDR), interspersed with regions that are more conserved, termed framework regions (FR). Each $V_H$ and $V_L$ can be composed of three CDRs and four FRs arranged from amino-terminus to carboxy-terminus in the following order: $FR_1$, $CDR_1$, $FR_2$, $CDR_2$, $FR_3$, $CDR_3$, and FR4. The constant regions of the antibodies can mediate the binding of the immunoglobulin to host tissues or factors, including various cells of the immune system (e.g., effector cells) and the first component (C1q) of the classical complement system. The antibodies can be of any isotype (e.g., IgG, IgE, IgM, IgD, IgA and IgY), class (e.g., $IgG_1$, $IgG_2$, $IgG_3$, $IgG_4$, $IgA_1$ and $IgA_2$), subclass or modified version thereof.

Antibodies can include a complete immunoglobulins or fragments thereof. An antibody fragment can refer to one or more fragments of an antibody that retain the ability to specifically bind to a cell or non-cell analyte, such as an antigen. In addition, aggregates, polymers, and conjugates of immunoglobulins or their fragments can be used where appropriate so long as binding affinity for a particular molecule is maintained. Examples of antibody fragments include a Fab fragment, a monovalent fragment consisting of the $V_L$, $V_H$, $C_L$ and $C_{H1}$ domains; a $F(ab)_2$ fragment, a bivalent fragment comprising two Fab fragments linked by a disulfide bridge at the hinge region; an Fd fragment consisting of the $V_H$ and $C_{H1}$ domains; an Fv fragment consisting of the $V_L$ and $V_H$ domains of a single arm of an antibody; a single domain antibody (dAb) fragment, which consists of a $V_H$ domain; and an isolated CDR and a single chain Fragment (scFv) in which the $V_L$ and $V_H$ regions pair to form monovalent molecules (known as single chain Fv (scFv)). Thus, antibody fragments include Fab, $F(ab)_2$, scFv, Fv, dAb, and the like. Although the two domains $V_L$ and $V_H$ are coded for by separate genes, they can be joined, using recombinant methods, by an artificial peptide linker that enables them to be made as a single protein chain. Such single chain antibodies include one or more antigen binding moieties. These antibody fragments can be obtained using conventional techniques known to those of skill in the art, and the fragments can be screened for utility in the same manner as are intact antibodies. Antibodies can be human, humanized, chimeric, isolated, dog, cat, donkey, sheep, any plant, animal, or mammal.

Figure 3:
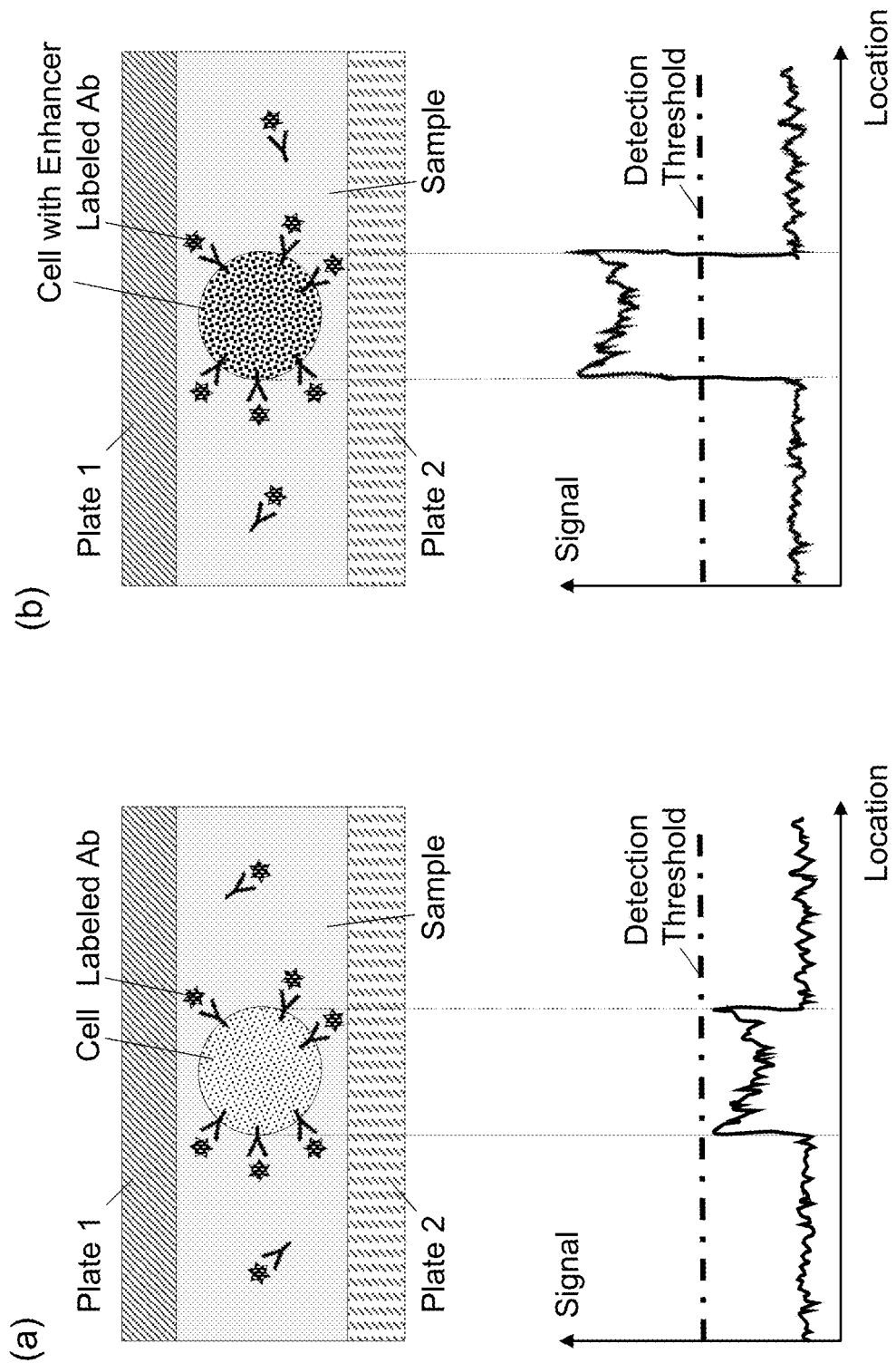
FIG. 3 shows an exemplary effect of using a combination of labeled antibodies and cell enhancer (e.g., non-specific cell dye or other specific antibodies) on signal detection from a cell or non-cell analyte within the sample. (a) shows the cell without enhancer labeled by antibodies has signal lower than the detection threshold; (b) shows the cell with enhancer labeled by antibodies has signal higher than the detection threshold.

In any of the embodiments of the present disclosure, any number and/or type of antibodies can be used. In particular, about 1 antibody, about 2 antibodies, about 3 antibodies, about 4 antibodies, about 5 antibodies, about 10 antibodies, about 25 antibodies, or greater than about 25 antibodies can be used. For example, as shown in FIG. 3, a labeled antibody can be used to detect a cell analyte within a sample. However, as shown in FIG. 3, 2 different labeled antibodies can be used to detect a cell or non-cell analyte (e.g., an antigen) within a sample, thereby enhancing a signal detected from the cell or non-cell analyte relative to a background signal. In some embodiments, two or more antibodies can be used to detect a cell or non-cell analyte, and the two or more antibodies can bind the same molecule. In some embodiments, two or more antibodies can be used to detect a cell or non-cell analyte, and the two or more antibodies can bind the same epitope. In some embodiments, two or more antibodies can be used to detect a cell or non-cell analyte, and the two or more antibodies can bind different epitopes on the same antigen (e.g., polyclonal antibodies). In some embodiments, two or more antibodies can be used to detect a cell or non-cell analyte, and the two or more antibodies can bind the same epitope on different molecules. In some embodiments, two or more antibodies can be used to detect a cell or non-cell analyte, and the two or more antibodies can bind different molecules.

Any antibody used in an embodiment of the present disclosure can be labeled or unlabeled. A label can refer to a molecule that, when attached (directly or indirectly, e.g., via an antibody) to another molecule provides or enhances a means of detecting the other molecule. A signal emitted from a label can allow detection of the molecule or complex to which it is attached, and/or the label itself. A label can be a molecular species that elicits a physical or chemical response that can be observed or detected by the naked eye or by means of instrumentation such as, without limitation, cameras (e.g., mobile phone cameras), scintillation counters, colorimeters, UV spectrophotometers and the like. Labels include but are not limited to, radioactive isotopes, fluorophores, chemiluminescent dyes, chromophores, enzymes, enzymes substrates, enzyme cofactors, enzyme inhibitors, dyes, metal ions, nanoparticles, metal sols, ligands (such as biotin, avidin, streptavidin or haptens) and the like. A fluorescence or fluorescent label or tag emits detectable light at a particular wavelength when excited at a different wavelength. A radiolabel or radioactive tag emits radioactive particles detectable with an instrument such as, without limitation, a scintillation counter. Other signal generation detection methods include: chemiluminescence detection, electrochemiluminescence detection, Raman energy detection, colorimetric detection, hybridization protection assays, and mass spectrometry. Non limiting examples of labels include a fluorophore, a chromophore, FITC, TRITC, DTAF, Texas-Red, phycoerythrin, allophycocyanin, a green fluorescent protein (GFP), a blue fluorescent protein (BFP), rhodamine, FAM, TET, HEX, JOE, TAMRA, ROX, an aromatic-substituted xanthene dye, 4,7-dichloro-fluorescein, 4,7-dichloro-rhodamine, a cyanine dye, an enzyme, horseradish peroxidase (HRP), alkaline phosphatase, beta-galactosidase, luciferase, chloramphenicol acetyltransferase (CAT), avidin, streptavidin, biotin, a biotinylated protein, or any combination, fragments or derivatives thereof. In any embodiments, of the present disclosure, one or more labels can used to detect a cell or non-cell analyte. In any embodiments, of the present disclosure, two or more labels can used to detect a cell or non-cell analyte. In some embodiments, where two or more labels are used to detect a cell or non-cell analyte, the excitation and/or emission spectrum of the two or more labels can be the same. For example, a sample can be contacted with two antibodies (e.g., each of which binds to the same epitope on the same antigen), each having a different label that excites at the same wavelength. In another example, a sample can be contacted with two antibodies (e.g., each of which bind to a different epitope on the same antigen), each having the same label that excites at a predetermined wavelength. In some embodiments, where two or more labels are used to detect a cell or non-cell analyte, the excitation and/or emission spectrum of the two or more labels can be different. In some embodiments, where three or more labels are used to detect a cell or non-cell analyte, the excitation and/or emission spectrum of at least two or more labels can be the same. In some embodiments, where three or more labels are used to detect a cell or non-cell analyte, the excitation and/or emission spectrum of at least two or more labels can be different.

If an antibody comprises a label, the methods of detection can include fluorescence, luminescence, radioactivity, and the like. If the antibody is unlabeled, the detection of binding can be based on a change in some physical property of the target analyte. Such physical properties can include, for example, a refractive index or electrical impedance. The detection of binding of unlabeled antibody could include, for example, mass spectroscopy. In competitive methods, binding-site occupancy can be determined indirectly. In this method, the target cell or non-cell analyte can be exposed to a solution containing a cognate labeled antibody and an unlabeled antibody. The labeled cognate antibody and the unlabeled antibody compete for the binding sites on the target analyte. The affinity of the unlabeled antibody for the target analyte relative to the labeled cognate antibody is determined by the decrease in the amount of binding of the labeled antibody.

Dye Staining

In some embodiments, dye staining can be used to detect a cell or non-cell analyte within a sample. In some embodiments, dye staining can be used to detect a cell or non-cell analyte by enhancing signal from the cell or non-cell analyte relative to a background signal. Dye staining can refer to a technique used to enhance contrast in an image, and specifically enhance a detectable signal from a target cell or non-cell analyte in a sample. Stains and dyes can be used to highlight structures in biological tissues or cells for viewing. Stains can be used to define and examine cell populations (e.g., classifying different blood cells or bacteria, such as gram-positive and gram-negative bacteria), or organelles within individual cells. Dye staining can involve contacting a class-specific (e.g., DNA, protein, lipid, or carbohydrate) dye to a sample to qualify or quantify the presence of a specific cell or non-cell analyte within the sample.

In any of the embodiments of the present disclosure, any number and/or type of dyes can be used. In particular, about 1 dye, about 2 dyes, about 3 dyes, about 4 dyes, about 5 dyes, about 10 dyes, about 25 dyes, or greater than about 25 dyes can be used. In some embodiments, two or more dyes can be used to detect a cell or non-cell analyte, and the two or more dyes can bind the same molecule. In some embodiments, two or more dyes can be used to detect a cell or non-cell analyte, and the two or more dyes can stain the same region (e.g., the same organelle) of the same target cell or non-cell analyte. In some embodiments, two or more dyes can be used to detect a cell or non-cell analyte, and the two or more dyes can stain different regions (e.g., the cell cytoplasm and the cell nucleus) of the same target cell or non-cell analyte.

A signal emitted from a dye can allow detection of the molecule or complex to which it is attached. A dye can be a molecular species that elicits a physical or chemical response that can be observed or detected by the naked eye or by means of instrumentation such as, without limitation, cameras (e.g., mobile phone cameras), scintillation counters, colorimeters, UV spectrophotometers and the like. Dyes can include, but are not limited to 5-Ethynyl-2'-deoxyuridine, 7-Aminoactinomycin D, Acid fuchsin, Acridine orange, Acridine yellow, Alcian blue stain, Aniline Blue WS, Aniline Yellow, Auramine O, Bismarck brown Y, Brilliant green (dye), Bromodeoxyuridine, Calcofluor-white, Carbol fuchsin, Carboxyfluorescein diacetate succinimidyl ester, Carmine, Congo red, Coomassie Brilliant Blue, Crystal violet, DAPI, DiI, DiOC6, Eosin, Ethidium bromide, Ethyl Green, Fast Green FCF, Feulgen stain, Fluorescein, Fluorescein isothiocyanate, Fuchsine, GelGreen, GelRed, Giemsa stain, Green S, H&E stain, Haematoxylin, Hematein, Hoechst stain, Janus Green B, Jaswant Singh-Bhattacharji (JSB) stain, Light Green SF, Lugol's iodine, Malachite green, Mallory's trichrome stain, Methyl blue, Methyl violet, Methylene blue, Neutral red, New methylene blue, Nigrosin, Nile blue, Nile red, Oil Blue 35, Oil Red O, Orange G, Orcein, Osmium tetroxide, P-Dimethylaminocin- namaldehyde, Phyloxin, Ponceau 2R, Ponceau 6R, Propidium iodide, Pyranine, Quinoline Yellow SS, Red 2G, Rhodamine, Rhodamine 123, Rhodamine 6G, Rhodamine B, RiboGreen, Ruthenium red, Safranin, Silver nitrate, Staining, Sudan Black B, Sudan Ill, Sudan IV, Sudan Red 7B, SYBR Green I, SYBR Safe, SYTOX, Template: Stains, 1H,5H,11H,15H-Xantheno[2,3,4-ij:5,6,7-ij]diquinolizin-18-ium, 9-[2(or 4)-(chlorosulfonyl)-4(or 2)-sulfophenyl]-2,3,6,7,12,13,16,17-octahydro-, inner salt (TEXAS RED®), Toluidine blue stain, Trypan blue, User: Kyle MoJo/sandbox, Victoria blue BO, Water blue, Wayson stain, and Ziehl-Neelsen stain.

In some embodiments, the dye selected is a metachromatic dye. The term "metachromatic dye" can refer to a fluorescent dye that contains two or more peaks in its emission spectrum when bound to a cell or cellular components. A metachromatic dye can fluoresce at different wavelengths when bound to different types of cells or molecules, e.g., to RNA, DNA, or other cellular components. For example, a metachromatic dye used in any embodiment of the present disclosure fluoresces at different wavelengths when bound to double-stranded DNA, single-stranded DNA, or single-stranded RNA.

A variety of metachromatic dyes are known in the art and include, without limitation, xanthene dyes, carbocyanine dyes, polymethine dyes including Astra Violet FR, thiofalvine T, psuedoisocyanine, oxacarbocyanine dyes, acridine dyes, azine dyes, diphenylmethane dyes, methine dyes, oxazine dyes, cyanine dyes, styryl dyes, nonyl Acridine Orange dye (3,6-Bis-(dimethylamino)-10-nonylacridinium bromide, Molecular Probes, Eugene, Oreg.), the Acridine Red dye, the Toluidine Blue dye (2-amino-7-dimethyl-amino-3-methylphenothiazinium chloride), hydrosystilbamidine, and cyanine dyes including SYTO dyes, TOTO dyes, YOYO dyes, BOBO dyes, and combinations or derivatives thereof.

In some embodiments, the dye can be a non-metachromatic dye. The term "non-metachromatic dye" can refer to a fluorescent dye that provides a single wavelength of excitation when irradiated at a predetermined wavelength. Such dyes are useful in methods for discriminating multiple cell types or in circumstances in which a second fluorescent dye or antibody can be present that has a metachromatic wavelength that interferes with analysis be of the sample. Such dyes can be useful for staining cellular components of cells including acidophilic granules, basophilic granules, and cellular membranes of the cells. Non limiting examples of non-metachromatic dyes include, without limitation, Neutral Red dye (3-amino-7-dimethylamino-2-methylphenazine hydrochloride), Basic Orange 21 dye, DiOC dye (1,1'-dimethyloxacarbocyanine), Pyronin Y dye, Methylene Blue dye (3-bis-(dimethylamino)-phenothiazin-5-ium chloride), Auramine O dye (4,4'-(imidocarbonyl)-bis-(N,N-dimethylaniline) monohydrochloride), LDS 751 dye (quinolinium, 6-(dimethylamino)-2-[4-[4-(dimethylamino)phenyl]-1,3-butadienyl]-2-ethyl perchlorate), Red series dyes, and combinations or derivatives thereof. Still other dyes suitable for use include ethidium bromide, propidium iodide (3,8-Diamino-5-(3-diethylaminopropyl)-6-phenyl-phenanthridinium iodide methiodide), hexidium iodide, dihydroethidium, ethidium monoazide, the Thiazole Orange dye, and combinations and derivatives thereof.

In some embodiments, the reagents coating on the device including an agent making cell membrane or cell nucleus permeable, including but not limit to TRITON X-100™ surfactant, Zwittergent, ASB-14, ASB-16, CHAPS, Cationic surfactant NN-[Tris(hydroxymethyl) methyl]-N-alkyl-N,N- dimethyl ammonium chloride (IIa), IIb, IIc, IId, CTAC, TWEEN® 20, TWEEN® 40, TWEEN® 60, TWEEN® 80, Sodium lauryl sulfate (SLS), ammonium lauryl sulfate, CTAB, sodium lauryl ether sulfate (SLES), sodium myreth sulfate, docusate, perfluorooctanesulfonate, alkyl-aryl ether phosphates, alkyl ether phosphates, CTAB, cetylpyridinium chloride (CPC), benzalkonium chloride (BAC), benzethonium chloride (BZT), dimethyldioctadecylammonium chloride, dioctadecyldimethlyammonium bromide (DODAB), cocamidopropyl hydroxysultaine, cocamidopropyl betaine, narrow-range ethoxylate, octaethylene glycol monododecyl ether, pentaethylene glycol monododecyl ether, nonxynols, TRITON X-100™, polyethoxylated tallow amine, cocamide monoethanolamine, cocamide diethanolamine, poloxamers, glycerol monostearate, glycerol monolaurate, sorbitan monolaurate, sorbitan monostearate, sorbitan tristearate, decyl glucoside, lauryl glucoside, octyl glucoside, lauryldimethylamine oxide, dimethyl sulfoxide, phosphine oxide.

In some embodiments, the reagents coating on the device including an agent making cell membrane or cell nucleus permeable, by method of osmotic pressure difference between the cell membrane as dilution, or tuning salt concentration.

In some embodiments, the reagents coating on the device including an agent making protein cross link, including but not limit to formaldehyde, glutaraldehyde, osmium tetroxide, potassium dichromate and potassium permanganate.

In any of the embodiments of the present disclosure, for gram-positive and negative staining, acridine orange and other SYTO green dyes such as SYTO 9, SYTO 11, SYTO12, SYTO13, SYTO16, SYTO21 and SYTO24 can stain both Gram-positive and Gram-negative bacteria. Fluorescent-labeled wheat germ agglutinin can specifically stain Gram-positive bacteria. Hexidium iodide can specifically stain Gram-positive bacteria. Crystal violet and iodine stain both Gram positive and negative. Decolorization with ethanol and acetone. Counter stain with safranin/carbol fuchsin.

Any dye used in the embodiments of the present disclosure can be a cell permeant dye or cell impermeant dye. The term "cell permeant" can refer a dye that readily penetrates a cell wall and stains the components of the same without requiring the additional presence of a permeabilizing agent. Typically, cell-permeant dyes are utilized to stain live cells or components of cells that have not been lysed. In some embodiments, cell permeant dyes are utilized to analyze samples containing whole blood. In some embodiments of the present disclosure, if a cell impermeant dye is used, a cell permeabilizing agent may be used to enhance permeability of the cell to the dye.

In some embodiments, a dye can be used in combination with a labeled antibody. For example, as shown in FIG. 3, a labeled antibody can be used to detect a cell analyte within a sample. However, as shown in FIG. 3, a labeled antibody in combination with a cell dye can be used to detect a cell or non-cell analyte (e.g., an antigen) within a sample, thereby enhancing a signal detected from the cell or non-cell analyte relative to a background signal. Simple staining can refer to staining with only one stain/dye. There are various kinds of multiple staining, many of which are examples of counterstaining, differential staining, or both, including double staining and triple staining. In any embodiments, of the present disclosure, one or more dyes can used to detect a cell or non-cell analyte. In any embodiments, of the present disclosure, two or more dyes can used to detect a cell or non-cell analyte. In some embodiments, where two or more dyes are used to detect a cell or non-cell analyte, the excitation and/or emission spectrum of the two or more dyes can be the same. For example, a sample can be contacted with two antibodies (e.g., each of which bind to the same epitope on the same antigen), each having a different dye that excites at the same wavelength. In another example, a sample can be contacted with two antibodies (e.g., each of which bind to a different epitope on the same antigen), each having the same dye that excites at a predetermined wavelength. In some embodiments, where two or more dyes are used to detect a cell or non-cell analyte, the excitation and/or emission spectrum of the two or more dyes can be different. In some embodiments, where three or more dyes are used to detect a cell or non-cell analyte, the excitation and/or emission spectrum of at least two or more dyes can be the same. In some embodiments, where three or more dyes are used to detect a cell or non-cell analyte, the excitation and/or emission spectrum of at least two or more dyes can be different.

In any of the embodiments disclosed herein, a labeled antibody, stain, and/or dye can be coated onto one or more surfaces of the first plate and/or the second plate. It is contemplated that, coating a labeled antibody, stain, and/or dye onto one or more surfaces of the first plate or the second plate can be useful in reducing the number of steps performed by the user in order to analyze a sample. For example, if the first plate is coated with a cell staining reagent, the user would simply need to deposit a sample onto or into the QMAX card (e.g., within the sample contact area). Upon contact the cell staining reagent, cells within the sample can be automatically (e.g., without user intervention) stained. A reduction in the number of steps performed by the user can reduce error (e.g., human error), increase accuracy in data analysis, and reduce the amount of time needed to analyze a sample. In some embodiments, stain or dye can be coated on one or more surfaces of a first plate, and a labeled antibody can be coated on one or more surfaces of a second plate. In another embodiment, a labeled antibody and a stain or dye can be coated on one or more surfaces of either the first plate or the second plate. In yet another embodiment, a labeled antibody and a stain or dye can be coated on one or more surfaces of both of the first plate and the second plate.

It is also contemplated that a blocking agent that competes with a stain or dye can be used to enhance signal from a target cell or non-cell analyte. For example, a blocking agent can be used to associate with unbound antibodies, thereby quenching the reporter molecule on the antibody and reducing the background signal that may otherwise be generated by said unbound antibodies. The blocking agent can block non-specific interaction of a dye with the cell or cellular components. The blocking agent can compete with other dyes present for the binding sites on the cells or non-cell analytes being analyzed. The blocking agent can compete with low affinity dyes for specific binding sites on the cells or non-cell analytes. The blocking agent can itself be a dye; in such circumstances, the dye is selected so that it is differentially detectable from the dye or stain that associates with a target cell or non-cell analyte. Alternatively, the blocking agent may be any compound which blocks non-specific interactions of the dye or stain without affecting the specific binding of the dye or stain to its target(s).

A blocking agent is either non-fluorescent, or is selected from among dyes that fluoresce at wavelengths different from the wavelength of the dye(s) used to detect a target cell or non-cell analyte. The blocking agent can be non-fluorescent at the wavelength that activates fluorescence of the dye or stain. A number of suitable blocking agents are known in the art and can be readily utilized in the embodiments of the present disclosure, including, without limitation, bisbenzamide (N,N'-(dithiodi-2,1-phenyl)-bisbenzamide), Hoechst33258 dye (bisbenzimide, 2'-(4-hydroxyphenyl)-5-(4-methyl-1-peperazinyl)-2,5-bi-1H-benzimidazole trihydrochloride pentahydrate), Hoechst 34580 dye, Hoechst 33342 dye (bisbenzimide, 2'-(ethoxyphenyl)-5-(4-methyl-1-peperazinyl)-2,5-bi-1H-benzimidazole trihydrochloride trihydrate), 4',6-diamidino-2-phenyl-indole dihydrochloride (DAPI), 4',6-bis-[2-imidazoxolinyl-4H, 5H]-2-phenyl-indole (DIPI), Eosin Y dye, Orcein dye, Phloxine B dye (2',4',5',7'-tetrabromo-4,5,6,7-tetrachlorofluorescein disodium salt), Pentoxiphilline dye, Quinacrine dye (6-chloro-9-(4-diethyl-1-methylbutylamino)-2-methoxyacridine dihydrochloride), combinations thereof, and derivatives thereof.

RNA Fluorescence In Situ Hybridization

RNA fluorescence in situ hybridization (RNA-FISH) is a molecular cytogenetic technique to detect and localize specific RNFigA targets (mRNA, lncRNA and miRNA) in single cells via fluorescence microscopy. The traditional RNA-FISH methods usually include multiple steps, e.g., fixation, permeabilization, hybridization and imaging. Although FISH has wide medical applications, the complexity of the technique limits its potential in rapid diagnostics. Therefore, it is desirable to develop a fast, accurate, portable, and/or inexpensive RNA-FISH assay, which can be conducted by a non-professional.

In some embodiments, fluorescent in situ hybridization (FISH) can be used to detect a cell or non-cell analyte within a sample. In some embodiments, FISH can be used to detect a cell or non-cell analyte by enhancing signal from the cell or non-cell analyte relative to a background signal. FISH can generally refer to any method that uses one or more probes to detect a cell or non-cell analyte within a sample, including DNA probes to detect and localize the presence or absence of specific DNA sequences on chromosomes and RNA probes to detect or localize specific RNA targets (mRNA, lncRNA and miRNA). Thus, FISH is often used for finding specific features in DNA for use in genetic counseling, medicine, and species identification as well as define the spatial-temporal patterns of gene expression within cells and tissues. In some embodiments, probe can be short strands of DNA or RNA (often 10-25 nucleotides) which are complementary to a given target sequence are often used to locate a target. In some embodiments, Stellaris® RNA FISH probes can be used, which is an RNA visualization method that allows simultaneous detection, localization, and quantification of individual mRNA molecules.

In some embodiment, the surfactant used to permeabilize to allow probe accessibility including but not limit to Zwittergent, ASB-14, ASB-16, CHAPS, Cationic surfactant NN-[Tris(hydroxymethyl) methyl]-N-alkyl-N,N-dimethyl ammonium chloride (IIa), IIb, IIc, IId, CTAC, TWEEN® 20, TWEEN® 40, TWEEN® 60, TWEEN® 80, Sodium lauryl sulfate (SLS), ammonium lauryl sulfate, CTAB, sodium lauryl ether sulfate (SLES), sodium myreth sulfate, docusate, perfluorooctanesulfonate, alkyl-aryl ether phosphates, alkyl ether phosphates, CTAB, cetylpyridinium chloride (CPC), benzalkonium chloride (BAC), benzethonium chloride (BZT), dimethyldioctadecylammonium chloride, dioctadecyldimethlyammonium bromide (DODAB), cocamidopropyl hydroxysultaine, cocamidopropyl betaine, narrow-range ethoxylate, octaethylene glycol monododecyl ether, pentaethylene glycol monododecyl ether, nonxynols, TRITON X-100™, polyethoxylated tallow amine, cocamide monoethanolamine, cocamide diethanolamine, poloxamers, glycerol monostearate, glycerol monolaurate, sorbitan monolaurate, sorbitan monostearate, sorbitan tristearate, decyl glucoside, lauryl glucoside, octyl glucoside, lauryldimethylamine oxide, dimethyl sulfoxide, phosphine oxide.

In some embodiment, the reagent causing red blood cell lysis coated in the device including but not limit to Pluronic™ F-127, Cremophor EL, Pluronic™ F-68, Myrj 52, Brij 35, sodium oleate, sodium dodecyl sulfate, TWEEN® 20, TWEEN® 40, TWEEN® 60, TWEEN®80, SLS, CTAB, CTAC, Tamoxifen, saponin, hydrochloric acid, sulfuric acid, nitric acid, phosphoric acid, lactic acid, ABS-14, ABS-16, anti-malaria drugs (quinine compounds), arsenic, dapsone, metals (chromium/chromates, platinum salts, nickel compounds, copper, lead, cis-platinum), nitrites, nitrofurantoin, penicillin, phenazopyridine (pyridium), rho immune globulin, ribavirin, sulfonamides, sulfones.

Any RNA/DNA probe used in an embodiment of the present disclosure can be labeled. A label can refer to a molecule that, when attached (directly or indirectly) to another molecule provides or enhances a means of detecting the other molecule. A signal emitted from a label can allow detection of the molecule or complex to which it is attached, and/or the label itself. A label can be a molecular species that elicits a physical or chemical response that can be observed or detected by the naked eye or by means of instrumentation such as, without limitation, cameras (e.g., mobile phone cameras), scintillation counters, colorimeters, UV spectrophotometers and the like. Labels include but are not limited to, radioactive isotopes, fluorophores, chemiluminescent dyes, chromophores, enzymes, enzymes substrates, enzyme cofactors, enzyme inhibitors, dyes, metal ions, nanoparticles, metal sols, ligands (such as biotin, avidin, streptavidin or haptens) and the like. A fluorescence or fluorescent label or tag emits detectable light at a particular wavelength when excited at a different wavelength. A radiolabel or radioactive tag emits radioactive particles detectable with an instrument such as, without limitation, a scintillation counter. Other signal generation detection methods include: chemiluminescence detection, electrochemiluminescence detection, Raman energy detection, colorimetric detection, hybridization protection assays, and mass spectrometry. Non limiting examples of labels include a fluorophore, a chromophore, FITC, TRITC, DTAF, Texas-Red, phycoerythrin, allophycocyanin, a green fluorescent protein (GFP), a blue fluorescent protein (BFP), rhodamine, FAM, TET, HEX, JOE, TAMRA, ROX, an aromatic-substituted xanthene dye, 4,7-dichloro-fluorescein, 4,7-dichloro-rhodamine, a cyanine dye, an enzyme, horseradish peroxidase (HRP), alkaline phosphatase, beta-galactosidase, luciferase, chloramphenicol acetyltransferase (CAT), avidin, streptavidin, biotin, a biotinylated protein, or any combination, fragments or derivatives thereof. In any embodiments, of the present disclosure, one or more labels can used to detect a cell or non-cell analyte. In any embodiments, of the present disclosure, two or more labels can used to detect a cell or non-cell analyte. In some embodiments, where two or more labels are used to detect a cell or non-cell analyte, the excitation and/or emission spectrum of the two or more labels can be the same. For example, a sample can be contacted with two antibodies (e.g., each of which bind to the same epitope on the same antigen), each having a different label that excites at the same wavelength. In another example, a sample can be contacted with two antibodies (e.g., each of which bind to a different epitope on the same antigen), each having the same label that excites at a predetermined wavelength. In some embodiments, where two or more labels are used to detect a cell or non-cell analyte, the excitation and/or emission spectrum of the two or more labels can be different. In some embodiments, where three or more labels are used to detect a cell or non-cell analyte, the excitation and/or emission spectrum of at least two or more labels can be the same. In some embodiments, where three or more labels are used to detect a cell or non-cell analyte, the excitation and/or emission spectrum of at least two or more labels can be different.

Protocol

Figure 4:
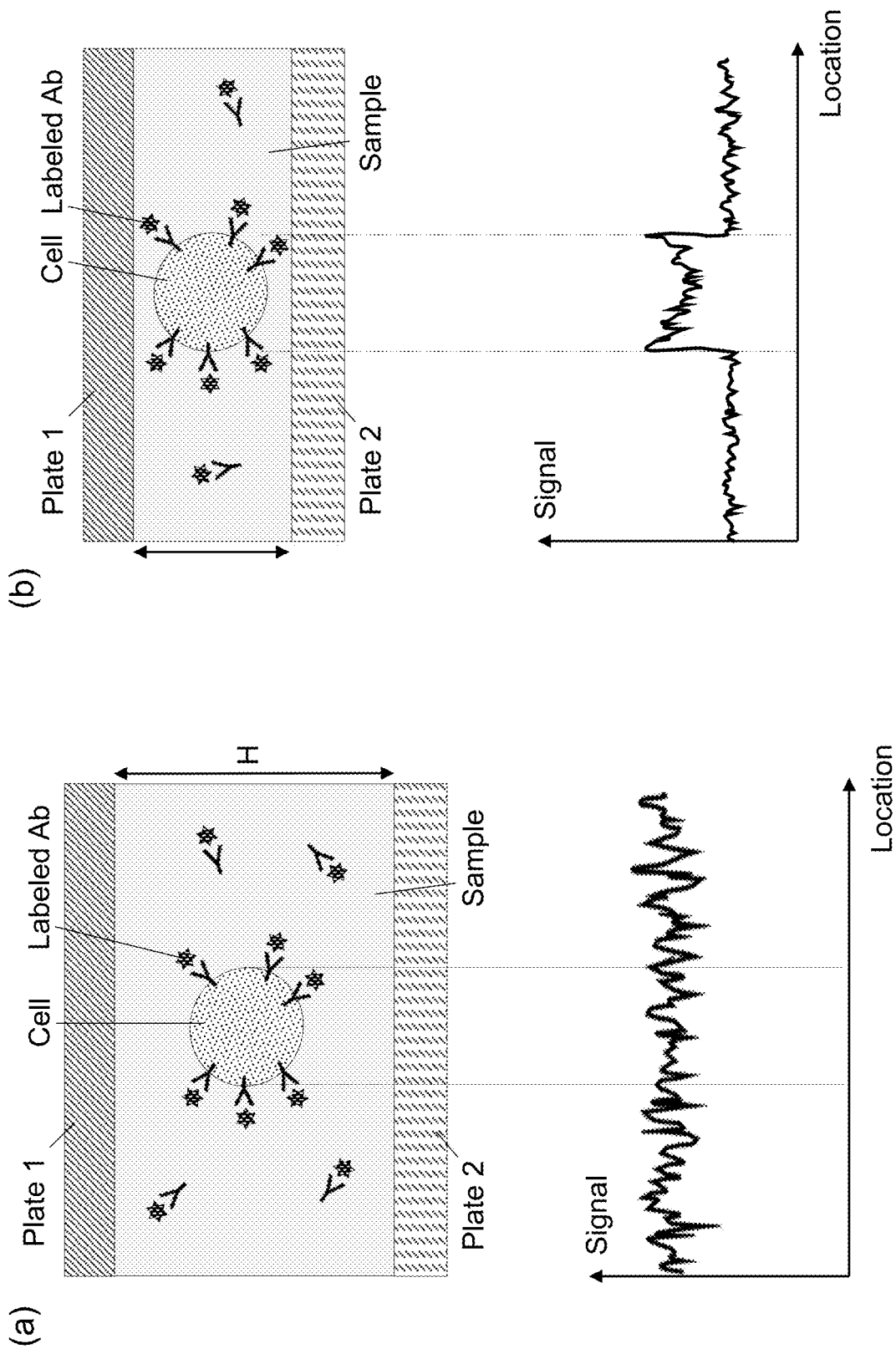
FIG. 4 shows an exemplary effect of varying spacer height on signal detection from a cell or non-cell analyte within a sample. (a) shows the cell labeled by antibodies in large spacer height has signal covered by the high background from non-cell analyte in sample; (b) shows the cell labeled by antibodies in small spacer height has signal over the background from non-cell analyte in sample.

1. Design, synthesize and purify fluorescent probes for target RNA.
2. Use Biodot to print probe (1 nM) and surfactant (e.g. Zwittergent) on X-plate.
3. Apply one drop of blood on substrate plate, close chip, press, and incubate at room temperature for 1 minute.
4. Insert chip to the device, take pictures and analyze data Spacer Height & Sample Thickness In some embodiments of the present disclosure, the spacer height can be varied to adjust the thickness of the sample being analyzed, and thereby enhance the detection of a signal from a target cell or non-cell analyte. For example, as shown in FIG. 4, a signal detected from the cell or non-cell analyte relative to a background signal can be enhanced by varying the thickness of the sample from a larger thickness (FIG. 4A) to a smaller thickness (FIG. 4B). In some embodiments, the spacer height and/or thickness of the sample can be at most about 500 micrometers, at most about 250 micrometers, at most about 100 micrometers, at most about 90 micrometers, at most about 80 micrometers, at most about 70 micrometers, at most about 60 micrometers, at most about 50 micrometers, at most about 40 micrometers, at most about 30 micrometers, at most about 25 micrometers, at most about 20 micrometers, at most about 15 micrometers, at most about 10 micrometers, at most about 5 micrometers, at most about 4 micrometers, at most about 3 micrometers, at most about 2 micrometers, at most about 1 micrometers, at most about 0.5 micrometers, at most about 0.1 micrometers, or at most about 0.05 micrometers. For example, the spacer height can be at most about 30 micrometers. In some embodiments, the spacer height and/or thickness of the sample can be about 25 micrometers to about 35 micrometers. In some embodiments, the spacer height and/or thickness of the sample can be about 20 micrometers to about 40 micrometers. In some embodiments, the spacer height and/or thickness of the sample can be about 10 micrometers to about 30 micrometers. In some embodiments, the spacer height and/or thickness of the sample can be about 30 micrometers to about 50 micrometers. In some embodiments, the spacer height and/or thickness of the sample can be about 50 micrometers to about 75 micrometers. In some embodiments, the spacer height and/or thickness of the sample can be about 1 micrometers to about 25 micrometers. For example, the spacer height and/or thickness of the sample can be about 25 microns to about 35 microns. In some embodiments, the spacer height and/or thickness of the sample can be determined based on a size or shape of a target cell or non-cell analyte. For example, lymphocytes can have an average diameter in suspension about 15 micrometers. Accordingly, in some embodiments, the spacer height and/or thickness of the sample can be about 15 micrometers, about 20 micrometers, about 25 micrometers, about 30 micrometers, or greater than about 30 micrometers.

Examples of the Present Invention

A1. A method for analyzing a sample, the method comprising:
- (a) obtaining a device according to an embodiment as disclosed herein, the device comprising a first plate, a second plate, and spacers, wherein the spacers have a predetermined substantially uniform height that is equal to or less than about 200 microns;
- (b) contacting the sample with two or more labeled antibodies to obtain a mixture, wherein said two or more labeled antibodies are capable of binding to one or more epitopes on a target cell within said sample;
- (c) depositing the mixture on one or both of the plates when the plates are configured in an open configuration, wherein the open configuration is a configuration in which the two plates are partially or completely separated apart and the spacing between the plates is not regulated by the spacers;
- (d) after (c), forcing the two plates into a closed configuration, in which: at least part of the mixture is compressed by the two plates into a layer of substantially uniform thickness, wherein the uniform thickness of the layer is confined by the mixture contact surfaces of the plates and is regulated by the plates and the spacers.

A2. A method for analyzing a sample, the method comprising:
- (a) obtaining a device according to an embodiment as disclosed herein, the device comprising a first plate, a second plate, and spacers, wherein the spacers have a predetermined substantially uniform height that is equal to or less than about 200 microns, and wherein at least one of said first plate, said second plate, and said spacers comprise at least one surface coated with two or more labeled antibodies;
- (b) depositing the sample on one or both of the plates when the plates are configured in an open configuration, wherein the open configuration is a configuration in which the two plates are partially or completely separated apart and the spacing between the plates is not regulated by the spacers, wherein upon deposition of the sample on one or both plates, said sample is contacted with said two or more labeled antibodies, wherein said two or more labeled antibodies are capable of binding to one or more epitopes on a target cell within said sample;
- (c) after (b), forcing the two plates into a closed configuration, in which: at least part of the sample is compressed by the two plates into a layer of substantially uniform thickness, wherein the uniform thickness of the layer is confined by the sample contact surfaces of the plates and is regulated by the plates and the spacers.

A3. The method of any prior embodiment, wherein the spacers have a predetermined substantially uniform height that is equal to or less than about 100 microns, equal to or less than about 75 microns, equal to or less than about 50 microns, equal to or less than about 30 microns, equal to or less than about 25 microns, equal to or less than about 10 microns, equal to or less than about 5 microns, or equal to or less than about 1 micron.

A4. The method of any prior embodiment, wherein said predetermined substantially uniform height of said spacers is determined based on a size or a shape of said target cell.

A5. The method of any prior embodiment, wherein said two or more labeled antibodies bind different epitopes on a molecule of said target cell.

A6. The method of any prior embodiment, wherein said two or more labeled antibodies bind the same epitope.

A7. The method of any prior embodiment, wherein said two or more labeled antibodies bind different molecules on said target cell.

A7.1 The method of any prior embodiment, wherein said labels coupled to said two or more labeled antibodies are capable of excitation at the same wavelength.

A8. A method for analyzing a sample, the method comprising:
  (a) obtaining a device according to an embodiment as disclosed herein, the device comprising a first plate, a second plate, and spacers, wherein the spacers have a predetermined substantially uniform height that is equal to or less than about 200 microns, wherein said first plate comprises a surface coated with a first antibody and said second plate comprises a surface coated with a second antibody;
  (b) depositing the sample on one or both of the plates when the plates are configured in an open configuration, wherein the open configuration is a configuration in which the two plates are partially or completely separated apart and the spacing between the plates is not regulated by the spacers, wherein upon deposition of the sample on one or both plates, said sample is contacted with said first antibody and said second antibody, wherein said first antibody and said second antibody are capable of binding to one or more epitopes on a target cell within said sample;
  (c) after (b), forcing the two plates into a closed configuration, in which: at least part of the sample is compressed by the two plates into a layer of substantially uniform thickness, wherein the uniform thickness of the layer is confined by the sample contact surfaces of the plates and is regulated by the plates and the spacers.

A9. A method for analyzing a sample, the method comprising:
  (a) obtaining a device according to an embodiment as disclosed herein, the device comprising a first plate, a second plate, and spacers, wherein the spacers have a predetermined substantially uniform height that is equal to or less than about 200 microns;
  (b) contacting the sample with two or more dyes to obtain a mixture, wherein said two or more labeled dyes are capable of binding to a target cell within said sample;
  (c) depositing the mixture on one or both of the plates when the plates are configured in an open configuration, wherein the open configuration is a configuration in which the two plates are partially or completely separated apart and the spacing between the plates is not regulated by the spacers;
  (d) after (c), forcing the two plates into a closed configuration, in which: at least part of the mixture is compressed by the two plates into a layer of substantially uniform thickness, wherein the uniform thickness of the layer is confined by the mixture contact surfaces of the plates and is regulated by the plates and the spacers.

A10. A method for analyzing a sample, the method comprising:
  (a) obtaining a device according to an embodiment as disclosed herein, the device comprising a first plate, a second plate, and spacers, wherein the spacers have a predetermined substantially uniform height that is equal to or less than about 200 microns, and wherein at least one of said first plate, said second plate, and said spacers comprise at least one surface coated with two or more dyes;
  (b) depositing the sample on one or both of the plates when the plates are configured in an open configuration, wherein the open configuration is a configuration in which the two plates are partially or completely separated apart and the spacing between the plates is not regulated by the spacers, wherein upon deposition of the sample on one or both plates, said sample is contacted with said two or more dyes, wherein said two or more dyes are capable of binding to a target cell within said sample;
  (c) after (b), forcing the two plates into a closed configuration, in which: at least part of the sample is compressed by the two plates into a layer of substantially uniform thickness, wherein the uniform thickness of the layer is confined by the sample contact surfaces of the plates and is regulated by the plates and the spacers.

A11. The method of any prior embodiment, wherein the spacers have a predetermined substantially uniform height that is equal to or less than about 100 microns, equal to or less than about 75 microns, equal to or less than about 50 microns, equal to or less than about 30 microns, equal to or less than about 25 microns, equal to or less than about 10 microns, equal to or less than about 5 microns, or equal to or less than about 1 micron.

A12. The method of any prior embodiment, wherein said predetermined substantially uniform height of said spacers is determined based on a size or a shape of said target cell.

A13. The method of any prior embodiment, wherein said two or more dyes non-specifically bind said target cell.

A14. The method of any prior embodiment, wherein said two or more dyes are capable of excitation at the same wavelength.

A15. A method for analyzing a sample, the method comprising:
  (d) obtaining a device according to an embodiment as disclosed herein, the device comprising a first plate, a second plate, and spacers, wherein the spacers have a predetermined substantially uniform height that is equal to or less than about 200 microns, wherein said first plate comprises a surface coated with an antibody and said second plate comprises a surface coated with a dye;
  (e) depositing the sample on one or both of the plates when the plates are configured in an open configuration, wherein the open configuration is a configuration in which the two plates are partially or completely separated apart and the spacing between the plates is not regulated by the spacers, wherein upon deposition of the sample on one or both plates, said sample is contacted with said antibody and said dye, wherein said antibody and said dye are capable of binding to a target cell within said sample;
  (f) after (b), forcing the two plates into a closed configuration, in which: at least part of the sample is compressed by the two plates into a layer of substantially uniform thickness, wherein the uniform thickness of the layer is confined by the sample contact surfaces of the plates and is regulated by the plates and the spacers.

A16. A method for analyzing a sample, the method comprising:
  (e) obtaining a device according to an embodiment as disclosed herein, the device comprising a first plate, a second plate, and spacers, wherein the spacers have a predetermined substantially uniform height that is equal to or less than about 200 microns;
  (f) contacting the sample with a labeled antibody and a dye to obtain a mixture, wherein said labeled antibody and said dye are capable of binding to a target cell within said sample;
  (g) depositing the mixture on one or both of the plates when the plates are configured in an open configuration, wherein the open configuration is a configuration in which the two plates are partially or completely separated apart and the spacing between the plates is not regulated by the spacers;

(h) after (c), forcing the two plates into a closed configuration, in which: at least part of the mixture is compressed by the two plates into a layer of substantially uniform thickness, wherein the uniform thickness of the layer is confined by the mixture contact surfaces of the plates and is regulated by the plates and the spacers.

A17. A method for analyzing a sample, the method comprising:

(d) obtaining a device according to an embodiment as disclosed herein, the device comprising a first plate, a second plate, and spacers, wherein the spacers have a predetermined substantially uniform height that is equal to or less than about 200 microns, and wherein at least one of said first plate, said second plate, and said spacers comprise at least one surface coated with a labeled antibody and a dye;

(e) depositing the sample on one or both of the plates when the plates are configured in an open configuration, wherein the open configuration is a configuration in which the two plates are partially or completely separated apart and the spacing between the plates is not regulated by the spacers, wherein upon deposition of the sample on one or both plates, said sample is contacted with said labeled antibody and said dye, wherein said labeled antibody and said dye are capable of binding to a target cell within said sample;

(f) after (b), forcing the two plates into a closed configuration, in which: at least part of the sample is compressed by the two plates into a layer of substantially uniform thickness, wherein the uniform thickness of the layer is confined by the sample contact surfaces of the plates and is regulated by the plates and the spacers.

A18. The method of any prior embodiment, wherein the spacers have a predetermined substantially uniform height that is equal to or less than about 100 microns, equal to or less than about 75 microns, equal to or less than about 50 microns, equal to or less than about 30 microns, equal to or less than about 25 microns, equal to or less than about 10 microns, equal to or less than about 5 microns, or equal to or less than about 1 micron.

A19. The method of any prior embodiment, wherein said predetermined substantially uniform height of said spacers is determined based on a size or a shape of said target cell.

A20. The method of any prior embodiment, wherein said dye non-specifically binds to said target cell.

A21. The method of any prior embodiment, wherein said label on said labeled antibody and said dye are capable of excitation at the same wavelength.

In one embodiment, stain reagent and additives are coated on the same plate (1st or 2nd plate), or separate plate (1st and 2nd plate).

In one embodiment, additives are chemicals that have physical, or chemical or physiological impact on target cell. Examples are surfactant (refer to other Provisionals) and ions (refer to other Provisionals).

In one embodiment, stain reagent is labeled antibody, peptide, oligonucleotide, aptamer, small molecules and any other substances that have binding affinity to one or multiple specific components, inside or outside, of target cell.

In one embodiment, the detection of labeled stain reagent is fluorescence-based (refer to other Provisionals), chemiluminescence-based (refer to other Provisionals) or colorimetric-based (refer to other Provisionals) or plasmonic-based (refer to other Provisionals).

In one embodiment, the target cell is a prokaryote such as bacteria and archaea, or eukaryote such as animal cell and plant cell. Common examples include mammalian cells, yeast and algae etc.

In one embodiment, the number of target cell in sample can be one or more than one.

In some embodiments, the reagents coating on the device including an agent making cell membrane or cell nucleus permeable, including but not limit to TRITON X-100™, surfactant, Zwittergent, ASB-14, ASB-16, CHAPS, Cationic surfactant NN-[Tris(hydroxymethyl) methyl]-N-alkyl-N,N-dimethyl ammonium chloride (IIa), IIb, IIc, IId, CTAC, TWEEN® 20, TWEEN® 40, TWEEN® 60, TWEEN® 80, Sodium lauryl sulfate (SLS), ammonium lauryl sulfate, CTAB, sodium lauryl ether sulfate (SLES), sodium myreth sulfate, docusate, perfluorooctanesulfonate, alkyl-aryl ether phosphates, alkyl ether phosphates, CTAB, cetylpyridinium chloride (CPC), benzalkonium chloride (BAC), benzethonium chloride (BZT), dimethyldioctadecylammonium chloride, dioctadecyldimethlyammonium bromide (DODAB), cocamidopropyl hydroxysultaine, cocamidopropyl betaine, narrow-range ethoxylate, octaethylene glycol monododecyl ether, pentaethylene glycol monododecyl ether, nonxynols, TRITON X-100™, polyethoxylated tallow amine, cocamide monoethanolamine, cocamide diethanolamine, poloxamers, glycerol monostearate, glycerol monolaurate, sorbitan monolaurate, sorbitan monostearate, sorbitan tristearate, decyl glucoside, lauryl glucoside, octyl glucoside, lauryldimethylamine oxide, dimethyl sulfoxide, phosphine oxide.

In some embodiments, the reagents coating on the device including an agent making cell membrane or cell nucleus permeable, by method of osmotic pressure difference between the cell membrane as dilution, or tuning salt concentration.

In some embodiments, the reagents coating on the device including an agent making protein cross link, including but not limit to formaldehyde, glutaraldehyde, osmium tetroxide, potassium dichromate and potassium permanganate.

The device, kit, system, or method of any prior embodiments, wherein the dye to stain the WBC is coated onto the first plate, or the second plate or both.

The device, kit, system, or method of any prior embodiments, wherein the dye to stain the WBC and PLT is coated onto the first plate, or the second plate or both.

The device, kit, system, or method of any prior embodiments, wherein the dye to stain the PLT is coated onto the first plate, or the second plate or both.

The device, kit, system, or method of any prior embodiments, wherein the reagents is coated by droplet printing into an array.

The device, kit, system, or method of any prior embodiments, wherein the reagents is coated using the open guided flow properties of structures on plates.

The device, kit, system, or method of any prior embodiments, wherein the reagents is coated by spray.

The device, kit, system, or method of any prior embodiments, wherein the reagents is coated by contact printing.

The device, kit, system, or method of any prior embodiments, wherein the reagents is coated by transfer printing.

The device, kit, system, or method of any prior embodiments, wherein the dye to stain the RBC is coated onto the first plate, or the second plate or both.

The device, kit, system, or method of any prior embodiments, wherein the surfactant to separate and round RBC is coated onto the first plate, or the second plate or both.

The device, kit, system, or method of any prior embodiments, wherein the chemical to lyse RBC is coated onto the first plate, or the second plate or both.

The device, kit, system, or method of any prior embodiments, wherein the acridine orange is coated onto the first plate, or the second plate or both.

The device, kit, system, or method of any prior embodiments, wherein the Zwittergent is coated onto the first plate, or the second plate or both.

The device, kit, system, or method of any prior embodiments, wherein the Methylene blue and Zwittergent is coated onto the first plate, or the second plate or both.

The device, kit, system, or method of any prior embodiments, wherein the acridine orange and Zwittergent is coated onto the first plate, or the second plate or both.

The device, kit, system, or method of any prior embodiments, wherein the YOYO dye and Zwittergent is coated onto the first plate, or the second plate or both.

The devices or methods of any prior embodiment, wherein the device further comprises, on one or both plates, multi reagent layers including anti-conglutination, cell lysing, cell staining, release time control material layers, and their combinations;

wherein each layer coated on the plates has a thickness of 10 nm, 100 nm, 200 nm, 500 nm, 1 um or a range between any two of the values.

where anti-conglutination agent comprises ethylenediaminetetraacetic acid (EDTA), EDTA disodium, K2EDTA, K3EDTA, and etc.

wherein cell stain agent comprise Wright's stain (Eosin, methylene blue), Giemsa stain (Eosin, methylene blue, and Azure B), May-Grünwald stain, Leishman's stain ("Polychromed" methylene blue (i.e. demethylated into various azures) and eosin), Erythrosine B stain (Erythrosin B), and other fluorescence stain including but not limit to Acridine orange dye, 3,3-dihexyloxacarbocyanine (DiOC6), Propidium Iodide (PI), Fluorescein Isothiocyanate (FITC) and Basic Orange 21 (B021) dye, Ethidium Bromide, Brilliant Sulfaflavine and a Stilbene Disulfonic Acid derivative, Erythrosine B or trypan blue, Hoechst 33342, Trihydrochloride, Trihydrate, and DAPI (4',6-Diamidino-2-Phenylindole, Dihydrochloride), YOYO dye.

wherein cell stain agent comprise Wright's stain (Eosin, methylene blue), Giemsa stain (Eosin, methylene blue, and Azure B), May-Grünwald stain, Leishman's stain ("Polychromed" methylene blue (i.e. demethylated into various azures) and eosin), Erythrosine B stain (Erythrosin B), and other fluorescence stain including but not limit to Acridine orange dye, 3,3-dihexyloxacarbocyanine (DiOC6), Propidium Iodide (PI), Fluorescein Isothiocyanate (FITC) and Basic Orange 21 (B021) dye, Ethidium Bromide, Brilliant Sulfaflavine and a Stilbene Disulfonic Acid derivative, Erythrosine B or trypan blue, Hoechst 33342, Trihydrochloride, Trihydrate, and DAPI (4',6-Diamidino-2-Phenylindole, Dihydrochloride), YOYO dye, acid fuchsine, hematoxylin, Hoechst stains including Hoechst 33258 and Hoechst 33342, methyl green, methylene blue, Nile blue, Nile red, osmium tetraoxide, rhodamine, safranine, MeOSuc-AAPV-AMC, CFSE, BCECF/AM, silver nitrate, neutral red, pyronin Y, Calcein-AM, Dihydroethidium, Xylene Cyanol FF, Rhodamine 123, 4-Methylumbelliferyl palmitate, Fast Blue B Salt, Lucifer Yellow CH dipotassium salt, DAPI dilactate, Propidium Iodide;

wherein cell lysing agent comprise ammonium chloride, sodium bicarbonate, ethylenediaminetetraacetic acid (EDTA), acetic acid, citric acid, other acid and base, and etc.

wherein release time control material comprise albumin, carbomers, carboxymethyl cellulose, carrageenan, chitosan, dextrin, polyethylene glycol, polyvinylpyrrolidone, polyvinyl alcohol, and etc.

In some embodiment, chemicals with certain concentration is coated on the plate and dissolved into the blood to achieve a uniform distribution of red blood cell in device.

In some embodiment, chemicals with certain concentration is coated on the plate and dissolved into the blood to lyse the red blood cell in the device, wherein the coating can be on first plate, or second plate, or both.

In some embodiment, the chemicals coated in the device including but not limit to Surfactant, Zwittergent, ASB-14, ASB-16, CHAPS, Cationic surfactant NN-[Tris(hydroxymethyl) methyl]-N-alkyl-N,N-dimethyl ammonium chloride (IIa), IIb, IIc, IId, CTAC, TWEEN® 20, TWEEN® 40, TWEEN® 60, TWEEN® 80, Sodium lauryl sulfate (SLS), ammonium lauryl sulfate, CTAB, sodium lauryl ether sulfate (SLES), sodium myreth sulfate, docusate, perfluorooctanesulfonate, alkyl-aryl ether phosphates, alkyl ether phosphates, CTAB, cetylpyridinium chloride (CPC), benzalkonium chloride (BAC), benzethonium chloride (BZT), dimethyldioctadecylammonium chloride, dioctadecyldimethlyammonium bromide (DODAB), cocamidopropyl hydroxysultaine, cocamidopropyl betaine, narrow-range ethoxylate, octaethylene glycol monododecyl ether, pentaethylene glycol monododecyl ether, nonxynols, TRITON X-100™, polyethoxylated tallow amine, cocamide monoethanolamine, cocamide diethanolamine, poloxamers, glycerol monostearate, glycerol monolaurate, sorbitan monolaurate, sorbitan monostearate, sorbitan tristearate, decyl glucoside, lauryl glucoside, octyl glucoside, lauryldimethylamine oxide, dimethyl sulfoxide, phosphine oxide.

In some embodiment, the reagent causing red blood cell lysis coated in the device including but not limit to Pluronic™ F-127, Cremophor EL, Pluronic™ F-68, Myrj 52, Brij 35, sodium oleate, sodium dodecyl sulfate, TWEEN® 20, TWEEN® 40, TWEEN® 60, TWEEN®80, SLS, CTAB, CTAC, Tamoxifen, saponin, hydrochloric acid, sulfuric acid, nitric acid, phosphoric acid, lactic acid, ABS-14, ABS-16, anti-malaria drugs (quinine compounds), arsenic, dapsone, metals (chromium/chromates, platinum salts, nickel compounds, copper, lead, cis-platinum), nitrites, nitrofurantoin, penicillin, phenazopyridine (pyridium), rho immune globulin, ribavirin, sulfonamides, sulfones.

In some embodiment, the anticoagulant coated in the device including but not limit to EDTA such as dipotassium ethylenediaminetetraacetic acid (K2EDTA), tripotassium ethylenediaminetetraacetic (K3EDTA), coumarins (vitamin K antagonists), warfarin (coumadin), acenocoumarol, phenprocoumon, atromentin, phenindione, heparin, fondaparinux and idraparinux, dabigatran, rivaroxaban, apixaban, edoxaban, betrixaban, NOACs, hirudin, lepirudin, bivalirudin, agratroban, dabigatran, batroxobin, hementin, Vitamin E, sodium citrate, acid citrate dextrose, oxalate such as fluoride oxalate, deltaparin, desirudin, enoxaparin.

In some embodiment, to achieve a uniform distribution of red blood cell in device, Zwittergent is coated on the plate with a preferred area concentration of 3 ng/mm$^2$, 5 ng/mm$^2$, 8 ng/mm$^2$, 12 ng/mm$^2$, 15 ng/mm$^2$, 25 ng/mm$^2$, 35 ng/mm$^2$, 50 ng/mm$^2$, 80 ng/mm$^2$, 100 ng/mm$^2$ or in a range between any of the two values.

In some embodiment, to lyse red blood cell in device, Zwittergent is coated on the plate with a preferred area concentration of 100 ng/mm$^2$, 120 ng/mm$^2$, 150 ng/mm$^2$, 180 ng/mm², 200 ng/mm², 300 ng/mm², 400 ng/mm², 500 ng/mm², 800 ng/mm², 1000 ng/mm² or in a range between any of the two values.

In some embodiment, to achieve a uniform distribution of red blood cell in device, Zwittergent is coated on the plate with a preferred final concentration in blood of 0.05 mg/mL, 0.1 mg/mL, 0.2 mg/mL, 0.3 mg/mL, 0.5 mg/mL, 0.6 mg/mL, 1.0 mg/mL, 2 mg/mL or in a range between any of the two values.

In some embodiment, to lyse red blood cell in device, Zwittergent is coated on the plate with a preferred final concentration in blood of 2 mg/mL, 3 mg/mL, 4 mg/mL, 5 mg/mL, 6 mg/mL, 7 mg/mL, 9 mg/mL, 10 mg/mL, 15 mg/mL, 25 mg/mL, 50 mg/mL, or in a range between any of the two values.

In some embodiment, to achieve a uniform distribution of red blood cell in device, Zwittergent is coated on the plate with a preferred area concentration of 3 ng/mm², 5 ng/mm², 8 ng/mm², 12 ng/mm², 15 ng/mm², 25 ng/mm², 35 ng/mm², 50 ng/mm², 80 ng/mm², 100 ng/mm² or in a range between any of the two values.

In some embodiment, to lyse red blood cell in device, Zwittergent is coated on the plate with a preferred area concentration of 100 ng/mm², 120 ng/mm², 150 ng/mm², 180 ng/mm², 200 ng/mm², 300 ng/mm², 400 ng/mm², 500 ng/mm², 800 ng/mm², 1000 ng/mm² or in a range between any of the two values.

In some embodiment, to achieve a uniform distribution of red blood cell in device, Zwittergent is coated on the plate with a preferred final concentration in blood of 0.05 mg/mL, 0.1 mg/mL, 0.2 mg/mL, 0.3 mg/mL, 0.5 mg/mL, 0.6 mg/mL, 1.0 mg/mL, 2 mg/mL or in a range between any of the two values.

In some embodiment, to lyse red blood cell in device, Zwittergent is coated on the plate with a preferred final concentration in blood of 2 mg/mL, 3 mg/mL, 4 mg/mL, 5 mg/mL, 6 mg/mL, 7 mg/mL, 9 mg/mL, 10 mg/mL, 15 mg/mL, 25 mg/mL, 50 mg/mL, or in a range between any of the two values.

The device, kit, system, or method of any prior embodiments, wherein the acridine orange is coated on the plate with an area concentration of 0.5 ng/mm², 1 ng/mm², 2 ng/mm², 3 ng/mm², 5 ng/mm², 8 ng/mm², 10 ng/mm², 15 ng/mm², 20 ng/mm², 30 ng/mm² or in a range between any of the two values.

The device, kit, system, or method of any prior embodiments, wherein the acridine orange is coated on the plate with an area concentration of 3 to 10 ng/mm² and Zwittergent is coated on the plate with an area concentration of 3 to 10 ng/mm².

The device, kit, system, or method of any prior embodiments, wherein the acridine orange is coated on the plate with an area concentration of 5 to 20 ng/mm² and Zwittergent is coated on the plate with an area concentration of 10 to 30 ng/mm².

In some embodiment, label (example as immunoassay antibody label, RNA label, staining dye) is coated on the plate with a preferred final concentration in sample of 0.1 nM/mL, 0.5 nM/mL, 1 nM/mL, 5 nM/mL, 10 nM/mL, 15 nM/mL, 20 nM/mL, 50 nM/mL, or in a range between any of the two values.

In some embodiment, label (example as immunoassay antibody label, RNA label, staining dye) is coated on the plate with a preferred final concentration in sample of 1 nM/mL, 5 nM/mL, 10 nM/mL, 15 nM/mL, 20 nM/mL, or in a range between any of the two values.

In some embodiment, label (example as immunoassay antibody label, RNA label, staining dye) is coated on the plate with a preferred final concentration in sample of 0.1 uM/mL, 0.5 uM/mL, 1 uM/mL, 5 uM/mL, 10 uM/mL, 15 uM/mL, 20 uM/mL, 50 uM/mL, or in a range between any of the two values.

In some embodiment, label (example as immunoassay antibody label, RNA label, staining dye) is coated on the plate with a preferred final concentration in sample of 0.1 ng/mL, 0.5 ng/mL, 1.0 ng/mL, 1.5 ng/mL, 2.0 ng/mL, 5 ng/mL, 10 ng/mL, 50 ng/mL, or in a range between any of the two values.

In some embodiment, label (example as immunoassay antibody label, RNA label, staining dye) is coated on the plate with a preferred final concentration in sample of 0.05 mg/mL, 0.15 mg/mL, 0.3 mg/mL, 0.5 mg/mL, 1.0 mg/mL, or in a range between any of the two values.

In some embodiment, label (example as immunoassay antibody label, RNA label, staining dye) is coated on the plate with a preferred final concentration in sample of 0.1 mg/mL, 0.5 mg/mL, 1.0 mg/mL, 1.5 mg/mL, 2.0 mg/mL, 5 mg/mL, 10 mg/mL, 50 mg/mL, or in a range between any of the two values.

In some embodiment, label (example as immunoassay antibody label, RNA label, staining dye) is coated on the plate with a preferred final concentration in sample of 100 mg/mL, 200 mg/mL, 300 mg/mL, or in a range between any of the two values.

Example 1

Rapid Assay for Distinguishing Gram-Negative and Gram-Positive Bacteria

Materials:
1. Hexidium Iodide: This nucleic acid stain is permeant to mammalian cells and selectively stains most Gram-positive bacteria orange (Thermofisher, H7593).
2. SYTO 9: Stains both Gram-positive and Gram-negative bacteria green (Thermofisher, S34854).
3. 500 nm wavelength excitation filter.
4. *Staphylococcus epidermidis* (Gram-positive), *Escherichia coli* (Gram-negative).

Methods:
Bacterial Culture Preparation:
1. *S. epidermidis* and *E. coli* were used as Gram-positive and Gram-negative bacteria, respectively. These distinct bacterial species were cultured in nutrient broth (R061582, Remel) at 37° C. overnight before staining.

Figure 7:
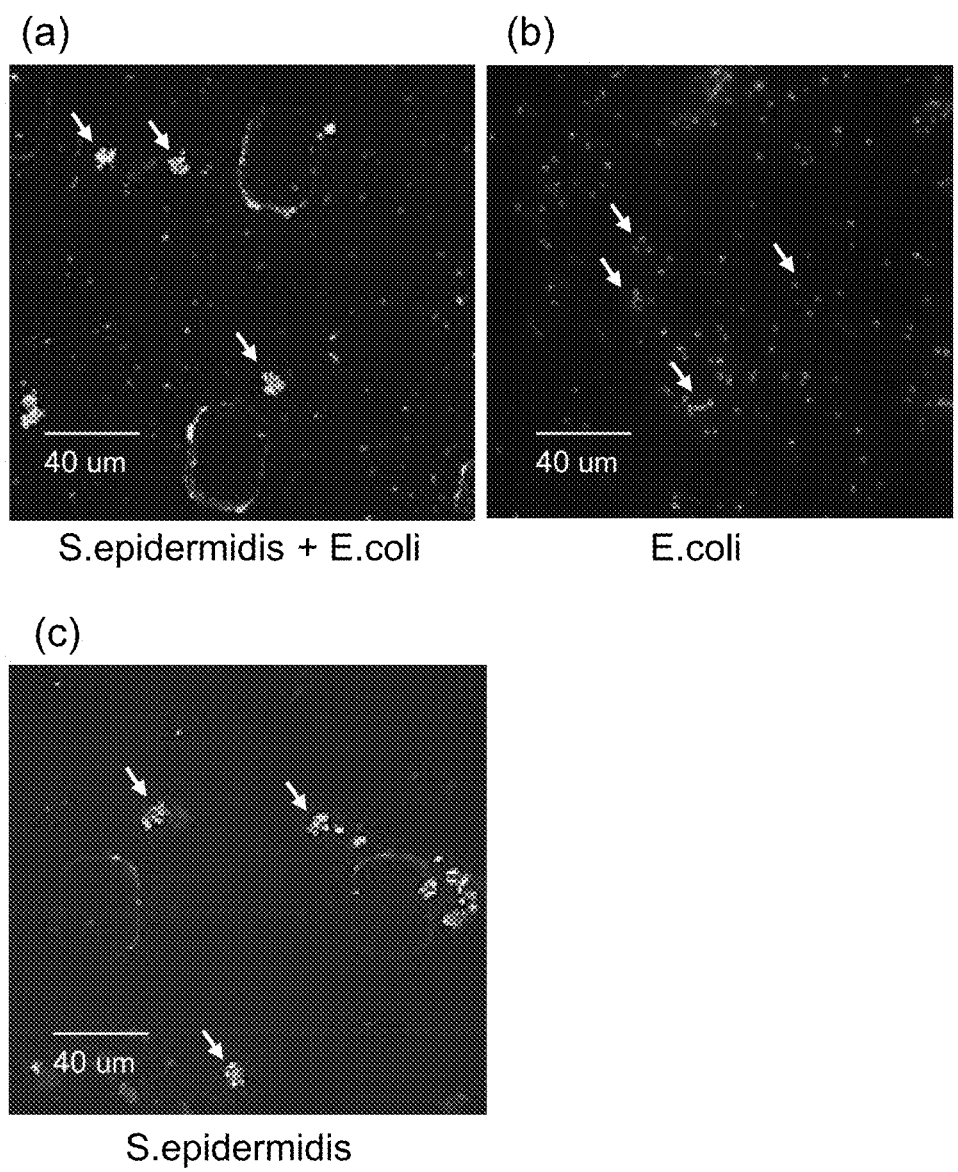
FIG. 7 shows exemplary pictures of distinguishing bacteria that are gram-positive from gram-negative using different DNA dyes. The three images are taken from different bacterial mixtures that were analyzed using the same, rapid staining assay. Bacterial mixtures analyzed: A) a mixture of bacterial species, B) *E. coli* only, C) *S. epidermidis* only.

Q-Card Preparation:
1. A mixture containing 12 ug/mL of hexidium iodide and 8 uM SYTO 9 suspended in PBS were printed on a batch of X-plates (containing 2 um height pillars) at 3 uL per cm² and air-dried.
2. 2 uL of PBS or blood that contains *S. epidermidis* and *E. coli* was added to a substrate plate. The printed X-plate and the substrate plate containing the bacterial-blood sample were pressed together firmly (FIG. 7).

Imaging:
After a 60 second incubation period, fluorescent and bright field images of the assay were taken using the iPhone 6s. Only Gram-positive bacteria appear orange, whereas both Gram-positive and Gram-negative bacteria may stain green (FIG. 7).

In this experiment, the QMAX card has two plates, one flat PMMA substrate with 1 mm thickness, one 175 um thick PMMA film with a pillar array on it, which has a pillar size 30×40 um, 80 um inter spacing (pillar) distance and 2 um pillar height.

Example 2

Rapid CD4 Immunostaining

Materials:
1. CD4 Antibodies: Ab34276 (Abcam) and 10R-CD4KHUP (Fitzgerald industrial international)
2. Antibody labeling kits:
   2.1 Alexa Fluor 647 NHS ester kit (A37573, Thermofisher)
   2.2 Zenon mouse IgG1 antibody labeling kit (Z25008, Thermofisher)
3. SYTO62 red fluorescent nucleic acid stain (S11344, Thermofisher) 5 mM in DMSO
4. Bioworld antibody bio-stabilizer 10X (22050005-2, Fisher Scientific)
5. TRITON X-100™ (X-100 100 ml, Sigma)

Methods:
1. Antibody double-labeling method:
   1.1. Primary fluorescent label: 100 ug of each CD4 detection antibody (Ab34276 and 10R-CD4KHUP) was labeled using the Alexa Fluor 647 NHS ester labeling kit (Thermofisher) following the manufacturer's protocol. After labeling the antibodies, residual dye was removed using a Sephadex-G25 column (17-0853-01, GE Health). Purified antibodies were resuspended to a final concentration of 1 ug/uL in a mixture composed of 30% glycerol and 1% BSA. Antibodies were stored at −20° C. before further use.
   1.2. Secondary fluorescent label: The Alexa Fluor 647 NHS ester labeled CD4 antibodies were labeled a second time using the Zenon Alexa Fluor 647 labeling kit (Fc-domain labeling) following the manufacturer's instruction. Briefly, 1 ug of each CD4 antibody was mixed with 8 ul of mouse IgG1 Alexa Fluor 647 labeling reagent in 15 ul PBS. The reaction mixture was incubated at room temperature for 5 minutes and then kept at 4° C. before further use. This double-labeling method significantly enhances the fluorescence signal of the CD4 specific antibodies.
2. Detection antibody mixtures:
   2D Assay: 6 ug/ml of each detection antibody that had been double-labeled is mixed together with 5 uM SYTO 62 (Red fluorescent DNA dye from Thermofisher), 0.5× of antibody bio-stabilizer (Bioworld), and 0.1% TRITON X-100™ (Sigma) in PBS. This mixture, therefore, has a final antibody concentration of 12 ug/mL mixed together with a dye that will stain DNA.
   2A Assay: 6 ug/ml of each detection antibody that had been double-labeled is mixed together with 0.5× of antibody bio-stabilizer (Bioworld) and 0.1% TRITON X-100™ (Sigma) in PBS. This mixture also has a final antibody concentration of 12 ug/mL but the DNA dye is omitted.
   1A Assay: 6 ug/ml of one detection antibody that had been double-labeled is mixed together with the 0.5× of antibody bio-stabilizer (Bioworld, and 0.1% TRITON X-100™ (Sigma) in PBS. This mixture only contains a final antibody concentration of 6 ug/mL without the DNA dye.
   1D Assay: 6 ug/ml of one detection antibody that had been double-labeled is mixed together with 0.5× of antibody bio-stabilizer (Bioworld, and 0.1% TRITON X-100™ (Sigma) in PBS. This mixture only contains one antibody with the DNA dye.
3. Surface treatment of the Q-cards:
   3.1. Both the X-plate (containing 10 um pillars) and the substrate plate were treated with 1% NaOH for 1 hour at 50° C. Both plates were subsequently washed with distilled water, PBS, and distilled water once again for 5 minutes for each wash.
   3.2. After washing the plates, they were blocked with 4% BSA for 2 hours at room temperature. The plates were washed to remove residual BSA by distilled water twice for 5 minutes, then air-dried.
4. Printing of the antibody mixture onto the Q-card:
   4.1 The prepared antibody mixture was printed at approximately 3 ul/cm$^2$ on both plates (X-plate and substrate plate). Once the antibodies had been printed, the plates were air dried and protected from the light before further use.
5. CD4 detection using the iPhone 6s:
   5.1. 2 ul of fresh, whole blood was added to the prepared substrate plate. The prepared x-plate was then pressed firmly onto the blood sample. Pictures were taken after one 1 minute of incubation using an iPhone 6s.
6. CD4 count per microliter calculation:
   6.1. X-plate pillar height: 10 um
   6.2 fov: field of view (the total area of the Q-card in the picture that is taken using either an iPhone or a fluorescent microscope)
   6.3. Volume of sample in a fov:
      6.3.1. Length (um) x Width (um) x Height (10 um)=Volume of the fov (um$^3$)
   6.4. 1 ul=$10^9$ um$^3$
   6.5. CD4 counts per microliter:
      6.5.1. CD4 counts in the FOV×$10^9$ um$^3$/volume of the FOV (um$^3$)

$$\frac{\text{Total } CD4 \text{ Counts}}{\text{Volume of } FOV \text{ um}^3} \times \frac{1e9 \text{ um}^3}{uL}$$

Figure 8:
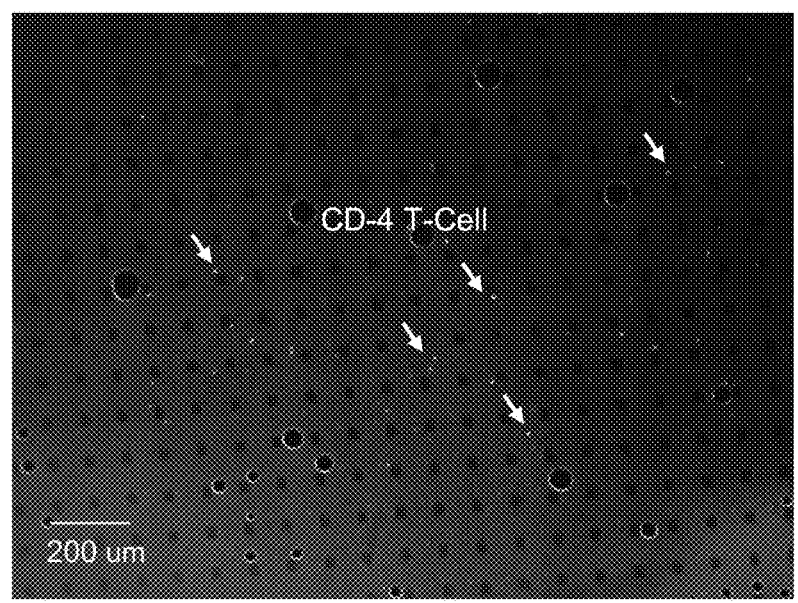
FIG. 8 shows exemplary pictures of CD4 T cell count with the QMAX device taken by iPhone-based microscopy. The cell is stained by detection antibody together with SYTO62 nonspecific nuclear dye.

6.6. Example: in the iPhone picture as shown in FIG. 8, there were 31 CD4 positive signals. FIG. 8 shows exemplary pictures of CD4 T cell count with the QMAX device taken by iphone based microscopy. The cell is stained by detection antibody together with SYTO62 nonspecific nuclear dye.
      6.6.1. CD4 counts per micrometer:

$$31 \times 10^9 \text{ um}^3/(1680 \text{ um} \times 2200 \text{ um} \times 10 \text{ um}) = 31 \times 10^9 \text{ um}^3/3.7 \times 10^7 \text{ um}^3 = 838/ul$$

Example 3

RNA Fluorescence In Situ Hybridization (RNA-FISH

RNA fluorescence in situ hybridization (RNA-FISH) is a molecular cytogenetic technique to detect and localize specific RNA targets (mRNA, lncRNA and miRNA) in single cells via fluorescence microscopy. The traditional RNA-FISH methods usually include multiple steps, e.g., fixation, permeabilization, hybridization and imaging. Although FISH has wide medical applications, the complexity of the technique limits its potential in rapid diagnostics. Therefore, it is desirable to develop a fast, accurate, portable, and/or inexpensive RNA-FISH assay, which can be conducted by a non-professional. The current invention satisfies these needs.

1. Materials:

Stellaris® FISH Probes, Human GAPDH with Quasar® 670 Dye (BioSearch Technologies, cat #SMF-2019-1).

Q-card with 10 pm height of pillar.

2. Procedures:

Coating plate. X-plate with 10 pm height pillar was printed with 0.25 uM of Quasar® 670 labeled FISH probes with different concentration of Zwittergent (Sigma-Aldrich) as surfactant in 50% Stellaris RNA FISH hybridization buffer (BioSearch Technologies, cat #SMF-HB1-10) containing 3.5% formamide and air-dried.

Adding sample. 3 µL fresh whole blood was dropped onto the center of substrate plate and covered by X-plate.

Staining. The card was incubated at room temperature for 1 minute.

Imaging. The stained card was imaged by iPhone 6s with external laser illumination.

3. Results:

An embodiment of a X-FISH device, which comprises a first plate (X-plate) and a second plate (substrate plate). Specific probes and surfactants (e.g., Zwittergent) are printed on X-plate. After drop blood samples on substrate plate, X-plate is covered and pressed on substrate plate. One minute later, the device is inserted to smart phone device for imaging and analyzing. (b) is an illustration to detect specific RNA expressed in white blood cells by X-FISH. Pillars on X-plates make a gap between the two plates, where the assay takes place. Printed probes and surfactants (e.g., Zwittergent) are dissolved in blood. surfactants (e.g., Zwittergent) lyse red blood cells, and also permeabilize white blood cells to promote probes entering cells to bind target RNA. Of note, the probes are designed to bind target RNA in series to amplify signals.

A flowchart description for X-FISH. Preparation is to print X-plate with fluorophore labeled detection probes and surfactants. Assay includes apply sample to substrate plate, cover with X-plate, incubate at room temperature for one minute, and insert to smart phone device for readouts.

Figure 5:
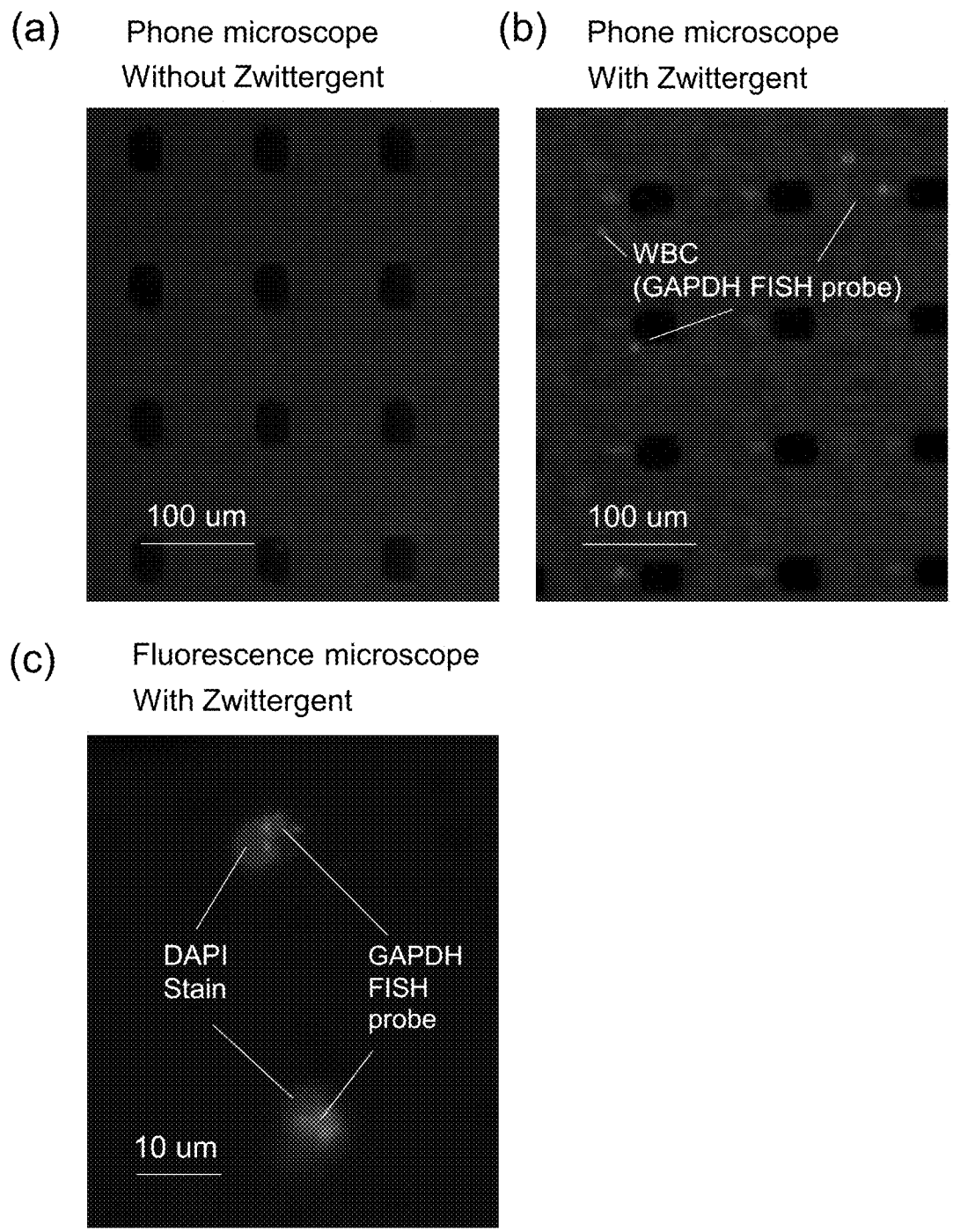
FIG. 5 shows effects of different Zwittergent concentrations on white blood cell permeabilization during the fast FISH in QMAX with GAPDH probes. (a) 0.625 mg/mL Zwittergent in blood gives no FISH signal with GAPDH probes observed by smartphone-based microscopy. (b) Zwittergent give strong fluorescence signal from GAPDH labeled white blood cells observed by smartphone-based microscopy and (c) fluorescence microscopy (DAPI WBC nuclear counterstain was used in (c).

FIG. 5 shows effects of different Zwittergent concentrations on white blood cell permeabilization during the fast FISH in QMAX with GAPDH probes. (a) 0.625 mg/mL Zwittergent in blood gives no FISH signal with GAPDH probes observed by smartphone-based microscopy. (b) 2.5 mg/mL Zwittergent and above (5 mg/mL) give strong fluorescence signal from GAPDH labeled white blood cells observed by smartphone-based microscopy and (c) fluorescence microscopy (DAPI WBC nuclear counterstain was used in (c)).

Example 4

*Chlamydia* Staining

In the experiments, mouse anti-*chlamydia* (Abcam, cat #ab41196) was used for staining and *chlamydia* antigen control slide (MBL Bion, cat #QCHE-4502) was used as the device to hold the sample.

In one of the experiments, slides with fixed human tissue cells infected by *chlamydia* were incubated with 1 uL of DyLight633 labeled anti-*chlamydia* antibody with 40 ug/mL for 30 seconds. X-plate with 30 um pillar height was used in the QMAX immunostaining. The slides were then washed by PBST for three times and images were taken by fluorescence microscope. BF: bright field. DL633: DyLight633 fluorescence.

Figure 6:
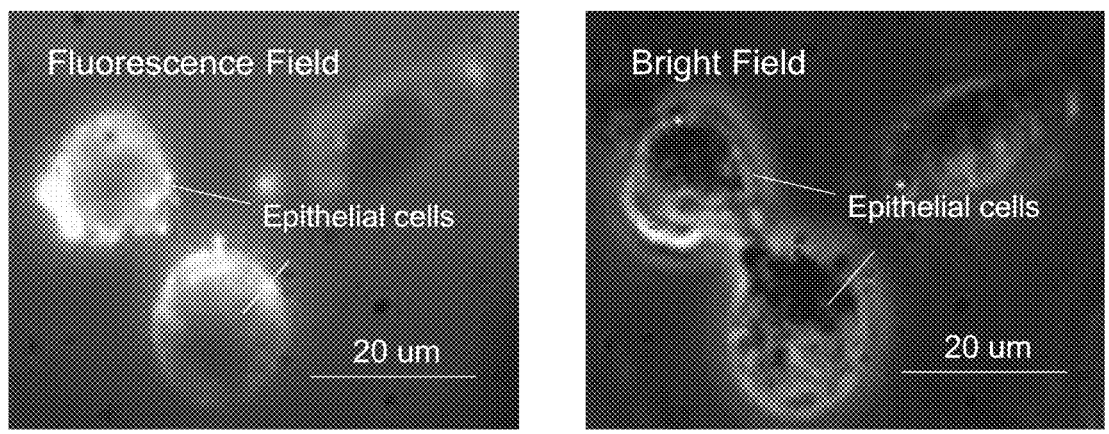
FIG. 6 shows exemplary pictures of *chlamydia* staining with the QMAX device without the optional washing step. (a) *Chlamydia* positive cells are stained with strong fluorescence; and (b) *Chlamydia* negative cells are not stained with fluorescence. In the experiment, slides with fixed human tissue cells infected by *chlamydia* were incubated with 1 uL of DyLight633 labeled anti-*chlamydia* antibody with 40 ug/mL for 2 min. X-plate with 30 um pillar height was used in the QMAX immunostaining. Images were taken by microscope without washing.
Figure 6:
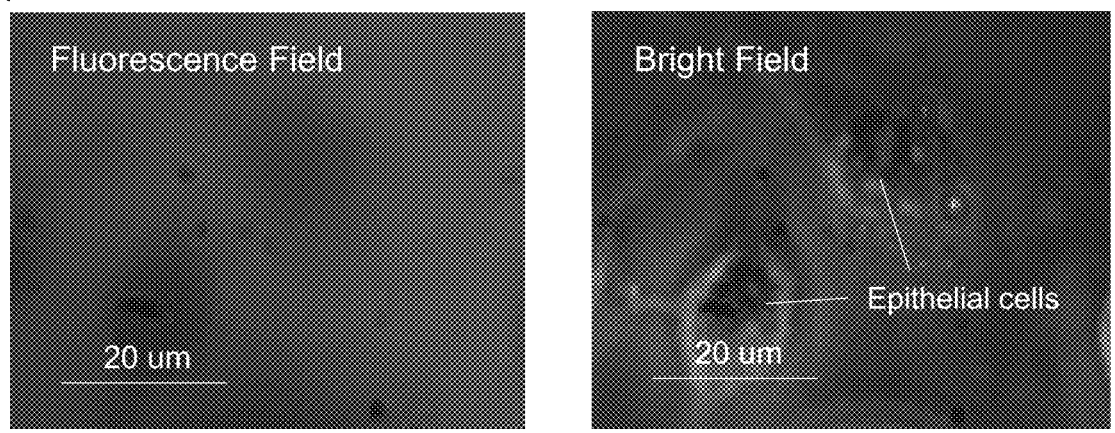

FIG. 6 shows exemplary pictures of *chlamydia* staining with the QMAX device without the optional washing step. In the experiments, slides with fixed human tissue cells infected by *chlamydia* were incubated with 1 uL of DyLight633 labeled anti-*chlamydia* antibody with 40 ug/mL for 1 min. X-plate with 30 um pillar height was used in the QMAX immunostaining. Images were taken by fluorescence microscope without washing.

In the experiments with conventional staining, slides with fixed human tissue cells infected by *chlamydia* were incubated with 20 uL of DyLight633 labeled anti-*chlamydia* antibody with 40 ug/mL for 30 min. The slides were then washed by PBST for three times and images were taken by fluorescence microscope.

Additional Examples of Present Invention

One Step Staining Assay to Detect *Chlamydia*

AA1 A method for detecting *chlamydia* in a sample, comprising:
  (a) obtaining a first plate comprising, on its inner surface, a sample contact area that is configured to contact a sample;
  (b) depositing the sample in the sample contact area, wherein the sample is suspected to comprise cells infected with *chlamydia*; and
  (c) depositing a *chlamydia* staining medium on the sample, wherein the staining medium comprises a *chlamydia*-binding antibody, and the staining medium and the sample form a mixture;
  (d) covering the mixture of the sample and the staining medium with a second plate, (e) pressing the first plate and the second plate so that at least part of the mixture is compressed into a thin layer;
  (f) incubating for a predetermined period of time that is about 60 seconds or less; and
  (g) detecting a *chlamydia*-related signal from the mixture.

AA2 The method of any prior embodiments, wherein the predetermined period of time that is about 30 seconds or less.

AA3 The method of any prior embodiments, wherein the predetermined period of time that is about 15 seconds or less.

AA4 The method of any prior embodiments, wherein the *chlamydia* antibody is fluorescently labeled.

AA5 The method of any prior embodiments, wherein the thin layer has a uniform thickness that is less than 100 um.

AA6 The method of any prior embodiments, wherein the thin layer has a uniform thickness that is less than 50 um.

AA7 The method of any prior embodiments, wherein the thin layer has a uniform thickness that is about 30 um or less.

AA8 The method of any prior embodiments, wherein the *chlamydia*-related signal is detected by imaging the sample.

One Step Sandwich Assay for Testing *Chlamydia*

AB1 A method for detecting *chlamydia* in a sample, comprising:
  (a) obtaining a first plate comprising, on its inner surface, a sample contact area that has a binding site, wherein the binding site comprises an immobilized capture antibody that binds to *chlamydia* in a sample that is suspected to contain *chlamydia*;
  (b) obtaining a second plate comprising, on its inner surface, a sample contact area that has a storage site, wherein the storage site comprises a detection antibody that is capable of, upon contacting the sample, diffusing in the sample, and wherein the capture antibody and detection antibody bind to different sites in the *chlamydia* to form a capture antibody-*chlamydia*-detection antibody sandwich;

(c) depositing the sample on one or both of the sample contact areas of the plates; (d) after (c), bringing the two plates to a closed configuration, wherein, in the closed configuration, at least part of the sample deposited in (c) is confined between the sample contact areas of the two plates, and has an average thickness in the range of 0.01 to 200 pm; and (e) detecting a signal related to *chlamydia* captured by the capture antibody.

AB2. The method of any prior AB embodiments, wherein the sample is from a human subject.

AB3. The method of any prior AB embodiments, wherein the capturing site further comprises a protein stabilizer.

AB4. The method of any prior AB embodiments, wherein the storage site further comprises a protein stabilizer.

AB5. The method of any prior AB embodiments, wherein the detection antibody comprises a fluorescent label.

AB6. The method of any prior AB embodiments, wherein the sample between the two plates has a uniform thickness in the range of 0.5 to 50 um.

AB7. The method of any prior AB embodiments, wherein the sample between the two plates has a uniform thickness in the range of 1 to 35 um.

AB8. The method of any prior AB embodiments, further comprising determining the presence or absence of *chlamydia*.

AB9. The method of any prior AB embodiments, wherein the overall time for steps (a) to (e) is less than 10 minutes.

AB10. The method of any prior AB embodiments, wherein the overall time for steps (e) to (e) is less than 3 minutes.

AB11. The method of any prior AB embodiments, wherein the overall time for steps (a) to (e) is less than 2 minutes.

Additional Features

AC1. The method of any prior embodiments, wherein one or both of the sample contact areas comprise spacers, wherein the spacers regulate the spacing between the sample contact areas of the plates when the plates are in the closed configuration.

AC2. The method of any prior embodiments, wherein the first plate comprises a plurality of binding sites and the second plate comprises a plurality of corresponding storage sites, wherein each biding site faces a corresponding storage site when the plates are in the closed configuration.

AC3. The method and device of any prior embodiment, wherein the detection antibody is dried on the storage site.

AC4. The method of any prior embodiments, wherein the capture antibody at the binding site are on an amplification surface that amplifies an optical signal of the analytes or the captured detection agents in any prior embodiments.

AC5. The method of any prior embodiments, wherein the capture agents at the binding site are on an amplification surface that amplifies an optical signal of the analytes or the captured detection agents in any prior embodiments, wherein the amplification is proximity-dependent in that the amplification significantly reduced as the distance between the capture agents and the analytes or the detection agents increases.

AC6. The method of any prior embodiments, wherein the detection of the signal is electrical, optical, or both. (including but not limited to Fluorescence, SPR, etc.).

Quantifying CD4 Expressing Cells

In the processes for staining of CD4 expressing cells according to some embodiments of the present invention, a first plate (termed "X-plate") and a second plate (e.g. made from glass or acrylic) were obtained, wherein the first plate and the second plate are moveable relative to each other. In certain embodiments, the first plate and the second plate are not connected. In certain embodiments, the first plate and the second plate are connected by a turning structure (e.g. a hinge). Each of the plates have two surfaces: one inner surface and one outer surface, wherein the inner surfaces face each other when the plates are pressed against each other. On the inner surfaces, each plate comprises a sample contact area for contacting a liquid sample.

In some embodiments, a detecting agent (e.g. a labeled anti-CD4 antibody) is immobilized on the sample contact area of one or both of the plates. In certain embodiments, the detecting agent comprises an anti-CD4 antibody. In certain embodiments, the detecting agent is labeled with a fluorophore. In certain embodiments, the anti-CD4 antibody is labeled with Alex 647.

In step 2, when the plates are in an open configuration, in which the plates are separated apart, a liquid sample is deposited on the sample contact area of one or both of the plates. In certain embodiments, the sample is whole blood.

In step 3, the plates are pressed against each other into a closed configuration. In certain embodiments, the pressing is conducted with human hand. In the closed configuration, the plates are pressed against each other with a gap between them, and the sample is compressed into a thin layer. In certain embodiments, the thin layer has a uniform thickness. In certain embodiments, one of both of the plates comprise spacers that are fixed in one or both of the sample contact areas. When the plates are pressed into the closed configuration, the spacers regulate the thickness of the sample layer. In certain embodiments, the spacers have a pillar shape.

In step 4, the sample layer is imaged and the number of CD4 expressing cells are quantified.

In the experiments, the QMAX device has two plates. The first plate was a X-Plate with 2 um or 10 um pillar height, 30×40 um pillar size, 80 um inter spacing distance, and is made of 175 um thick PMMA. The second plate was 1 mm thick glass or acrylic. The Anti-CD 4 antibody with Alexa Fluor 647 labels was positioned on the second plate in either liquid form or dry form. In its liquid form, the anti-CD4 antibody is 5 to 50 ug/mL with a volume of 0.5 to 1 uL. The anti-CD4 antibody was printed into an array of 300 um period and dried, with a surface concentration of 1 to 100 ng/cm$^2$ after drying.

In the experiments, for step 2, the sample is fresh whole blood with a volume of ~1 uL.

In the experiment, for step 3, after the plates are pressed against each other, the sample layer is incubated with the detecting agent for about 60 seconds.

In the experiment, for step 4, the stained whole blood sample layer was imaged either with laboratory microscopy or with a mobile device-adaptor system.

One apparatus that is used to capture the images of the sample according to some embodiments of the present invention is following. With iPhone as an example, the iPhone/reader setup uses laser diode as a light source. The laser diode has 638 nm central wavelength with 10 to 20 mW power. The excitation filter before the light source is 650 nm short pass. The light is reflected by an aluminum mirror onto the back of QMAX device with a typical illumination area of 1 mm×4 mm. The observation system is at the front of QMAX device with an iPhone adding an emission filter and lens. The emission filter is 670 nm long pass. The lens has focus distance around 4 mm and N.A. of 0.2.

Fluorescence photo of CD-4 stained whole blood in 2 um thick QMAX card under phone/reader system. The left photo is using relative high antibody concentration of 50 ug/mL and right photo is using antibody concentration of 10 ug/mL. The fluorescence photo shows clear fluorescence of stained CD-4 T cells. (b) Fluorescence photo of CD-4 stained whole blood in 10 um thick QMAX card under phone/reader system. The left photo is using relative high antibody concentration of 50 ug/L and right photo is using antibody concentration of 10 ug/mL. CD-4 T cells is not observed under 10 um QMAX, which might due to the iPhone reader's lower sensitivity and dynamic range compared with inverted microscopy system.

The number of CD4 expressing T cells counted with the QMAX device and the iPhone-laser setup are listed below. CD4 T Cells counted by QMAX system is 900/uL with a sample known T cell value between 500 to 1600/uL.

In some embodiments, the staining comprises the following steps:
  (a) obtaining a first plate and a second plate, wherein each plate comprises, on its respective inner surface, a sample contact area that is configured to contact a liquid sample,
    wherein a detecting agent is positioned on the sample contact area of one or both of the plates, and
    wherein the detecting agent is configured to specifically bind to the biomarker,
  (b) depositing the sample in the sample contact area, wherein the sample comprises cells that express the biomarker;
  (c) pressing the first plate and the second plate to compress the sample into a thin layer, which is at least partly confined by the two sample contact areas that face each other;
  (d) incubating for a predetermined period of time that is about 60 seconds or less; and
  (e) quantifying the cells expressing the biomarker by imaging the sample layer and counting the cells expressing the biomarker.

An exemplary flow chart that demonstrates the process to conduct the staining assay for CD4 expressing cells, comprises the following steps:
  (a) obtaining a first plate and a second plate, wherein each plate comprises, on its respective inner surface, a sample contact area that is configured to contact a liquid sample,
    wherein a detecting agent is positioned on the sample contact area of one or both of the plates, and
    wherein the detecting agent is configured to specifically bind to the biomarker,
  (b) depositing the sample in the sample contact area, wherein the sample comprises cells that express the biomarker;
  (c) pressing the first plate and the second plate to compress the sample into a thin layer, which is at least partly confined by the two sample contact areas that face each other;
  (d) incubating for a predetermined period of time that is about 60 seconds or less; and
  (e) quantifying the cells expressing the biomarker by imaging the sample layer and counting the cells expressing the biomarker.

Examples of Present Invention

One Step Staining Assay for CD4 T Cells in Whole Blood

BA1.1 A method for quantifying cells that express a biomarker in a sample, comprising:
  (a) obtaining a sample holder that is configured to hold a liquid sample that contains an analyte, wherein a detecting agent is positioned in the sample holder and is configured to specifically bind to the biomarker;
  (b) depositing the sample in the sample contact area, wherein the sample comprises cells that express the biomarker; and the sample is in contact with the detecting agent in the sample holder;
  (c) adjusting the sample holder to compress the sample into a thin layer,
  (d) incubating for a predetermined period of time; and
  (e) quantifying the cells expressing the biomarker by imaging the sample layer and counting the cells expressing the biomarker.

BA1.2 A method for quantifying cells that express a biomarker in a sample, comprising:
  (a) obtaining a first plate and a second plate, wherein each plate comprises, on its respective inner surface, a sample contact area that is configured to contact a liquid sample,
    wherein a detecting agent is positioned on the sample contact area of one or both of the plates, and
    wherein the detecting agent is configured to specifically bind to the biomarker,
  (b) depositing the sample in the sample contact area, wherein the sample comprises cells that express the biomarker;
  (c) pressing the first plate and the second plate to compress the sample into a thin layer, which is at least partly confined by the two sample contact areas that face each other;
  (d) incubating for a predetermined period of time that is about 60 seconds or less; and
  (e) quantifying the cells expressing the biomarker by imaging the sample layer and counting the cells expressing the biomarker.

BA1.3 A method for quantifying cells that express CD4 (cluster of differentiation 4) in a blood sample, comprising:
  (a) obtaining a first plate and a second plate, wherein each plate comprises, on its respective inner surface, a sample contact area that is configured to contact a blood sample,
    wherein a detecting agent is positioned on the sample contact area of one or both of the plates, and
    wherein the detecting agent is configured to specifically bind to CD4,
  (b) depositing the blood sample in the sample contact area, wherein the blood sample comprises cells that express CD4;
  (c) pressing the first plate and the second plate to compress the blood sample into a thin layer, which is at least partly confined by the two sample contact areas that face each other;
  (d) incubating for a predetermined period of time that is about 60 seconds or less; and
  (e) quantifying the CD4 expressing cells by imaging the sample layer and counting the cells expressing CD4.

BA2.1 An apparatus for quantifying cells that express a biomarker in a sample, comprising:
  a sample holder that is configured to hold a liquid sample that contains cells that express a biomarker, wherein a detecting agent is positioned in the sample holder and is configured to specifically bind to the biomarker; and an adaptor that is configured to accommodate the sample holder and be attachable to a mobile device, wherein:
  i. the mobile device comprises an imager,
  ii. the adaptor is configured to position the sample in a field of view (FOV) of the imager when the adaptor is attached to the mobile device, and
  iii. the imager is configured to capture images of the sample, thereby detecting/measuring a signal that is generated by the binding of the biomarker with the detecting agent after the sample is incubated with the detecting agent for a predetermined period of time that is about 60 seconds or less.

BB1.1 The method or apparatus of any prior embodiments, wherein the predetermined period of time that is about 30 seconds or less.

BB1.2 The method or apparatus of any prior embodiments, with the proviso that the sample contact areas are not washed after step (d).

BB1.3 The method or apparatus of any prior embodiments, wherein the detecting agent is an antibody.

BB1.4 The method or apparatus of any prior embodiments, wherein the antibody is labeled with a fluorophore.

BB1.5 The method or apparatus of any prior embodiments, wherein the detecting agent is labeled with signaling molecule that emits a signal upon excitation.

BB1.6 The method or apparatus of any prior embodiments, wherein the thin layer has a uniform thickness that is about equal to or less than 10 um.

BB1.7 The method or apparatus of any prior embodiments, wherein the thin layer has a uniform thickness that is about equal to or less than 2 um.

BB1.8 The method or apparatus of any prior embodiments, wherein the sample is whole blood.

BB1.9 The method or apparatus of any prior embodiments, wherein the biomarker is CD4 (cluster of differentiation 4).

BB1.10 The method or apparatus of any prior embodiments, wherein the cells are T cells.

BB1.11 The method or apparatus of any prior embodiments, wherein the detecting agent is immobilized on the sample contact area.

Machine Learning (ML) for Image-Based Assaying

In the present invention, machine learning model for detecting objects in the image-based assay is built from the training data. In some embodiment, the machine learning based detection is performed on the image for assaying, and in some embodiment, the machine learning based detection is performed on the transformed image for assaying that has higher contrast and lower signal-to-noise ratio. It begins with the action of collecting a training set of images, DB0, taken by the imager for assaying. These images are collected by taking a plural of images on samples in the sample holding device, e.g. QMAX card. Then it takes each training image from DB0 and label the objects of interest in the image for training. The labeled images are saved in a separate training set DB1 for machine learning model building.

In machine learning model training, it takes the labeled training database DB1, and select a machine learning model structure, in a form of deep neural network, to train the model against the training database DB1. In some embodiment, a machine learning model of RetinaNet is used, and in some other embodiment, a machine learning model of Fast-RCNN is selected. Tensorflow and PyTourch are used to train the machine learning model using the training database DB1 for detection and segmentation. The machine learning model training process ends after certain iterations over the training data in DB1 when the loss function on the training set DB1 or on a separate evaluation image data set meets the preset stopping criterion. The machine learning model obtained from the machine learning training process is saved for the assaying applications.

During the assaying, the image of the sample is the input to the machine learning based inference module. The machine learning inference module performs the machine learning based detection and segmentation based on the model obtained in the previous training process based on the training set DB1. The detected objects and their locations are saved in a database which can be searched and retrieved for the image-based assaying applications.

In some embodiments, the machine learning model training is performed on a local computing server, and in some embodiments, the machine learning model training is performed in a hybrid-cloud for scalability and efficiency. In the image-based assaying, the machine learning based detection and segmentation are performed either on the device or using a distributed computing resources, such as a hybrid-cloud using both local and cloud resources, depending on the computational complexity, resources on the device, network connection, assaying latency requirements, and so forth.

Other Embodiments

The disclosure includes a variety of embodiments, which can be combined in multiple ways as long as the various components do not contradict one another. These embodiments include not only the disclosures in the current file, but also the documents that are herein referenced, incorporated, or to which priority is claimed.

(1) Q-Card, Spacer and Uniform Sample Thickness

The devices, systems, and methods herein disclosed can include or use Q-cards, spacers, and uniform sample thickness embodiments for sample detection, analysis, and quantification. In some embodiments, the Q-card comprises spacers, which help to render at least part of the sample into a layer of high uniformity.

The devices, systems, and methods herein disclosed can include or use Q-cards, spacers, and uniform sample thickness embodiments for sample detection, analysis, and quantification. In some embodiments, the Q-card comprises spacers, which help to render at least part of the sample into a layer of high uniformity. The structure, material, function, variation and dimension of the spacers, and the uniformity of the spacers and the sample layer, are disclosed in the abovementioned PCT Application (designating U.S.) Nos. PCT/US2016/046437 and PCT/US2016/051775, and the corresponding US Provisional Application Nos.

Additional Notes

Further examples of inventive subject matter according to the present disclosure are described in the following enumerated paragraphs.

As used herein, the terms "adapted" and "configured" mean that the element, component, or other subject matter is designed and/or intended to perform a given function. Thus, the use of the terms "adapted" and "configured" should not be construed to mean that a given element, component, or other subject matter is simply "capable of" performing a given function. Similarly, subject matter that is recited as being configured to perform a particular function may additionally or alternatively be described as being operative to perform that function.

As used herein, the phrase, "for example," the phrase, "as an example," and/or simply the terms "example" and "exemplary" when used with reference to one or more components, features, details, structures, embodiments, and/or methods according to the present disclosure, are intended to convey that the described component, feature, detail, structure, embodiment, and/or method is an illustrative, non-exclusive example of components, features, details, structures, embodiments, and/or methods according to the present disclosure. Thus, the described component, feature, detail, structure, embodiment, and/or method is not intended to be limiting, required, or exclusive/exhaustive; and other components, features, details, structures, embodiments, and/or methods, including structurally and/or functionally similar and/or equivalent components, features, details, structures, embodiments, and/or methods, are also within the scope of the present disclosure.

As used herein, the phrases "at least one of" and "one or more of," in reference to a list of more than one entity, means any one or more of the entity in the list of entity, and is not limited to at least one of each and every entity specifically listed within the list of entity. For example, "at least one of A and B" (or, equivalently, "at least one of A or B," or, equivalently, "at least one of A and/or B") may refer to A alone, B alone, or the combination of A and B.

As used herein, the term "and/or" placed between a first entity and a second entity means one of (1) the first entity, (2) the second entity, and (3) the first entity and the second entity. Multiple entity listed with "and/or" should be construed in the same manner, i.e., "one or more" of the entity so conjoined. Other entity may optionally be present other than the entity specifically identified by the "and/or" clause, whether related or unrelated to those entities specifically identified.

Where numerical ranges are mentioned herein, the invention includes embodiments in which the endpoints are included, embodiments in which both endpoints are excluded, and embodiments in which one endpoint is included and the other is excluded. It should be assumed that both endpoints are included unless indicated otherwise. Furthermore, unless otherwise indicated or otherwise evident from the context and understanding of one of ordinary skill in the art.

The invention claimed is:

1. A method of enhancing a homogenous detection of an analyte in a cell that is in a sample, comprising:
   (a) providing a first plate and a second plate, each has a sample contact area on its surface, wherein the sample contact surfaces contact a sample comprising a cell that contains or is suspected of containing an analyte,
   (b) providing a detection probe that specifically binds the analyte and is capable of emitting a light at a wavelength, wherein the detection probe diffuses in the sample;
   (c) providing an optical enhancer that diffuses in the sample, binds to the cell, and is capable of emitting a light of a wavelength that overlaps with or within a 150 nm from the wavelength of the light emitted by the detection probe;
   (d) sandwiching the sample, the detection probe, and the optical enhancer between the two sample contact areas of the two plates to form a thin layer of a thickness of 200 microns (um) or less; and
   (e) imaging, using an imager, after step (d) and without using any washing step, the thin layer to detect the cell that has the analyte bound to the detection probe;
   wherein the thin layer has a thickness that is selected so that for a given concentration of the cell in the thin layer, each individual cell does not substantially overlap other cells in the imaging;
   wherein the thickness of the thin layer, the concentration of the detection probe in the sample, or the concentration of the optical enhancer in the sample is selected to make, in step (e) of imaging, in the thin layer, the location having a bound detection probe is distinguishable from the locations not having the bound detection probe, wherein the bound detection probe is the detection probe bound to the analyte in the cell.

2. The method of claim 1, wherein the detection probe is deposited on at least one of the sample contact areas.

3. The method of claim 1, wherein the detection probe and the optical enhancer are deposited on at least one of the sample contact areas.

4. The method of claim 1, wherein the imaging further comprises a step of machine learning in detecting the analyte.

5. The method of claim 1, wherein the optical enhancer is a cell permeant dye that readily penetrates a cell wall and stains the components of the same without requiring the additional presence of a permeabilizing agent.

6. The method of claim 1, wherein the analyte comprises a molecule, cells, tissues, viruses, or nanoparticles with different shapes, wherein the molecule comprising a protein, peptides, DNA, RNA, or nucleic acid.

7. The method of claim 1, wherein the cell is a prokaryote or eukaryote.

8. The method of claim 1, wherein the cell in a sample has a quantity of one or more than one.

9. The method of claim 1, wherein the detection probe is a label, wherein the label is immunoassay antibody label, RNA label, or staining dye and is coated on the plate with a final concentration in sample of 0.05 mg/mL, 0.15 mg/mL, 0.3 mg/mL, 0.5 mg/mL, 1.0 mg/mL, or in a range between any of the two values.

10. The method of claim 1, wherein the detection probe is a fluorescent RNA probe.

11. The method of claim 1, wherein an average thickness of the layer is about equal to a minimum dimension of the analyte in the sample.

12. A device for enhancing a homogenous detection of an analyte in a cell that is in a sample, comprising:
    (a) a first plate and a second plate, each has a sample contact area on its surface, wherein the sample contact surfaces contact a sample comprising a cell that contains or is suspected of containing an analyte,
    (b) a detection probe that specifically binds the analyte and is capable of emitting a light at a wavelength, wherein the detection probe diffuses in the sample;
    (c) an optical enhancer that binds to the cell and emits a light of a wavelength that overlaps with or within a 150 nm from the wavelength of the light emitted by the detection probe;
    wherein the first and second plates sandwich the sample, the detection probe, and the optical enhancer between the two sample contact areas to form a thin layer of a thickness of 200 microns (um) or less; and
    wherein the thin layer has a thickness is selected so that for a given concentration of the cell in the sample, each individual cell does not substantially overlap other cells for an imaging;
    wherein the thickness of the thin layer, the concentration of the detection probe in the sample, or the concentration of the optical enhancer in the sample is selected to make, in the imaging, in the thin layer, the location having a bound detection probe is distinguishable from the locations not having the bound detection probe, wherein the bound detection probe is the detection probe bound to the analyte in the cell.

13. The device of claim 12, further comprising an imager that images the thin layer to detect the bound detection probe.

14. The device of claim 12, wherein the optical enhancer is coated on one or both of the sample contact areas.

15. The device of claim 12, wherein the thin layer has a thickness selected to make, in the step (e) of imaging, in the thin layer, the location having the bound detection probe is distinguishable from the locations not having the bound detection probe, wherein the bound detection probe is the detection probe bound to the analyte in the cell, the analyte is a nucleic acid and the detection probe is a probe for fluorescence in-situ hybridization (FISH).

16. The device of claim 12, wherein the detection probe is an immune probe.

17. The device of claim 12, wherein the analyte is a CD4.

18. The device of claim 12, wherein the first plate and the second plate are movable relative to each other into a different configuration, including an open configuration and a closed configuration, wherein:
in the open configuration, the first plate and the second plate are partially or entirely separated, and the sample is deposited in the sample contact area on one or both of the plates, and a separation sheet is removed from any contact with one or both of the plates; and
in the closed configuration at least part of the deposited sample is compressed by the two plates into a thin layer.

19. The method of claim 18, wherein at the closed configuration, the thickness of the thin layer is thin enough to enable the device to analyze the sample in 60 seconds or less.

20. The device of claim 12, further comprising spacers, wherein:
(i) the first plate and the second plate are movable relative to each other into a different configuration, including an open configuration and a closed configuration, and
(ii) one or both of the plates comprise spacers that are fixed with a respective plate,
wherein in an open configuration, the two plates are either completely or partially separated apart, the spacing between the plates is not regulated by the spacers, and the sample is deposited on one or both of the plates; and
wherein in the closed configuration, which is configured after the sample deposition in the open configuration, at least a part of the sample is between the two plates and in contact with the two plates, and has a highly uniform thickness that is regulated by the spacers and the two sample surfaces of the plates and is equal to or less than 150 um.

21. The device of claim 20, wherein the spacers have a height of 30 um or less.

22. The device of claim 20, wherein the spacers have a height of 10 um or less.

23. The device of claim 20, wherein the spacers have a height of 2 um or less.

24. The device of claim 20, wherein the spacers have an inter-spacer distance in the range of 1 um to 200 um.

25. The device of claim 20, wherein the spacers have an inter-spacer distance in the range of 200 um to 1000 um.

26. The device of claim 20, wherein the detection probe is a fluorescent RNA probe.

27. The device of claim 26, wherein the spacers have a inter-space distance (ISD), a fourth power of the ISD divided by the thickness of the flexible plate (h) and the Young's modulus (E) of the flexible plate, $ISD^4/(hE)$, is equal to or less than $10^6$ $um^3$/GPa; and the thickness of the flexible plate times the Young's modulus of the flexible plate is in the range 60 to 750 GPa-um.

28. The device of claim 20, wherein the spacers function as a location marker, a scale marker, an imaging marker, or any combination thereof.

29. The device of claim 20, wherein the spacers have an inter-spacer distance in the range of 1 um to 50 um.

30. The device of claim 20, wherein the spacers have an inter-spacer distance in the range of 50 um to 120 um.

31. The device of claim 20, wherein the spacers have an inter-spacer distance in the range of 120 um to 200 um.

32. The device of claim 20, wherein the spacers have an inter-spacer distance that is substantially periodic.

33. The device of claim 20, wherein the spacers are pillars with a cross-sectional shape selected from round, polygonal, circular, square, rectangular, oval, elliptical, and any combination of the same.

34. The device of claim 20, wherein the spacers have a pillar shape and have a substantially flat top surface, wherein, for each spacer, the ratio of the lateral dimension of the spacer to its height is at least 1.

35. The device of claim 20, wherein a minimum lateral dimension of the spacer is in the range of 0.5 um to 100 um.

36. The device of claim 12, further comprising a non-volatile storage medium that has an algorithm of machine learning for detecting the analyte.

37. The device of claim 12, wherein the thickness of the thin layer is 2 um or less.

38. The device of claim 12, wherein the sample is from a biological sample, an environmental sample, a chemical sample, or a clinical sample.

39. The device of claim 12, further comprising a reagent coated on the device for making protein cross link, the reagent comprises formaldehyde, glutaraldehyde, osmium tetroxide, potassium dichromate, or potassium permanganate.

40. The device of claim 12, wherein the optical enhancer emits a light of a wavelength that overlaps with or within a 30 nm from the wavelength of the light emitted by the detection probe.

41. The device of claim 12, wherein the device further comprises, on one or both plates, multi reagent layers including anti-conglutination, cell lysing, cell staining, release time control material layers, and their combinations.

42. The device of claim 41, wherein the anti-conglutination agent comprises ethylenediaminetetraacetic acid (EDTA), EDTA disodium, dipotassium ethylenediaminetetraacetic acid, or tripotassium ethylenediaminetetraacetic acid.

43. The device of claim 12, wherein one or both sample areas are coated with the cell stain agent comprising Wright's stain, Giemsa stain, May-Grünwald stain, Leishman's stain, Erythrosine B stain, and other fluorescence stain including Acridine orange dye, 3,3-dihexyloxacarbocyanine, Propidium Iodide, Fluorescein Isothiocyanate and Basic Orange 21) dye, Ethidium Bromide, Brilliant Sulfaflavine and a Stilbene Disulfonic Acid derivative, Erythrosine B or trypan blue, Hoechst 33342, Trihydrochloride, Trihydrate, and 4',6-Diamidino-2-Phenylindole, and YOYO.

44. The device of claim 12, further comprising a release time control material coated on the first or second plate, the release time control material comprises albumin, carbomers, carboxymethyl cellulose, carrageenan, chitosan, dextrin, polyethylene glycol, polyvinylpyrrolidone, or polyvinyl alcohol.

45. The device of claim 12, wherein one or both sample areas are coated with the chemicals comprising Surfactant, Zwittergent, 3-[N,N-Dimethyl(3-myristoylaminopropyl) ammonio]propanesulfonate (ASB-14), 3-[N,N-Dimethyl(3-palmitoylaminopropyl) ammonio]-propanesulfonate (ASB-16), 3-[(3-Cholamidopropyl)dimethylammonio]-1-propanesulfonate (CHAPS), Cationic surfactant NN-[Tris (hydroxymethyl) methyl]-N-alkyl-N,N-dimethyl ammonium chloride (IIa), IIb, IIc, IId, cetyltrimethylammonium chloride (CTAC), polyoxyethylene sorbitan monolaurate (TWEEN® 20), polyoxyethylene sorbitan monopalmitate (TWEEN® 40), polyoxyethylene sorbitan monostearate (TWEEN® 60), polyoxyethylene sorbitan monooleate (TWEEN® 80), Sodium lauryl sulfate (SLS), ammonium lauryl sulfate, cetyltrimethylammonium bromide (CTAB), sodium lauryl ether sulfate (SLES), sodium myreth sulfate, docusate, perfluorooctanesulfonate, alkyl-aryl ether phosphates, alkyl ether phosphates, cetylpyridinium chloride (CPC), benzalkonium chloride (BAC), benzethonium chloride (BZT), dimethyldioctadecylammonium chloride, dioctadecyldimethlyammonium bromide (DODAB), cocamidopropyl hydroxysultaine, cocamidopropyl betaine, narrow-range ethoxylate, octaethylene glycol monododecyl ether, pentaethylene glycol monododecyl ether, nonxynols, 2-[4-(2,4,4-trimethylpentan-2-yl)phenoxy]ethanol (TRITON X-100™), polyethoxylated tallow amine, cocamide monoethanolamine, cocamide diethanolamine, poloxamers, glycerol monostearate, glycerol monolaurate, sorbitan monolaurate, sorbitan monostearate, sorbitan tristearate, decyl glucoside, lauryl glucoside, octyl glucoside, lauryldimethylamine oxide, dimethyl sulfoxide, or phosphine oxide.

46. The device of claim 12, wherein one or both sample areas are coated with a reagent comprising non-ionic copolymer surfactant (Pluronic F-127), polyoxyl 35 castor oil (Cremophor EL), Polyoxyethylene-polyoxypropylene block copolymer (Pluronic F-68), Polyoxyethylene (40) stearate (Myrj 52), Polyoxyethylene lauryl ether (Brij 35), sodium oleate, sodium dodecyl sulfate, TWEEN® 20, TWEEN® 40, TWEEN® 60, TWEEN® 80, SLS, CTAB, CTAC, Tamoxifen, saponin, hydrochloric acid, sulfuric acid, nitric acid, phosphoric acid, lactic acid, ABS-14, ABS-16, quinine compounds, arsenic, dapsone, chromium/chromates, platinum salts, nickel compounds, copper, lead, cis-platinum, nitrites, nitrofurantoin, penicillin, phenazopyridine rho immune globulin, ribavirin, sulfonamides, sulfones.

47. The device of claim 12, wherein the detection probe is a label, wherein the label is immunoassay antibody label, RNA label, or staining dye and is coated on the plate with a final concentration in sample of 0.1 nM/mL, 0.5 nM/mL, 1 nM/mL, 5 nM/mL, 10 nM/mL, 15 nM/mL, 20 nM/mL, 50 nM/mL, or in a range between any of the two values.

48. The device of claim 12, wherein the thickness of the sample is 30 um or less.

49. The device of claim 12, wherein the thickness of the sample is 10 um or less.

50. The device of claim 12, wherein the concentration of the detection probe in the sample is 1 nM, 5 nM, 10 nM, 50 nM, 100 nM, 500 nM, 1 uM, 10 nM, 50 nM, 100 nM or in a range between any of the two values.

51. The device of claim 12, wherein the concentration of probe in the sample is 10 nM, 50 nM, 100 nM, 500 nM, 1 M, or in a range between any of the two values.

52. The device of claim 12, wherein the concentration of the optical enhancer in the sample is 10 nM, 50 nM, 100 nM, 500 nM, 1 μM, 2 μM, 5 μM, 10 μM, 20 μM, 50 μM, 100 μM, 500 μM, or in a range between any of the two values.

53. The device of claim 12, wherein the concentration of the optical enhancer in the sample is 1 μM, 2 μM, 5 μM, 10 μM, 20 μM, 50 μM, or in a range between any of the two values.

54. The device of claim 12, wherein the optical enhancer's light wavelength and the probe's light wavelength is within 1 nm, 5 nm, 10 nm, 20 nm, 50 nm, or 100 nm.

55. The device of claim 12, wherein the optical enhancer's light wavelength and the probe's light wavelength is within 1 nm, 2 nm, 5 nm, 10 nm, 20 nm, or 50 nm.

56. The device of claim 12, wherein one or both plates comprises a scale marker, either on a surface of or inside the plate, that provides information of a lateral dimension of a structure of the sample and/or the plate.

57. The device of claim 12, wherein one or both of the sample contact surfaces comprises a scale marker, a location marker, or an imaging marker.

58. The device of claim 12, wherein the first plate and the second plate are connected by a hinge.

59. The device of claim 12, wherein the thickness of the thin layer is so thin that the saturation incubation time of the sample with the detection probe is 60 seconds or less.

60. The device of claim 12, wherein the binding of the optical enhancer to the cell is specific.

61. The device of claim 12, wherein the binding of the optical enhancer to the cell is nonspecific.

62. The device of claim 12, wherein the binding of the optical enhancer to the target cell is nonspecific, wherein the optical enhancer binds to nucleic acids of the target cell.

63. A system of enhancing a homogenous detection of an analyte in a cell that is in a sample, comprising:
(a) the device of claim 12; and
(b) a communication device, wherein the communication device comprising (i) one or a plurality of cameras for the detecting signal and/or imaging the sample; and (ii) electronics, signal processors, hardware and software for receiving and/or processing the detected signal and/or the image of the sample.

64. The device of claim 63, wherein the communication device is further configured to communicate information of the test and the subject to a cloud network, the cloud network is configured to process the information to refine the test results, and the refined test results will send back the subject.

65. The device of claim 63, wherein the communication device is configured to receive a prescription, diagnosis or a recommendation from a medical professional.

66. A device for a rapid homogenous detection of an analyte inside a membrane of a cell in a sample, comprising:
(a) a first plate and a second plate, each has a sample contact area on its surface, wherein the sample contact surfaces contact a sample comprising a cell that contains or is suspected of containing an analyte inside of the cell membrane;
(b) a detection probe that specifically binds the analyte and is capable of emitting a light at a wavelength, wherein the detection probe diffuses in the sample;
(c) a permeabilization agent that makes a membrane of the cell permeable to the detection probe;
wherein the first and second plates are configured to sandwich the sample, the detection probe, and the permeabilization agent between the two sample contact areas of the two plates to form a thin layer of a thickness of 200 microns (um) or less;
wherein the thin layer sample thickness is configured so that for a given concentration of the cell in the sample, each individual cell does not substantially overlap other cells in an imaging, wherein the imaging is performed without a washing step;

wherein the thickness of the thin layer and the concentration of the detection probe in the sample, are configured to make, in the imaging, in the thin layer, the location having the detection probe that bound to the analyte inside the cell membrane is distinguishable from the locations that do not have the cell; and wherein the washing step is a step for removing unbound detection probe, permeabilization reagent, or both from the sample contact areas.

67. The device of claim 66, further comprising an optical enhancer, wherein the first and second plates are configured to sandwich the sample, the detection probe, the permeabilization agent, and the optical enhancer between the two sample contact areas of the two plates to form a thin layer of a thickness of 200 microns (um) or less;

wherein the optical enhancer diffuses in the sample, binds to the cell, and is capable of emitting a light of a wavelength that overlaps with or within a 150 nm from the wavelength of the light emitted by the detection probe;

wherein the thin layer sample thickness is configured so that for a given concentration of the cell in the sample, each individual cell does not substantially overlap other cells in an imaging, wherein the imaging is performed without a washing step;

wherein the thickness of the thin layer, the concentration of the detection probe in the sample, or the concentration of the optical enhancer in the sample is configured to make, in the step (e) of imaging, in the thin layer, the location having the bound detection probe is distinguishable from the locations not having the bound detection probe, wherein the bound detection probe is the detection probe bound to the analyte in the cell; and wherein the washing step is a step of removing unbound detection probe, permeabilization reagent, or both from the sample contact areas.

68. The device of claim 67, wherein the detection probe, the permeabilization agent, or the optical enhancer is deposited on one or both of the sample surfaces.

69. The device of claim 66, wherein the permeabilization agent makes cell membrane or cell nucleus permeable, comprising TRITON X-100™, surfactant, Zwittergent, 3-[N,N-Dimethyl(3-myristoylaminopropyl)ammonio]propanesulfonate (ASB-14), 3-[N,N-Dimethyl(3-palmitoylaminopropyl)ammonio]-propanesulfonate (ASB-16), 3-[(3-cholamidopropyl)dimethylammonio]-1-propanesulfonate (CHAPS), Cationic surfactant NN-[Tris(hydroxymethyl)methyl]-N-alkyl-N,N-dimethyl ammonium chloride (IIa), IIb, IIc, IId, CTAC, TWEEN® 20, TWEEN® 40, TWEEN® 60, TWEEN® 80, Sodium lauryl sulfate (SLS), ammonium lauryl sulfate, CTAB, sodium lauryl ether sulfate (SLES), sodium myreth sulfate, docusate, perfluorooctanesulfonate, alkyl-aryl ether phosphates, alkyl ether phosphates, CTAB, cetylpyridinium chloride (CPC), benzalkonium chloride (BAC), benzethonium chloride (BZT), dimethyldioctadecylammonium chloride, dioctadecyldimethylammonium bromide (DODAB), cocamidopropyl hydroxysultaine, cocamidopropyl betaine, narrow-range ethoxylate, octaethylene glycol monododecyl ether, pentaethylene glycol monododecyl ether, nonxynols, TRITON X-100™, polyethoxylated tallow amine, cocamide monoethanolamine, cocamide diethanolamine, poloxamers, glycerol monostearate, glycerol monolaurate, sorbitan monolaurate, sorbitan monostearate, sorbitan tristearate, decyl glucoside, lauryl glucoside, octyl glucoside, lauryldimethylamine oxide, dimethyl sulfoxide, phosphine oxide.

70. The device of claim 69, wherein the Zwittergent is coated onto the first plate, or the second plate or both.

71. The device of claim 70, wherein one or both sample areas are coated with Zwittergent of an area concentration of 3 ng/mm$^2$, 5 ng/mm$^2$, 8 ng/mm$^2$, 12 ng/mm$^2$, 15 ng/mm$^2$, 25 ng/mm$^2$, 35 ng/mm$^2$, 50 ng/mm$^2$, 80 ng/mm$^2$, 100 ng/mm$^2$ or in a range between any of the two values.

72. The device of claim 66, wherein permeabilization agent is an agent making the cell membrane or cell nucleus of the cell permeable, by causing osmotic pressure difference between the cell membrane as dilution, or tuning salt concentration.

73. The device of claim 66, wherein acridine orange is coated onto the first plate, or the second plate or both.

74. The device of claim 66, wherein Methylene blue and Zwittergent is coated onto the first plate, or the second plate or both.

75. The device of claim 66, wherein acridine orange and Zwittergent is coated onto the first plate, or the second plate or both.

76. The device of claim 75, wherein one or both sample areas are coated with the acridine orange of an area concentration of 3 to 10 ng/mm$^2$ and Zwittergent is coated on the plate with an area concentration of 3 to 30 ng/mm$^2$.

77. The device of claim 66, wherein YOYO dye and Zwittergent is coated onto the first plate, or the second plate or both.

78. The device of claim 66, wherein one or both sample areas are coated with the cell stain agent comprising Wright's stain, Giemsa stain, May-Grünwald stain, Leishman's stain, Erythrosine B stain, and other fluorescence stain including Acridine orange dye, 3,3-dihexyloxacarbocyanine (DiOC6), Propidium Iodide (PI), Fluorescein Isothiocyanate (FITC) and Basic Orange 21 (B021) dye, Ethidium Bromide, Brilliant Sulfaflavine and a Stilbene Disulfonic Acid derivative, Erythrosine B or trypan blue, Hoechst 33342, Trihydrochloride, Trihydrate, and DAPI (4',6-Diamidino-2-Phenylindole, Dihydrochloride), YOYO, acid fuchsine, hematoxylin, Hoechst stains including Hoechst 33258 and Hoechst 33342, methyl green, methylene blue, Nile blue, Nile red, osmium tetraoxide, rhodamine, safranine, MeOSuc-AAPV-AMC, CFSE, BCECF/AM, silver nitrate, neutral red, pyronin Y, Calcein-AM, Dihydroethidium, Xylene Cyanol FF, Rhodamine 123, 4-Methylumbelliferyl palmitate, Fast Blue B Salt, Lucifer Yellow CH dipotassium salt, DAPI dilactate, or Propidium Iodide.

79. The device of claim 66, wherein the detection probe is a label, wherein the label is immunoassay antibody label, RNA label, or staining dye and is coated on the plate with a final concentration in sample of 1 nM/mL, 5 nM/mL, 10 nM/mL, 15 nM/mL, 20 nM/mL, or in a range between any of the two values.

80. A method for a rapid homogenous detection of an analyte inside a membrane of a cell in a sample, comprising:

(a) providing a first plate and a second plate, each has a sample contact area on its surface, wherein the sample contact surfaces contact a sample comprising a cell that contains or is suspected of containing an analyte inside of the cell membrane;

(b) providing a detection probe that specifically binds the analyte and is capable of emitting a light at a wavelength, wherein the detection probe diffuses in the sample;

(c) providing a permeabilization agent that makes a membrane of the cell permeable to the detection probe;

(d) sandwiching the sample, the detection probe, and the permeabilization agent between the two sample contact areas of the two plates to form a thin layer of a thickness of 200 microns (um) or less; and (e) imaging, after the step (d) and without a washing step, the thin layer to detect the cell that has the analyte bound to the detection probe;

wherein the thin layer sample thickness is configured so that for a given concentration of the cell in the sample, each individual cell does not substantially overlap other cells in the imaging;

wherein the thickness of the thin layer and the concentration of the detection probe in the sample, are configured to make, in the thin layer, the location having the detection probe that bound to the analyte inside the cell membrane is distinguishable from the locations that do not have the cell; and wherein the washing step is a step for removing unbound detection probe, permeabilization reagent, or both from the sample contact areas.

81. The method of claim 80, further comprising a label, wherein the label is immunoassay antibody label, RNA label, or staining dye and is coated on the plate with a final concentration in sample of 0.1 mg/mL, 0.5 mg/mL, 1.0 mg/mL, 1.5 mg/mL, 2.0 mg/mL, 5 mg/mL, 10 mg/mL, 50 mg/mL, or in a range between any of the two values.

82. A method of a homogenous detection of a Gram positive cell or Gram negative cell in a sample, comprising:

(a) providing a first plate and a second plate, each has a sample contact area on its surface, wherein the sample contact surfaces contact a sample that contains or is suspected of containing a Gram positive cell or Gram negative cell;

(b) depositing, on at least one of the sample contact areas, a Gram positive stain, a Gram negative stain, or both, wherein the Gram positive and Gram negative stains have two distinguishable colors; wherein the Gram positive stain stains only Gram positive cells while the Gram negative stain stains both Gram positive and negative cells; wherein, in a Gram positive cell that is stained by both Gram positive and negative stains, the Gram positive stain is distinguishable from the Gram negative stain;

(c) sandwiching the sample between the two sample contact areas of the two plates to make the sample forming a thin layer of a thickness of 150 microns (um) or less; and (d) imaging using an imager, after the step (c) and without using any washing step, the thin layer to detect cells that are stained by (i) Gram negative stain only, (ii) Gram positive stain; and (iii) both;

wherein the thin layer sample thickness is configured so that for a given concentration of the cell in the sample, each individual cell does not substantially overlap other cells in the imaging;

wherein a Gram positive cells displays Gram positive stain color, and a Gram negative cell displays Gram negative stain color only;

wherein the thickness of the thin layer, the concentration of the detection probe in the sample, or the concentration of the optical enhancer in the sample is configured to make, in the step (e) of imaging, in the thin layer, the location having the bound detection probe is distinguishable from the locations not having the bound detection probe, wherein the bound detection probe is the detection probe bound to the analyte in the sample.

83. The method of claim 82, further comprising a label, wherein the label is immunoassay antibody label, RNA label, or staining dye and is coated on the plate with a final concentration in sample of 100 mg/mL, 200 mg/mL, 300 mg/mL, or in a range between any of the two values.

84. The method of claim 80, further comprising an optical enhancer, wherein the first and second plates are configured to sandwich the sample, the detection probe, the permeabilization agent, and the optical enhancer between the two sample contact areas of the two plates to form a thin layer of a thickness of 200 microns (μm) or less;

wherein the optical enhancer diffuses in the sample, binds to the cell, and is capable of emitting a light of a wavelength that overlaps with or within a 150 nm from the wavelength of the light emitted by the detection probe;

wherein the thin layer sample thickness is configured so that for a given concentration of the cell in the sample, each individual cell does not substantially overlap other cells in an imaging, wherein the imaging is performed without a washing step; wherein the thickness of the thin layer, the concentration of the detection probe in the sample, or the concentration of the optical enhancer in the sample is configured to make, in the step (e) of imaging, in the thin layer, the location having the bound detection probe is distinguishable from the locations not having the bound detection probe, wherein the bound detection probe is the detection probe bound to the analyte in the cell; and wherein the washing step is a step of removing unbound detection probe, permeabilization reagent, or both from the sample contact areas.

85. The method of claim 84, wherein the detection probe, the permeabilization agent, or the optical enhancer is deposited on one or both of the sample surfaces.

* * * * *